US008901278B2

(12) United States Patent
Rau et al.

(10) Patent No.: US 8,901,278 B2
(45) Date of Patent: *Dec. 2, 2014

(54) PHARMACEUTICAL ANTIBODY COMPOSITIONS WITH RESISTANCE TO SOLUBLE CEA

(75) Inventors: Doris Rau, Unterhaching (DE); Susanne Mangold, München (DE); Peter Kufer, Moosburg (DE); Tobias Raum, München (DE)

(73) Assignee: Amgen Research (Munich) GmbH, Munich (DE)

( * ) Notice: Subject to any disclaimer, the term of this patent is extended or adjusted under 35 U.S.C. 154(b) by 144 days.

This patent is subject to a terminal disclaimer.

(21) Appl. No.: 13/324,823

(22) Filed: Dec. 13, 2011

(65) Prior Publication Data

US 2012/0121600 A1 May 17, 2012

Related U.S. Application Data

(63) Continuation of application No. 12/095,952, filed as application No. PCT/EP2006/012409 on Dec. 21, 2006, now abandoned.

(60) Provisional application No. 60/752,029, filed on Dec. 21, 2005.

(51) Int. Cl.
*C07K 16/30* (2006.01)
*A61K 39/00* (2006.01)

(52) U.S. Cl.
CPC ....... *C07K 16/3007* (2013.01); *C07K 2317/565* (2013.01); *C07K 2317/622* (2013.01); *A61K 2039/505* (2013.01); *C07K 2317/24* (2013.01); *C07K 2317/732* (2013.01); *C07K 2317/56* (2013.01)
USPC .................. 530/387.1; 530/350; 530/387.3; 530/387.7; 530/388.8

(58) Field of Classification Search
USPC ............. 530/350, 387.1, 387.3, 387.7, 388.8
See application file for complete search history.

(56) References Cited

U.S. PATENT DOCUMENTS 5,876,691 A * 3/1999 Chester et al. ............. 424/1.49
6,339,070 B1 * 1/2002 Emery et al. ............... 514/44 R

FOREIGN PATENT DOCUMENTS

WO WO 2004/032857 A2 4/2004

OTHER PUBLICATIONS

Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Winkler et al. (J. Immunol. Oct. 15, 2000; 165 (8): 4505-4514).*
The English Translation of the Notice of Reasons for Rejection received in Japanese Patent Application No. 2008-546269, dated Jan. 24, 2012.
Murakami, Masaaki, "Binding Reactivity of Monoclonal Anti-Carcinoembryonic Antigen (CEA) Antibodies with Cell Membrane-Bound CEA and with Free CEA in Solution" *Immunological Investigations*, USA, Marcel Dekker, 1996, vol. 25, No. 1 &2, pp. 23-35.

* cited by examiner

*Primary Examiner* — Stephen Rawlings
(74) *Attorney, Agent, or Firm* — Marshall, Gerstein & Borun LLP

(57) ABSTRACT

The present invention relates to pharmaceutical compositions for the treatment of an epithelial tumor in a human, said pharmaceutical composition comprising an IgG1 antibody specifically binding to human CEA, wherein the variable region of said IgG1 antibody comprises at least (i) a CDR-H1 having the amino acid sequence "SYWMH" (SEQ ID NO: 29) and a CDR-H2 having the amino acid sequence "FIRNKANGGTTEYAASVKG" (SEQ ID NO: 28) and a CDR-H3 having the amino acid sequence "DRGLRFYFDY" (SEQ ID NO: 27) or (ii) a CDR-H1 having the amino acid sequence "TYAMH" (SEQ ID NO: 31) and a CDR-H2 having the amino acid sequence "LISNDGSNKYYADSVKG" (SEQ ID NO: 30) and a CDR-H3 having the amino acid sequence "DRGLRFYFDY" (SEQ ID NO: 27). Furthermore, processes for the production of said pharmaceutical compositions as well as medical/pharmaceutical uses for the IgG1 antibody molecules bearing specificities for the human CEA antigen are disclosed.

2 Claims, 10 Drawing Sheets

SEQUENCE LISTING

<160> NUMBER OF SEQ ID NOS: 101

<210> SEQ ID NO 1
<211> LENGTH: 753
<212> TYPE: DNA
<213> ORGANISM: Homo sapiens
<220> FEATURE:
<221> NAME/KEY: MISC_FEATURE
<222> LOCATION: (1)..(753)

<223> OTHER INFORMATION: scFv A5 VH-A240VL

<400> SEQUENCE: 1

```
gaggtgcagc tgctcgagtc tgggggaggc gtggtccagc ctggagggtc cctgagactc      60
tcctgtgcag cctctggatt caccctcagt acctatgcca tgcactgggt ccgccaggct     120
ccaggcaagg ggctggagtg ggtggcactt atatcaaatg atggaagcaa taaatactat     180
gcagactccg tgaagggccg attcaccatc tccagagaca attccaagaa cacgctgtat     240
ctgcaaatga acagcctgag agctgaggac acggccgtgt attactgtgc gagagatagg     300
gggctacggt tctactttga ctactggggc caagggacca cggtcaccgt ctcctcaggt     360
ggtggtggtt ctggcggcgg cggctccggt ggtggtggtt ctgagctcgt gctgactcag     420
ccggcttccc tctctgcatc tcctggagca tcagccagtc tcacctgcac cttgcgcagg     480
ggcatcaatg ttggtgccta cagtatatac tggtaccagc agaagccagg gagtcctccc     540
cagtatctcc tgaggtacaa atcagactca gataagcagc agggctctgg agtctccagc     600
cgcttctctg catccaaaga tgcttcggcc aatgcaggga ttttactcat ctctgggctc     660
cagtctgagg atgaggctga ctattactgt atgatttggc acagcggcgc ttctgcggtg     720
ttcggcggag ggaccaagtt gaccgtccta tag                                   753
```

<210> SEQ ID NO 2
<211> LENGTH: 250
<212> TYPE: PRT
<213> ORGANISM: Homo sapiens
<220> FEATURE:
<221> NAME/KEY: MISC_FEATURE
<222> LOCATION: (1)..(250)
<223> OTHER INFORMATION: scFv A5 VH-A240VL

<400> SEQUENCE: 2

```
Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Leu Arg Phe Tyr Phe Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Glu Leu Val Leu Thr Gln Pro Ala Ser Leu
    130                 135                 140

Ser Ala Ser Pro Gly Ala Ser Ala Ser Leu Thr Cys Thr Leu Arg Arg
145                 150                 155                 160

Gly Ile Asn Val Gly Ala Tyr Ser Ile Tyr Trp Tyr Gln Gln Lys Pro
                165                 170                 175

Gly Ser Pro Pro Gln Tyr Leu Leu Arg Tyr Lys Ser Asp Ser Asp Lys
            180                 185                 190

Gln Gln Gly Ser Gly Val Ser Ser Arg Phe Ser Ala Ser Lys Asp Ala
```

```
              195                 200                 205
Ser Ala Asn Ala Gly Ile Leu Leu Ile Ser Gly Leu Gln Ser Glu Asp
    210                 215                 220

Glu Ala Asp Tyr Tyr Cys Met Ile Trp His Ser Gly Ala Ser Ala Val
225                 230                 235                 240

Phe Gly Gly Gly Thr Lys Leu Thr Val Leu
                245                 250
```

<210> SEQ ID NO 3
<211> LENGTH: 759
<212> TYPE: DNA
<213> ORGANISM: Homo sapiens
<220> FEATURE:
<221> NAME/KEY: MISC_FEATURE
<222> LOCATION: (1)..(759)
<223> OTHER INFORMATION: scFv B9 VH-A240VL

<400> SEQUENCE: 3

```
gaggtgcagc tgctcgagtc tgggggaggc ttggtccagc ctggggaggtc cctgagactc      60 tcctgtgcag cgtctggatt caccgtcagt agctactgga tgcactgggt ccgccaagct     120
ccagggaagg ggctggaatg ggtaggtttc attagaaaca agctaatgg tgggacaaca      180 gaatacgccg cgtctgtgaa aggcagattc accatctcaa gagatgattc aagaacacg      240 ctgtatcttc aaatgaacag cctgagagcc gaggacacgg ccgtgtatta ctgtgcaaga     300
gatagggggc tacggttcta ctttgactac tggggccaag ggaccacggt caccgtctcc     360
tcaggtggtg gtggttctgg cggcggcggc tccggtggtg gtggttctga gctcgtgctg     420
actcagccgg cttccctctc tgcatctcct ggagcatcag ccagtctcac ctgcaccttg     480
cgcaggggca tcaatgttgg tgcctacagt atatactggt accagcagaa gccagggagt     540
cctccccagt atctcctgag gtacaaatca gactcagata gcagcagggg ctctggagtc     600
tccagccgct ctctgcatc caaagatgct tcggccaatg cagggatttt actcatctct      660
gggctccagt ctgaggatga ggctgactat tactgtatga tttggcacag cggcgcttct     720
gcggtgttcg gcggagggac caagttgacc gtcctatag                            759
```

<210> SEQ ID NO 4
<211> LENGTH: 252
<212> TYPE: PRT
<213> ORGANISM: Homo sapiens
<220> FEATURE:
<221> NAME/KEY: MISC_FEATURE
<222> LOCATION: (1)..(252)
<223> OTHER INFORMATION: scFv B9 VH-A240VL

<400> SEQUENCE: 4

```
Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
        35                  40                  45

Gly Phe Ile Arg Asn Lys Ala Asn Gly Gly Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Ala Arg Asp Arg Gly Leu Arg Phe Tyr Phe Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Glu Leu Val Leu Thr Gln Pro Ala
        130                 135                 140

Ser Leu Ser Ala Ser Pro Gly Ala Ser Ala Ser Leu Thr Cys Thr Leu
145                 150                 155                 160

Arg Arg Gly Ile Asn Val Gly Ala Tyr Ser Ile Tyr Trp Tyr Gln Gln
                165                 170                 175

Lys Pro Gly Ser Pro Pro Gln Tyr Leu Leu Arg Tyr Lys Ser Asp Ser
        180                 185                 190

Asp Lys Gln Gln Gly Ser Gly Val Ser Ser Arg Phe Ser Ala Ser Lys
        195                 200                 205

Asp Ala Ser Ala Asn Ala Gly Ile Leu Leu Ile Ser Gly Leu Gln Ser
210                 215                 220

Glu Asp Glu Ala Asp Tyr Tyr Cys Met Ile Trp His Ser Gly Ala Ser
225                 230                 235                 240

Ala Val Phe Gly Gly Gly Thr Lys Leu Thr Val Leu
                245                 250
```

<210> SEQ ID NO 5
<211> LENGTH: 753
<212> TYPE: DNA
<213> ORGANISM: Homo sapiens
<220> FEATURE:
<221> NAME/KEY: MISC_FEATURE
<222> LOCATION: (1)..(753)
<223> OTHER INFORMATION: scFv D8 VH-A240VL

<400> SEQUENCE: 5

```
gaggtgcagc tgctcgagtc tgggggaggc gtggtccagc ctggagggtc cctgagactc      60
tcctgtgcag cctctggatt caccctcagt acctatgcca tgcactgggt ccgccaggct     120
ccaggcaagg ggctggagtg ggtggcactt atatcaaatg atggaagcaa taaatactat     180
gcagactccg tgaagggccg attcaccatc tccagagaca attccaagaa cacgctgtat     240
ctgcaaatga acagcctgag agctgaggac acggctgtgt attactgtac tagagatagg     300
gggctacggt tctactttga ctactggggc caagggacca cggtcaccgt ctcctcaggt     360
ggtggtggtt ctggcggcgg cggctccggt ggtggtggtt ctgagctcgt gctgactcag     420
ccggcttccc tctctgcatc tcctggagca tcagccagtc tcacctgcac cttgcgcagg     480
ggcatcaatg ttggtgccta cagtatatac tggtaccagc agaagccagg gagtcctccc     540
cagtatctcc tgaggtacaa atcagactca gataagcagc agggctctgg agtctccagc     600
cgcttctctg catccaaaga tgcttcggcc aatgcaggga ttttactcat ctctgggctc     660
cagtctgagg atgaggctga ctattactgt atgatttggc acagcggcgc ttctgcggtg     720
ttcggcggag ggaccaagtt gaccgtccta tag                                  753
```

<210> SEQ ID NO 6
<211> LENGTH: 250
<212> TYPE: PRT
<213> ORGANISM: Homo sapiens
<220> FEATURE:
<221> NAME/KEY: MISC_FEATURE
<222> LOCATION: (1)..(250)
<223> OTHER INFORMATION: scFv D8 VH-A240VL

<400> SEQUENCE: 6

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Arg Gly Leu Arg Phe Tyr Phe Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Glu Leu Val Leu Thr Gln Pro Ala Ser Leu
    130                 135                 140

Ser Ala Ser Pro Gly Ala Ser Ala Ser Leu Thr Cys Thr Leu Arg Arg
145                 150                 155                 160

Gly Ile Asn Val Gly Ala Tyr Ser Ile Tyr Trp Tyr Gln Gln Lys Pro
                165                 170                 175

Gly Ser Pro Pro Gln Tyr Leu Leu Arg Tyr Lys Ser Asp Ser Asp Lys
            180                 185                 190

Gln Gln Gly Ser Gly Val Ser Ser Arg Phe Ser Ala Ser Lys Asp Ala
        195                 200                 205

Ser Ala Asn Ala Gly Ile Leu Leu Ile Ser Gly Leu Gln Ser Glu Asp
    210                 215                 220

Glu Ala Asp Tyr Tyr Cys Met Ile Trp His Ser Gly Ala Ser Ala Val
225                 230                 235                 240

Phe Gly Gly Gly Thr Lys Leu Thr Val Leu
                245                 250

<210> SEQ ID NO 7
<211> LENGTH: 363
<212> TYPE: DNA
<213> ORGANISM: Mus musculus
<220> FEATURE:
<221> NAME/KEY: MISC_FEATURE
<222> LOCATION: (1)..(363)
<223> OTHER INFORMATION: Sequence of the VH chain A5B7

<400> SEQUENCE: 7
gaggtgcagc tggtcgagtc aggaggaggc ttggtacagc ctgggggttc tctgagactc      60
tcctgtgcaa cttctggggtt caccttcact gattactaca tgaactgggt ccgccagcct    120
ccaggaaagg cacttgagtg gttgggtttt attggaaaca agctaatgg ttacacaaca      180 gagtacagtg catctgtgaa ggtcggttc accatctcca gagataaatc ccaaagcatc     240
ctctatcttc aaatgaacac cctgagagct gaggacagtg ccacttatta ctgtaccaga     300 gataggggc tacggttcta ctttgactac tggggccaag gaccacggt caccgtctcc      360 tca                                                                   363

<210> SEQ ID NO 8
<211> LENGTH: 121
<212> TYPE: PRT

<213> ORGANISM: Mus musculus
<220> FEATURE:
<221> NAME/KEY: MISC_FEATURE
<222> LOCATION: (1)..(121)
<223> OTHER INFORMATION: Sequence of the VH chain A5B7

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Pro Gly Lys Ala Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Val Thr Val Ser Ser
        115                 120
```

<210> SEQ ID NO 9
<211> LENGTH: 318
<212> TYPE: DNA
<213> ORGANISM: Mus musculus
<220> FEATURE:
<221> NAME/KEY: MISC_FEATURE
<222> LOCATION: (1)..(318)
<223> OTHER INFORMATION: Sequence of the VL chain A5B7 VL

<400> SEQUENCE: 9

```
gacattgagc tcacccagtc tccagcaatc ctgtctgcat ctccagggga gaaggtcaca      60
atgacttgca gggccagctc aagtgtaact tacattcact ggtaccagca gaagccagga     120
tcctccccca atcctggat ttatgccaca tccaacctgg cttctggagt ccctgctcgc     180
ttcagtggca gtgggtctgg gacctcttac tctctcacaa tcagcagagt ggaggctgaa     240
gatgctgcca cttattactg ccaacattgg agtagtaaac caccgacgtt cggtggaggg     300
accaagctcg agatcaaa                                                    318
```

<210> SEQ ID NO 10
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: Sequence of the VL chain A5B7 VL

<400> SEQUENCE: 10

```
Asp Ile Glu Leu Thr Gln Ser Pro Ala Ile Leu Ser Ala Ser Pro Gly
1               5                   10                  15

Glu Lys Val Thr Met Thr Cys Arg Ala Ser Ser Ser Val Thr Tyr Ile
            20                  25                  30

His Trp Tyr Gln Gln Lys Pro Gly Ser Ser Pro Lys Ser Trp Ile Tyr
        35                  40                  45

Ala Thr Ser Asn Leu Ala Ser Gly Val Pro Ala Arg Phe Ser Gly Ser
    50                  55                  60
```

Gly Ser Gly Thr Ser Tyr Ser Leu Thr Ile Ser Arg Val Glu Ala Glu
65                  70                  75                  80

Asp Ala Ala Thr Tyr Tyr Cys Gln His Trp Ser Ser Lys Pro Pro Thr
                85                  90                  95

Phe Gly Gly Gly Thr Lys Leu Glu Ile Lys
            100                 105

<210> SEQ ID NO 11
<211> LENGTH: 363
<212> TYPE: DNA
<213> ORGANISM: Mus musculus
<220> FEATURE:
<221> NAME/KEY: MISC_FEATURE
<222> LOCATION: (1)..(363)
<223> OTHER INFORMATION: Sequence of the VH chain T84.66 VH

<400> SEQUENCE: 11
gaggttcagc tgcagcagtc tggggcagag cttgtggagc caggggcctc agtcaagttg      60
tcctgcacag cttctggctt caacattaaa gacacctata tgcactgggt gaagcagagg     120
cctgaacagg gcctggaatg gattggaagg attgatcctg cgaatggtaa tagtaaatat     180
gtcccgaagt tccagggcaa ggccactata acagcagaca catcctccaa cacagcctac     240
ctgcagctca ccagcctgac atctgaggac actgccgtct attattgtgc tccgtttggt     300
tactacgtgt ctgactatgc tatggcctac tggggtcaag aacctcagt caccgtctcc     360 tcc                                                                  363

<210> SEQ ID NO 12
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: Sequence of the VH chain T84.66 VH

<400> SEQUENCE: 12

Glu Val Gln Leu Gln Gln Ser Gly Ala Glu Leu Val Glu Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Ser Lys Tyr Val Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Ser Val Thr Val Ser Ser
        115                 120

<210> SEQ ID NO 13
<211> LENGTH: 333
<212> TYPE: DNA
<213> ORGANISM: Mus musculus
<220> FEATURE:
<221> NAME/KEY: MISC_FEATURE
<222> LOCATION: (1)..(333)
<223> OTHER INFORMATION: Sequence of the VL chain T84.66 VL

<400> SEQUENCE: 13

```
gacattgtgc tgacccaatc tccagcttct ttggctgtgt ctcttgggca gagggccacc      60
atgtcctgca gagccggtga aagtgttgat atttttggcg ttgggttttt gcactggtac     120
cagcagaaac caggacagcc acccaaactc ctcatctatc gtgcatccaa cctagaatct     180
gggatccctg tcaggttcag tggcactggg tctaggacag acttcaccct catcattgat     240
cctgtggagg ctgatgatgt tgccacctat tactgtcagc aaactaatga ggatccgtac     300
acgttcggag gggggaccaa gctcgagata aaa                                  333
```

<210> SEQ ID NO 14
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: Sequence of the VL chain T84.66 VL

<400> SEQUENCE: 14

```
Asp Ile Val Leu Thr Gln Ser Pro Ala Ser Leu Ala Val Ser Leu Gly
 1               5                  10                  15
Gln Arg Ala Thr Met Ser Cys Arg Ala Gly Glu Ser Val Asp Ile Phe
            20                  25                  30
Gly Val Gly Phe Leu His Trp Tyr Gln Gln Lys Pro Gly Gln Pro Pro
        35                  40                  45
Lys Leu Leu Ile Tyr Arg Ala Ser Asn Leu Glu Ser Gly Ile Pro Val
    50                  55                  60
Arg Phe Ser Gly Thr Gly Ser Arg Thr Asp Phe Thr Leu Ile Ile Asp
65                  70                  75                  80
Pro Val Glu Ala Asp Asp Val Ala Thr Tyr Tyr Cys Gln Gln Thr Asn
                85                  90                  95
Glu Asp Pro Tyr Thr Phe Gly Gly Gly Thr Lys Leu Glu Ile Lys
            100                 105                 110
```

<210> SEQ ID NO 15
<211> LENGTH: 360
<212> TYPE: DNA
<213> ORGANISM: Mus musculus
<220> FEATURE:
<221> NAME/KEY: MISC_FEATURE
<222> LOCATION: (1)..(360)
<223> OTHER INFORMATION: Sequence of the VH chain MFE-23 VH

<400> SEQUENCE: 15

```
caggttaagc tgcagcagtc tggggcagag cttgtgagat cagggacatc agtcaagttg      60
tcctgcacag cttctggctt caacattaaa gactcctata tgcactggct gaggcagggg     120
cctgaacagg gcctggagtg gattggatgg attgatcctg agaatggtga tactgaatat     180
gccccgaagt tccagggcaa ggccactttc actactgaca catcctccaa cacagcctac     240
ctgcagctca gcagcctgac atctgaggac actgccgtct attactgtaa cgagggcaca     300
cctacagggc cttactactt tgactactgg ggccaaggca ccactgtcac agtctcctcc     360
```

<210> SEQ ID NO 16
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: Sequence of the VH chain MFE-23 VH

<400> SEQUENCE: 16

Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
                20                  25                  30

Tyr Met His Trp Leu Arg Gln Gly Pro Glu Gln Gly Leu Glu Trp Ile
            35                  40                  45

Gly Trp Ile Asp Pro Glu Asn Gly Asp Thr Glu Tyr Ala Pro Lys Phe
        50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Thr Val Thr Val Ser Ser
        115                 120

<210> SEQ ID NO 17
<211> LENGTH: 318
<212> TYPE: DNA
<213> ORGANISM: Mus musculus
<220> FEATURE:
<221> NAME/KEY: MISC_FEATURE
<222> LOCATION: (1)..(318)
<223> OTHER INFORMATION: Sequence of the VL chain MFE-23 VL

<400> SEQUENCE: 17
gagaacgttc tcacccagtc tccagcaatc atgtctgcat ctccagggga gaaggtcacc      60
atcacctgca gtgccagctc aagcgtcagc tacatgcact ggttccagca gaagccaggc     120
acctccccca aactctggat ttattctaca tccaacctgg cttctggagt ccctgctcgc     180
ttctctggca gtgggtctgg gacctcttac tctctcacaa tcagcagaat ggaggctgaa     240
gatgctgcca cttattactg ccagcagaga agtagttacc cactcacgtt cggtgctggg     300
accaagctcg agctgaaa                                                   318

<210> SEQ ID NO 18
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: Sequence of the VL chain MFE-23 VL

<400> SEQUENCE: 18

Glu Asn Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

```
Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105

<210> SEQ ID NO 19
<211> LENGTH: 357
<212> TYPE: DNA
<213> ORGANISM: Homo sapiens
<220> FEATURE:
<221> NAME/KEY: MISC_FEATURE
<222> LOCATION: (1)..(357)
<223> OTHER INFORMATION: Sequence of the VH chain A5 VH

<400> SEQUENCE: 19
gaggtgcagc tggtcgagtc tgggggaggc gtggtccagc ctggagggtc cctgagactc     60
tcctgtgcag cctctggatt caccctcagt acctatgcca tgcactgggt ccgccaggct    120
ccaggcaagg ggctggagtg ggtggcactt atatcaaatg atggaagcaa taaatactat    180
gcagactccg tgaagggccg attcaccatc tccagagaca attccaagaa cacgctgtat    240
ctgcaaatga acagcctgag agctgaggac acggccgtgt attactgtgc gagagatagg    300
gggctacggt tctactttga ctactggggc caagggacca cggtcaccgt ctcctca       357

<210> SEQ ID NO 20
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: Sequence of the VH chain A5 VH

<400> SEQUENCE: 20

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Leu Arg Phe Tyr Phe Asp Tyr Trp Gly Gln Gly
            100                 105                 110

Thr Thr Val Thr Val Ser Ser
        115

<210> SEQ ID NO 21
<211> LENGTH: 363
<212> TYPE: DNA
<213> ORGANISM: Homo sapiens
<220> FEATURE:
<221> NAME/KEY: MISC_FEATURE
<222> LOCATION: (1)..(363)
<223> OTHER INFORMATION: Sequence of the VH chain B9 VH
```

<400> SEQUENCE: 21

```
gaggtgcagc tggtcgagtc tgggggaggc ttggtccagc ctgggaggtc cctgagactc    60
tcctgtgcag cgtctggatt caccgtcagt agctactgga tgcactgggt ccgccaagct   120
ccagggaagg ggctggaatg ggtaggtttc attagaaaca aagctaatgg tgggacaaca   180
gaatacgccg cgtctgtgaa aggcagattc accatctcaa gagatgattc caagaacacg   240
ctgtatcttc aaatgaacag cctgagagcc gaggacacgg ccgtgtatta ctgtgcaaga   300 gataggggc tacggttcta ctttgactac tggggccaag gaccacggt caccgtctcc    360 tca                                                                363
```

<210> SEQ ID NO 22
<211> LENGTH: 121
<212> TYPE: PRT
<213> ORGANISM: Homo sapiens
<220> FEATURE:
<221> NAME/KEY: MISC_FEATURE
<222> LOCATION: (1)..(121)
<223> OTHER INFORMATION: Sequence of the VH chain B9 VH

<400> SEQUENCE: 22

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
        35                  40                  45

Gly Phe Ile Arg Asn Lys Ala Asn Gly Gly Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
            100                 105                 110

Gln Gly Thr Thr Val Thr Val Ser Ser
        115                 120
```

<210> SEQ ID NO 23
<211> LENGTH: 357
<212> TYPE: DNA
<213> ORGANISM: Homo sapiens
<220> FEATURE:
<221> NAME/KEY: MISC_FEATURE
<222> LOCATION: (1)..(357)
<223> OTHER INFORMATION: Sequence of the VH chain D8 VH

<400> SEQUENCE: 23

```
gaggtgcagc tggtcgagtc tgggggaggc gtggtccagc ctgggaggtc cctgagactc    60
tcctgtgcag cctctggatt caccctcagt acctatgcca tgcactgggt ccgccaggct   120
ccaggcaagg ggctggagtg ggtggcactt atatcaaatg atggaagcaa taaatactat   180
gcagactccg tgaagggccg attcaccatc tccagagaca attccaagaa cacgctgtat   240
ctgcaaatga acagcctgag agctgaggac acggctgtgt attactgtac tagagatagg   300
gggctacggt tctactttga ctactggggc caagggacca cggtcaccgt ctcctca      357
```

<210> SEQ ID NO 24
<211> LENGTH: 119

```
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: Sequence of the VH chain D8 VH

<400> SEQUENCE: 24
```

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Arg Gly Leu Arg Phe Tyr Phe Asp Tyr Trp Gly Gln Gly
            100                 105                 110

Thr Thr Val Thr Val Ser Ser
        115

```
<210> SEQ ID NO 25
<211> LENGTH: 348
<212> TYPE: DNA
<213> ORGANISM: Homo sapiens
<220> FEATURE:
<221> NAME/KEY: MISC_FEATURE
<222> LOCATION: (1)..(348)
<223> OTHER INFORMATION: Sequence of the VL chain A240VL

<400> SEQUENCE: 25
```
caggccgtgc tgactcagcc ggcttccctc tctgcatctc ctggagcatc agccagtctc      60
acctgcacct tgcgcagggg catcaatgtt ggtgcctaca gtatatactg gtaccagcag     120
aagccaggga gtcctcccca gtatctcctg aggtacaaat cagactcaga taagcagcag     180
ggctctggag tctccagccg cttctctgca tccaaagatg cttcggccaa tgcaggga tt    240 ttactcatct ctgggctcca gtctgaggat gaggctgact attactgtat gatttggcac     300
agcggcgctt ctgcggtgtt cggcggaggg accaagttga ccgtccta                  348

```
<210> SEQ ID NO 26
<211> LENGTH: 116
<212> TYPE: PRT
<213> ORGANISM: Homo sapiens
<220> FEATURE:
<221> NAME/KEY: MISC_FEATURE
<222> LOCATION: (1)..(116)
<223> OTHER INFORMATION: Sequence of the VL chain A240VL

<400> SEQUENCE: 26
```

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val

```
                 50                  55                  60
Ser Ser Arg Phe Ser Ala Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Met Ile Trp His Ser Gly Ala Ser Ala Val Phe Gly Gly Gly Thr Lys
            100                 105                 110

Leu Thr Val Leu
        115

<210> SEQ ID NO 27
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Sequence of CDRs (CDR-H3 A5B7)

<400> SEQUENCE: 27

Asp Arg Gly Leu Arg Phe Tyr Phe Asp Tyr
1               5                   10

<210> SEQ ID NO 28
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Sequence of CDRs (CDR-H2 B9)

<400> SEQUENCE: 28

Phe Ile Arg Asn Lys Ala Asn Gly Gly Thr Thr Glu Tyr Ala Ala Ser
1               5                   10                  15

Val Lys Gly

<210> SEQ ID NO 29
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Sequence of CDRs (CDR-H1 B9)

<400> SEQUENCE: 29

Ser Tyr Trp Met His
1               5

<210> SEQ ID NO 30
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Sequence of CDRs (CDR-H2 A5/D8)

<400> SEQUENCE: 30

Leu Ile Ser Asn Asp Gly Ser Asn Lys Tyr Tyr Ala Asp Ser Val Lys
1               5                   10                  15

Gly
```

```
<210> SEQ ID NO 31
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Sequence of CDRs (CDR-H1 A5/D8)

<400> SEQUENCE: 31

Thr Tyr Ala Met His
1               5

<210> SEQ ID NO 32
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: Sequence of CDRs (CDR-L3 A240)

<400> SEQUENCE: 32

Met Ile Trp His Ser Gly Ala Ser Ala Val
1               5                   10

<210> SEQ ID NO 33
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: Sequence of CDRs (CDR-L2 A240)

<400> SEQUENCE: 33

Tyr Lys Ser Asp Ser Asp Lys Gln Gln Gly Ser
1               5                   10

<210> SEQ ID NO 34
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: Sequence of CDRs (CDR-L1 A240)

<400> SEQUENCE: 34

Thr Leu Arg Arg Gly Ile Asn Val Gly Ala Tyr Ser Ile Tyr
1               5                   10

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaattcgcca ccatggagtc tccctcggcc cc                                32

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 36
gtcgacctat atcagagcaa cccc                                         24

<210> SEQ ID NO 37
<211> LENGTH: 702
<212> TYPE: PRT
<213> ORGANISM: Homo sapiens
<220> FEATURE:
<221> NAME/KEY: MISC_FEATURE
<222> LOCATION: (1)..(702)
<223> OTHER INFORMATION: Sequence of Homo sapiens carcinoembryonic
      antigen-related cell adhesion molecule 5 (CEACAM5)

<400> SEQUENCE: 37

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

```
Glu Pro Pro Lys Pro Phe Ile Thr Ser Asn Asn Ser Asn Pro Val Glu
            325                 330                 335

Asp Glu Asp Ala Val Ala Leu Thr Cys Glu Pro Glu Ile Gln Asn Thr
        340                 345                 350

Thr Tyr Leu Trp Trp Val Asn Asn Gln Ser Leu Pro Val Ser Pro Arg
    355                 360                 365

Leu Gln Leu Ser Asn Asp Asn Arg Thr Leu Thr Leu Leu Ser Val Thr
370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
    690                 695                 700
```

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gagccgcacg agcccgagct ccagatgacc cagtctcc                                   38

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gagccgcacg agcccgagct cgtgatgacy cagtctcc                                   38

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gagccgcacg agcccgagct cgtgwtgacr cagtctcc                                   38

<210> SEQ ID NO 41
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gagccgcacg agcccgagct cacactcacg cagtctcc                                   38

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gagccgcacg agcccgagct cgtgctgact cagtctcc                                   38

<210> SEQ ID NO 43
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gacgacacta gttgcagcca ccgtacgttt gatttccacc ttggtcc                         47

<210> SEQ ID NO 44
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gacgacacta gttgcagcca ccgtacgttt gatctccasc ttggtcc        47

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gacgacacta gttgcagcca ccgtacgttt gatatccact ttggtcc        47

<210> SEQ ID NO 46
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gacgacacta gttgcagcca ccgtacgttt aatctccagt cgtgtcc        47

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gagccgcacg agcccgagct cgtgttgacg cagccgccct c        41

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gagccgcacg agcccgagct cgtgctgact cagccaccct c        41

<210> SEQ ID NO 49
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gagccgcagg agcccgagct cgccctgact cagcctscct ccgt        44

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 50
acctgcgagc tcgtgctgac tcarycmycc tctgc                35

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acctgcgagc tcgtgctgac tcagccrsct tcc                  33

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acctgcgagc tcatgctgac tcagccccac tc                   32

<210> SEQ ID NO 53
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gagccgcacg agcccgagct cgwgctgact cagccaccyt c         41

<210> SEQ ID NO 54
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gagccgcacg agcccgagct cgtggtgacy caggagccmt c         41

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cgtgggacta gtcttgggct gacctaggac ggt                  33

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cgtgggacta gtcttgggct gaccgaggac ggt                                33

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtcacactcg agtcaggagg aggcttggta c                                  31

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtcacaggtg accgtggtcc cttggcccca g                                  31

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Gly Asp Tyr Lys Asp Asp Asp Asp Lys
1               5                   10

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aggtgcagct gctcgagtct gg                                            22

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
caggtgcagc tgctcgagtc ggg                                           23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
caggtgcagc tactcgagtg ggg					23

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ctgaggagac ggtgacc					17

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ctgaagagac ggtgacc					17

<210> SEQ ID NO 65
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gtagtcaaag tagaaccgta gccccctatc tctygcacag taatacacgg c					51

<210> SEQ ID NO 66
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtagtcaaag tagaaccgta gccccctatc tctygcacag taatacayrg c					51

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(34)
<223> OTHER INFORMATION: a, c, g, or t

<400> SEQUENCE: 67
gtagtcaaag tagaaccgta gccccctatc tctngyacag taatacacrg c					51

<210> SEQ ID NO 68
<211> LENGTH: 51
<212> TYPE: DNA
<213> ORGANISM: Artificial Sequence
<220> FEATURE:
<223> OTHER INFORMATION: Description of Artificial Sequence: Synthetic

```
      primer
<220> FEATURE:
<221> NAME/KEY: modified_base
<222> LOCATION: (34)..(34)
<223> OTHER INFORMATION: a, c, g, or t

<400> SEQUENCE: 68
gtagtcaaag tagaaccgta gccccctatc tctngcacag taatacaarg c          51

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtagtcaaag tagaaccgta gccccctatc tctsgcacag taatacacrg c          51

<210> SEQ ID NO 70
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cgagacggtg accgtggtcc cttggcccca gtagtcaaag tagaaccgta gcc        53

<210> SEQ ID NO 71
<211> LENGTH: 451
<212> TYPE: PRT
<213> ORGANISM: Mus musculus
<220> FEATURE:
<221> NAME/KEY: MISC_FEATURE
<222> LOCATION: (1)..(451)
<223> OTHER INFORMATION: A5B7 HC

<400> SEQUENCE: 71
```

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Pro Gly Lys Ala Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala

```
                165                 170                 175
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 72
<211> LENGTH: 213
<212> TYPE: PRT
<213> ORGANISM: Mus musculus
<220> FEATURE:
<221> NAME/KEY: MISC_FEATURE
<222> LOCATION: (1)..(213)
<223> OTHER INFORMATION: A5B7 LC

<400> SEQUENCE: 72

Asp Ile Glu Leu Thr Gln Ser Pro Ala Ile Leu Ser Ala Ser Pro Gly
1               5                   10                  15

Glu Lys Val Thr Met Thr Cys Arg Ala Ser Ser Ser Val Thr Tyr Ile
            20                  25                  30

His Trp Tyr Gln Gln Lys Pro Gly Ser Ser Pro Lys Ser Trp Ile Tyr
        35                  40                  45

Ala Thr Ser Asn Leu Ala Ser Gly Val Pro Ala Arg Phe Ser Gly Ser
    50                  55                  60
```

```
Gly Ser Gly Thr Ser Tyr Ser Leu Thr Ile Ser Arg Val Glu Ala Glu
 65                  70                  75                  80

Asp Ala Ala Thr Tyr Tyr Cys Gln His Trp Ser Ser Lys Pro Pro Thr
                 85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 73
<211> LENGTH: 451
<212> TYPE: PRT
<213> ORGANISM: Mus musculus
<220> FEATURE:
<221> NAME/KEY: MISC_FEATURE
<222> LOCATION: (1)..(451)
<223> OTHER INFORMATION: T84.66 HC

<400> SEQUENCE: 73

Glu Val Gln Leu Gln Gln Ser Gly Ala Glu Leu Val Glu Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Ser Lys Tyr Val Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 74
<211> LENGTH: 218
<212> TYPE: PRT
<213> ORGANISM: Mus musculus

<400> SEQUENCE: 74

Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95

Glu Asp Pro Tyr Thr Phe Gly Gly Gly Thr Lys Leu Glu Ile Lys Arg
                100                 105                 110
```

Ala Asp Ala Ala Pro Thr Val Ser Ile Phe Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
        210                 215

<210> SEQ ID NO 75
<211> LENGTH: 450
<212> TYPE: PRT
<213> ORGANISM: Mus musculus

<400> SEQUENCE: 75

Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu

```
                260                 265                 270
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 76
<211> LENGTH: 213
<212> TYPE: PRT
<213> ORGANISM: Mus musculus

<400> SEQUENCE: 76

Glu Asn Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175
```

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
            210

<210> SEQ ID NO 77
<211> LENGTH: 449
<212> TYPE: PRT
<213> ORGANISM: Homo sapiens

<400> SEQUENCE: 77

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Gly Leu Arg Phe Tyr Phe Asp Tyr Trp Gly Gln Gly
        100                 105                 110

Thr Thr Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

```
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 78
<211> LENGTH: 451
<212> TYPE: PRT
<213> ORGANISM: Homo sapiens

<400> SEQUENCE: 78

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
            35                  40                  45

Gly Phe Ile Arg Asn Lys Ala Asn Gly Gly Thr Thr Glu Tyr Ala Ala
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 79
<211> LENGTH: 449
<212> TYPE: PRT
<213> ORGANISM: Homo sapiens

<400> SEQUENCE: 79

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Arg Gly Leu Arg Phe Tyr Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
            165                 170                 175
Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 80
<211> LENGTH: 222
<212> TYPE: PRT
<213> ORGANISM: Homo sapiens

<400> SEQUENCE: 80

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
```

```
                     85                  90                  95
Met Ile Trp His Ser Gly Ala Ser Ala Val Phe Gly Gly Thr Lys
                100                 105                 110

Leu Thr Val Leu Gly Gln Pro Lys Ala Ala Pro Ser Val Thr Leu Phe
            115                 120                 125

Pro Pro Ser Ser Glu Glu Leu Gln Ala Asn Lys Ala Thr Leu Val Cys
        130                 135                 140

Leu Ile Ser Asp Phe Tyr Pro Gly Ala Val Thr Val Ala Trp Lys Ala
145                 150                 155                 160

Asp Ser Ser Pro Val Lys Ala Gly Val Glu Thr Thr Thr Pro Ser Lys
                165                 170                 175

Gln Ser Asn Asn Lys Tyr Ala Ala Ser Ser Tyr Leu Ser Leu Thr Pro
            180                 185                 190

Glu Gln Trp Lys Ser His Lys Ser Tyr Ser Cys Gln Val Thr His Glu
        195                 200                 205

Gly Ser Thr Val Glu Lys Thr Val Ala Pro Thr Glu Cys Ser
    210                 215                 220
```

<210> SEQ ID NO 81
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
ttctctcctt aggtgtccac tccgacattg agctcaccca gtctcc           46

<210> SEQ ID NO 82
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
catgcactcg agcttggtcc ctccaccgaa cgtc                         34

<210> SEQ ID NO 83
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
ttctctcctt aggtgtccac tccgacattg tgctgaccca atctcc           46

<210> SEQ ID NO 84
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
catgcactcg agcttggtcc ccccaccgaa cgtg                         34

-continued

```
<210> SEQ ID NO 85
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ttctctcctt aggtgtccac tccgagaacg ttctcaccca gtctcc          46

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
catgcactcg agcttggtcc cagcaccgaa cgtg                        34

<210> SEQ ID NO 87
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ttctctcctt aggtgtccac tcccaggtcc aactgcagga gtcagg          46

<210> SEQ ID NO 88
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gactcacctg aggagacggt gaccgtggtc ccttgg                     36

<210> SEQ ID NO 89
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ttctctcctt aggtgtccac tccgaggttc agctgcagca gtctgg          46

<210> SEQ ID NO 90
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gactcacctg aggagacggt gactgaggtt ccttgacc                   38

<210> SEQ ID NO 91
```

```
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ttctctcctt aggtgtccac tcccaggtta agctgcagca gtctcc          46

<210> SEQ ID NO 92
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gactcacctg aggagactgt gacagtggtg ccttgg                     36

<210> SEQ ID NO 93
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ttctctcctt aggtgtccac tcccaggccg tgctgactca gccggc          46

<210> SEQ ID NO 94
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gccttgggct gacctaggac ggtcaacttg gtcc                       34

<210> SEQ ID NO 95
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gttgaccgtc ctaggtcagc ccaaggctgc cccctcg                    37

<210> SEQ ID NO 96
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gacgtagcgg ccgcgtcgac ctatgaacat tctgtagggg c               41

<210> SEQ ID NO 97
<211> LENGTH: 43
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97 ttctctccstt aggtgtccac tccgaggtgc agctggtcga gtc                       43

<210> SEQ ID NO 98
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gactcacctg aggagacggt gaccgtggtc ccttgg                               36

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid

<400> SEQUENCE: 99

Asp Xaa Xaa Xaa Xaa Phe Tyr Phe Asp Tyr
1               5                   10

<210> SEQ ID NO 100
<211> LENGTH: 4
<212> TYPE: PRT
<213> ORGANISM: Mus musculus

<400> SEQUENCE: 100

Arg Gly Leu Arg
1

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      primer

<400> SEQUENCE: 101

His His His His His His
1               5
```

PHARMACEUTICAL ANTIBODY COMPOSITIONS WITH RESISTANCE TO SOLUBLE CEA

Figure 1:
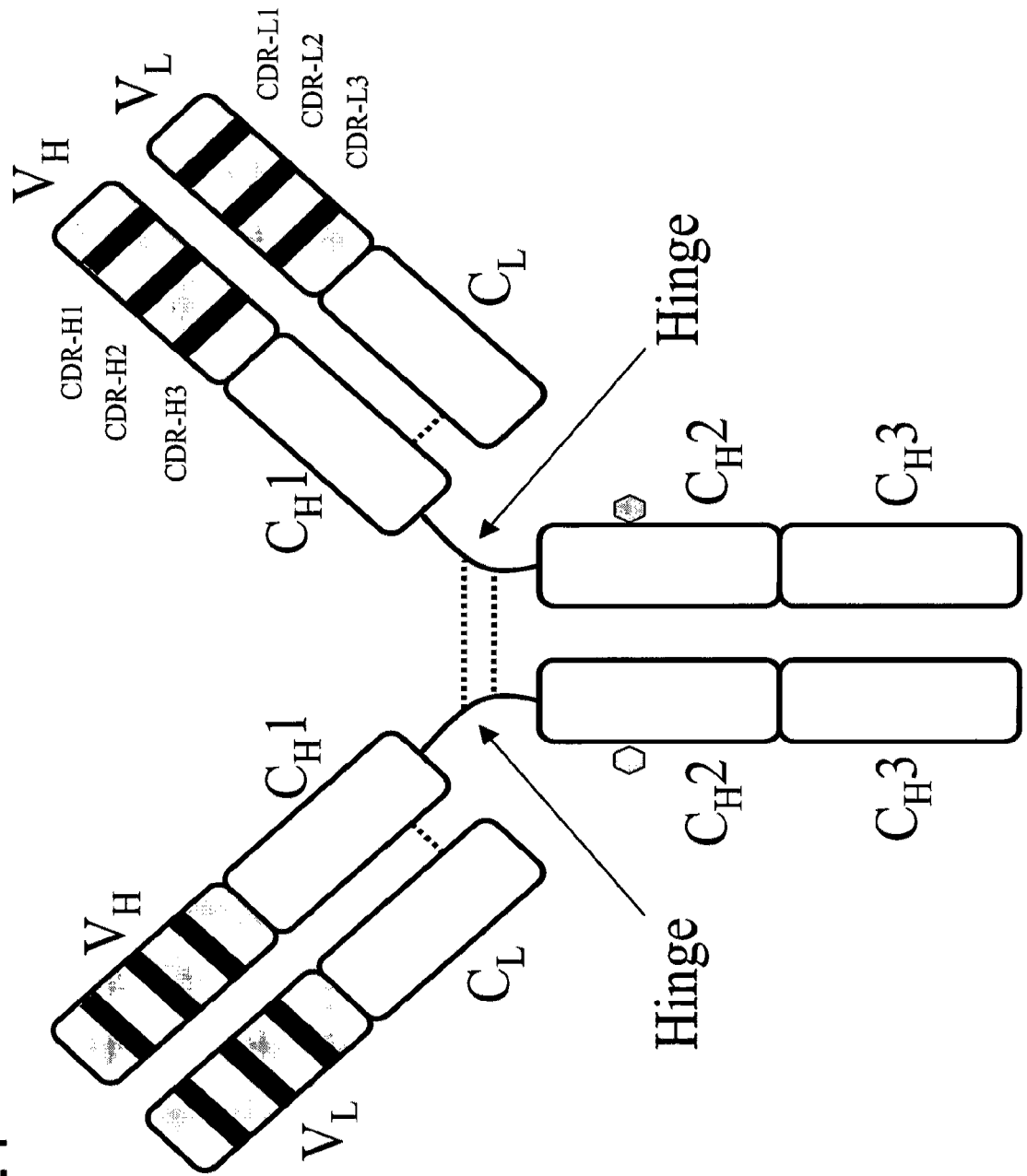

The present application is a continuation of U.S. Ser. No. 12/095,952, filed Jul. 30, 2008, now abandoned, which is a national stage filing under 35 U.S.C. §371 of PCT Application No.: PCT/US2006/012409, filed on Dec. 21, 2006, which claims priority to EP 05028063.5 filed on Dec. 21, 2005, and which claims priority to U.S. Ser. No. 60/752,029 filed on Dec. 21, 2005; and all of the disclosures of which are incorporated herein by reference in their entirety.

More than three decades have passed since Gold and Freedman first described the tumor associated carcinoembryonic antigen (CEA) in human colon cancer tissue extracts (Gold and Freedman; J. Exp. Med. 122 (1965); 467-481).

Meanwhile, 28 other genes/pseudogenes relating to the CEA gene family have been discovered. In an attempt to simplify the nomenclature used for the members of the CEA gene family, the family has recently been renamed the "CEA-related cellular adhesion molecules" (CEACAMs) and the nomenclature for its members has been unified (Beauchemin, Exp. Cell Res. 252 (1999), 243-249). For example, according to this nomenclature, human CEA (CD66e) is termed CEACAM5.

The human CEA gene family is clustered on chromosome 19q13.2 (Olsen et al. Genomics 23 (1994); 659-668). Its 29 genes and pseudogenes can be divided into three subgroups, i.e. the CEA subgroup containing seven expressed genes, the pregnancy-specific-glycoprotein (PSG) subgroup containing eleven expressed genes and the third subgroup which contains only pseudogenes (Hammarstrom, Sem. Cancer Biol. 9 (1999), 67-81; Beauchemin, Exp. Cell Res. 252 (1999), 243-249). The analysis of the amino acid sequences of CEA and the other family members revealed that they belong to the immunoglobulin (Ig) superfamily (Williams and Barclay, Annul. Rev. Immunol. 6 (1988), 381-405). All members of the CEA subgroup are attached to the cell surface membrane: Biliary glycoprotein (CEACAM1; BGP1; TM-CEA; CD66a), CEA gene family member 1 (CEACAM3; CGM1; CD66d) and CEA gene family member 7 (CEACAM4; CGM7) have hydrophobic transmembrane domains, whereas carcinoembryonic antigen (carcinoembryonic antigen-related cell adhesion molecule 5; CEACAM5; CEA; CD66e), non-specific cross-reacting antigen (CEACAM6; NCA; NCA-50/90; CD66c), CEA gene family member 2 (CEACAM7; CGM2) and CEA gene family member 6 (CEACAM8; CGM6; CD66b) are linked to the plasma membrane by glycosylphosphatidylinositol (GPI) lipid moieties. The CEA proteins are highly glycosylated with a molecular weight of up to approximately 300 kDa, depending on the number of Ig domains.

As regards the biological activity of the CEA proteins, in vitro studies with tumor cell lines suggested that several CEA subfamilies including biliary glycoprotein, CEA and non-specific cross-reacting antigen can act as homophilic and heterotypic cell adhesion molecules when expressed on the tumor cell surface (Oikawa et al., Biochem. Biophys. Res. Commun. 186 (1992), 881-887; Zhou et al., Cancer Res. 53 (1993), 3817-3822). More recently, a possible role of CEA and non-specific cross-reacting antigen in the innate immune defense protecting colon from microbial attack has been discussed (Hammarstrom and Baranov, Trends Microbiol. 9 (2001), p. 119-125). In particular, it has been proposed that these proteins bind and trap microorganisms preventing them from reaching and invading the epithelial cells of the microvilli.

It was hypothesized that CEA is an oncofetal antigen which is expressed during fetal life, absent in the healthy adult and re-expressed in cancer. However, CEA is also expressed in normal adult tissue. For instance, biliary glycoprotein, CEA, non-specific cross-reacting antigen and CEA gene family member 2 are expressed in normal human colon, particularly in the mature columnar epithelial cells facing the gut lumen and in the highly differentiated cells at the crypt mouth (Frängsmyr et al., Cancer Res. 55 (1995), 2963-2967; Frangsmyr et al., Tumor Biol. 20 (1999), 277-292). More specifically, these proteins are localized to the brush-border glycocalyx of the mature colonocytes lining the free luminal surface. Biliary glycoprotein, CEA and non-specific cross-reacting antigen are also expressed in a number of tumors of epithelial origin (Hammarström, Sem. Cancer Biol. 9 (1999), 67-81; Shively and Beatty CRC Crit. Rev. Oncol. Hematol. 2 (1985), 355-399).

Already in the late 1970s and early 1980s, CEA became a favored target antigen for radioimmunolocalization of colorectal and other epithelial tumors. This is due to the fact that CEA is overexpressed in 95% of gastrointestinal and pancreatic cancers, as well as in most small-cell and non-small-cell lung carcinomas. It is also expressed in breast carcinoma and squamous cell carcinoma of the head and neck (Primus et al., Cancer 42 (1978), 1540-1545). In fact, CEA is one of the most extensively used clinical tumor markers. It is used as a serum tumor marker for colorectal and some other cancers due to its stability, its fairly restricted expression in normal adult tissue and its high expression in tumors of epithelial origin. The bulk of CEA in a healthy individual is produced in colon. There it is released from the apical surface of mature columnar cells into the gut lumen and disappears with the feces. Thus, only very low levels are normally seen in the blood from healthy individuals. For instance, CEA levels in the blood of healthy individuals is less than 2 µg/l. In contrast, CEA levels in serum from patients with colorectal and other carcinomas are increased, ranging up to more than 2000 µg/l (Thomson et al., PNAS 64 (1969), 161-167). In particular, progressive, malignant, or late stage epithelial tumors are frequently accompanied by high serum concentrations of soluble CEA (Fletcher; Ann. Intern. Med. 104 (1986), 66-73). It is known that components from the plasma membrane, including CEA, are continually exfoliated from the surface as plasma membrane-derived vesicles (Taylor and Black, J. Natl. Cancer Inst. 74 (1985), 859-866; Sack et al., J Clin Invest. 82 (1988), 586-93) which through draining lymph and blood vessels can end up in the blood. As the tumor size increases, more CEA will accumulate in the blood. The main use of serum CEA determinations as a tumor marker is in the post-surgical surveillance of colon cancer. Increased CEA levels was the first indicator of recurrent disease in 81% (Minton et al., Cancer 55 (1985), 1284-1290) and 89% (Wanebo et al., Surg. Gynecol. Obstet. 169 (1989), 479-487) of patients, respectively. Serum CEA levels can also be used as a prognostic indicator (Mulcahy and Benson, Curr. Oncol. Rep. 1 (1999), 168-172).

Due to its over-expression in many epithelial cancers CEA is not only used as a tumor marker but also as a target for anti-tumor therapy. For example, gastrointestinal cancers account for a large proportion of human epithelial tumors, with an estimated 21.700 new cases of gastric cancer and 135.400 new cases of colorectal cancer in the United States in the year 2001 (Greenlee; CA Cancer J Clin 51 (2001), 15-36). Colorectal cancer is the third most common malignancy and the third leading cause of death from cancer in both males and females (Ries; Cancer 88 (2000), 2398-2424). In an attempt to find new therapeutics against these tumors, anti-CEA monoclonal antibodies have been explored as possible therapeutics for CEA-positive cancers (Murakami et al., Immunol. Invest. 25 (1996), 23-35).

One example for an approach in which patients with low tumor load (corresponding to low serum CEA levels) have been successfully treated is a study performed by Behr et al. In this approach, a $^{131}$I-labeled variant of labetuzumab (labetuzumab is a humanized form of anti-CEA monoclonal antibody MN-14; Behr et al., Cancer, 94: 1373-1381, (2002), 1559-64) has been analysed in a phase II trial in which 30 CRC patients with small volume metastatic disease chemorefractory to 5-fluorouracil and folinic acid or in an adjuvant setting after liver metastasis have been enrolled. A single injection of $^{131}$I-labeled labetuzumab was given. Of 19 assessable patients, 3 had partial remissions and eight showed minor responses up to 15 months in duration. In the adjuvant setting, 7 of 9 patients were disease free for up to 3 years, whereas the relapse rate in the control group was 67% in the same time period. The serum CEA levels of the patients ranged from 3.9-45 ng/ml (Behr et al., Cancer, 94: 1373-1381, 2002). In another study characterized by patients with low CEA serum levels (<5 ng/ml), CEA radio-immunotherapy with $^{131}$I-labetuzumab (loc. cit.) has been shown to improve survival post salvage resection of colorectal cancer metastases in the liver. 23 patients received a dose of 40-60 mCi/m$^2$ $^{131}$I-labetuzumab. Five-year survival was 51.3% for treated and 7.4% for control groups, respectively (Liersch et al., JCO, 2005, ASCO Proc, Vol 23, No 16S: 3627).

Yet, therapeutic approaches dealing with high serum CEA concentrations frequently resulted in low or no anti-tumor responses. For example, Wong (Clin. Cancer Res. 6 (2000): 3855-3863) used a genetically engineered $^{90}$Y labeled human/murine chimeric IgG T84.66 antibody with high affinity specificity to CEA in a phase I radioimmunotherapy trial in order to evaluate said antibody in patients with metastatic CEA-producing malignancies. 22 patients received one treatment cycle (only 3 patients had 2-3 cycles) consisting of a diagnostic administration of $^{111}$In labeled antibody followed by $^{90}$Y labeled chimeric antibody. No major anti-tumor responses could be found. 16 patients generated human anti-chimeric antibodies (HACAs). The range of soluble CEA levels in the patients enrolled in this study was 14.8-1027 ng/ml (median 97 ng/ml). In a follow-up study, the same antibody was used in a combination therapy with 5-Fluorouracil (5-FU). In this Phase I combination trial, 21 patients with chemotherapy-refractory metastatic colorectal cancer received 5-FU and $^{90}$Y-cT84.66. No objective responses were observed. The mean serum CEA level was 227.4 ng/ml, ranging from <2.5-1305 ng/ml (Wong, Clin Cancer Res, 9 (2003): 5842-5852). In another study by Najjar et al., iodine-131-labeled humanized MN-14 anti-CEA monoclonal antibody has been evaluated in patients with metastatic gastrointestinal and colorectal cancer. In this phase I trial, 21 patients either after prior external beam radiation or after standard chemotherapy have been treated with antibody. 7 of 21 patients had human anti-human antibodies (HAHAs), but no adverse effects. No antitumor response was observed. Again it has been found that elevated plasma CEA levels prevent a therapeutic effect of anti-CEA antibody approaches (Najjar et al., Clin Colorectal Cancer, 2 (2002), 31-42).

In view of the problems set forth above, the provision of means and methods for efficient therapeutics for progressive, malignant, or late stage epithelial tumors is highly desirable.

Accordingly, one aspect of the invention relates to a pharmaceutical composition for the treatment of an epithelial tumor in a human, said pharmaceutical composition comprising an IgG1 antibody specifically binding to human CEA, wherein the variable region of said IgG1 antibody comprises at least the amino acid sequences selected from the group consisting of:

(a) a CDR-H1 having the amino acid sequence "SYWMH" (SEQ ID NO. 29) and a CDR-H2 having the amino acid sequence "FIRNKANGGTTEYAASVKG" (SEQ ID NO. 28) and a CDR-H3 having the amino acid sequence "DRGLRFYFDY" (SEQ ID NO. 27); and (b) a CDR-H1 having the amino acid sequence "TYAMH" (SEQ ID NO. 31) and a CDR-H2 having the amino acid sequence "LISNDGSNKYYADSVKG" (SEQ ID NO. 30) and a CDR-H3 having the amino acid sequence "DRGLRFYFDY" (SEQ ID NO. 27).

The amino acid sequence "DRGLRFYFDY" (SEQ ID NO. 27) corresponds to Kabat positions 95-102 of the CDR-H3 of murine monoclonal antibody A5B7 (Chester, Int. J. Cancer 57 (1994), 67-72; Harwood, Br J Cancer. 54 (1986), 75-82).

In a preferred embodiment of the pharmaceutical composition of the invention, said variable region of the IgG1 antibody defined herein comprises a CDR-L1 having the amino acid sequence "TLRRGINVGAYSIY" (SEQ ID NO. 34) and/or a CDR-L2 having the amino acid sequence "YKSDSDKQQGS" (SEQ ID NO. 33) and/or a CDR-L3 having the amino acid sequence "MIWHSGASAV" (SEQ ID NO. 32).

Determination of CDRs is known to the person skilled in the art; see e.g. www.bioinf.org.uk/abs/#cdrid. Numbering of amino acid sequences in antibodies can be carried out e.g. according to the Kabat numbering scheme described in the art; see e.g. Kabat, E. A., T. T. Wu, H. M. Perry, K. S. Gottesman, and C. Foeller. 1991. Sequences of Proteins of Immunological Interest, 5th ed. Bethesda, Md.: National Center for Biotechnology Information, National Library of Medicine.

The present invention provides means and methods particularly suited for the treatment of (an) epithelial tumor(s) in patients with high soluble CEA concentrations in their serum/plasma. Such high soluble CEA concentrations are found in the serum/plasma of epithelial tumor patients with progressive tumors, recurrent, metastatic, late stage tumors and for patients with high tumor load/burden. It has been found that IgG1 antibodies specifically binding to human CEA which comprise a variable region as defined above not only bind to CEA-positive target cells, but also to soluble CEA; see Example 5 of the present invention. Surprisingly, although binding to soluble CEA, the IgG1 antibodies of this invention kill CEA-bearing tumor cells, even in the presence of high concentrations of soluble CEA. Put in other words, said IgG1 antibody constructs are not inhibited by soluble CEA in their cytotoxic activity (antibody-dependent cell cytotoxic activity; ADCC) against CEA-positive tumor cells. For instance, Example 5 shows cytotoxic activity against Kato III cells (CEA-positive human gastric carcinoma cell line) of CEA-reactive IgG1 antibody constructs as defined above in the presence of increasing amounts of soluble CEA antigen. Thus, cytotoxicity mediated by the IgG1 antibodies as defined herein is resistant to soluble CEA. The IgG1 antibodies of the present invention as defined herein comprise a variable region with CDR-H regions as set forth above, including the CDR-H3 "DRGLRFYFDY" (SEQ ID NO. 27) amino acid sequence corresponding to Kabat positions 95-102 of murine monoclonal antibody A5B7 (Chester; Harwood; loc. cit.). This monoclonal antibody also binds both to membrane-bound and soluble CEA (own data). It has been found that the amino acid sequence "DRGLRFYFDY" mediates resistance to soluble CEA when used in the variable regions of humanized anti-CEA IgG1 antibodies as defined herein; see Example 5.

In contrast, as shown in Example 2, huIgG1 CEAII-mediated cytotoxic activity is inhibited by increasing amounts of soluble CEA. The variable region of huIgG1 CEAII is derived from mAb T84.66 (Neumaier, Cancer Res. 50 (1990), 2128-2134). Since huIgG1 CEAII has been found to bind to soluble CEA, it was concluded that soluble CEA antigen prevents the antibody from exerting its antibody-mediated cytotoxic activity. In light of the results obtained for T84.66-derived IgG1 constructs, it could not be expected that soluble CEA does not inhibit cytotoxic activity in A5B7-derived antibody constructs. More specifically, resistance to soluble CEA antigen could be found only for IgG1 antibodies, the variable regions of which comprised the amino acid sequence "DRGLRFY-FDY" of the CDR-H3 of murine monoclonal antibody A5B7 (Chester, loc. cit.; Harwood, Br J Cancer. 54 (1986), 75-82).

As set forth above, many therapeutic approaches directed against CEA-bearing epithelial tumors in humans are seriously hampered by the presence of high levels of soluble CEA antigen in the plasma of cancer patients. Soluble CEA antigen—frequently present in high concentrations in the serum of cancer patients with progressive tumors, recurrent cancer, metastasic tumors, high tumor load/burden, or late-stage tumors, blocks the therapeutics directed against CEA-positive tumor cells, thus preventing tumor cell recognition and destruction. Therefore, the actual amount of the therapeutic which reaches the tumor is reduced, resulting in a reduced low or even no anti-tumor activity. This limitation so far restricts e.g. antibody-based approaches to those patients with very low serum levels of soluble CEA antigen unlikely to prevent therapeutic-tumor cell interaction. Current therapeutic approaches with CEA specific Ig molecules do not show anti-tumor activity in patients with high serum levels of soluble CEA.

In the present invention, it has been found that it is possible to generate antibody-therapeutics with specificity for human CEA, wherein the cytotoxic (ADCC) activity directed against tumor cells is resistant to even high concentrations of soluble CEA antigen. This finding is entirely unexpected in view of the fact that the IgG1 antibodies of the invention bind to soluble CEA antigen (see Example 5). Nevertheless, the IgG1 antibodies as defined herein are resistant to the presence of even high levels of soluble CEA in their cytotoxic activity towards tumor cells. Thus, the present invention provides means and methods particularly suited for the treatment of tumor patients with high soluble CEA concentrations in their plasma, as observed e.g. during tumor progression, for recurrent cancer, for metastasis, for patients with high tumor load/burden, or late-stage tumors.

In light of this finding, the IgG1 antibodies in the pharmaceutical compositions of the invention in the following are referred to as being resistant to soluble CEA antigen. The term "resistance to soluble CEA antigen", "resistant to soluble CEA" (or related terms) as used herein refers to the fact that the cytotoxicity against CEA-positive tumor cells mediated by said IgG1 antibodies is not affected by increasing concentrations of soluble CEA. In particular, the cytotoxic activity is not inhibited by even high concentrations of soluble CEA. As set forth above, CEA levels in the blood of healthy individuals is less than 2 ng/ml. High soluble CEA concentrations in the serum/plasma of tumor patients are characteristic for progressive, recurrent, metastatic, or late stage tumors and for patients with high tumor load. Thus, the present invention provides means and methods particularly suited for the treatment of epithelial tumor patients with such high soluble CEA concentrations in their plasma. The term "high soluble CEA concentrations" as used herein denotes a soluble serum/plasma-CEA concentration higher than 10, 20, 50, 70, 80, 90 or 100 ng/ml. The serum/plasma CEA concentration may, inter alia, be determined by ELISA techniques. Preferably, said soluble serum/plasma-CEA concentration is higher than 100 ng/ml, as for example determined by ELISA. The CEA serum concentration can be determined e.g. by CEA ELISA assays (see e.g. IBL CEA EIA, IBL Hamburg, Germany).

In accordance with this invention, the term "pharmaceutical composition" relates to a composition for administration to a human patient. Preferably, the pharmaceutical composition comprises suitable formulations of carriers, stabilizers and/or excipients. In a preferred embodiment, the pharmaceutical composition comprises a composition for parenteral, transdermal, intraluminal, intraarterial, intrathecal and/or intranasal administration or by direct injection into tissue. It is in particular envisaged that said composition is administered to a patient via infusion or injection. Administration of the suitable compositions may be effected by different ways, e.g., by intravenous, intraperitoneal, subcutaneous, intramuscular, topical or intradermal administration. The composition of the present invention may further comprise a pharmaceutically acceptable carrier. Examples of suitable pharmaceutical carriers are well known in the art and include phosphate buffered saline solutions, water, various types of wetting agents, sterile solutions, liposomes, etc. Compositions comprising such carriers can be formulated by well known conventional methods. These compositions can be administered to the subject at a suitable dose which can be determined e.g. by dose escalating studies by administration of increasing doses of the IgG1 antibodies exhibiting resistance to soluble serum CEA antigen described herein. As set forth above, the IgG1 antibodies described herein with resistance to soluble serum CEA antigen can be advantageously used in the treatment of cancer patients with high CEA serum concentrations, such as progressive tumors, recurrent cancer, metastatic tumors, high tumor load/burden, or late stage tumors. These compositions can also be administered in combination with other proteinaceous and non-proteinaceous drugs, e.g. in the form of a co-therapy. These drugs may be administered simultaneously with the composition comprising the IgG1 antibodies as defined herein or separately before or after administration of said IgG1 antibodies in timely defined intervals and doses. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Preparations for parenteral administration include sterile aqueous or non-aqueous solutions, and suspensions. Examples of non-aqueous solvents are propylene glycol, polyethylene glycol, vegetable oils, and injectable organic esters such as ethyl oleate. Aqueous carriers include water, aqueous solutions, or suspensions, including saline and buffered media. Parenteral vehicles include sodium chloride solution, Ringer's dextrose, dextrose and sodium chloride, or lactated Ringer's. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the composition of the present invention might comprise proteinaceous carriers, like, e.g., serum albumin or immunoglobulin, preferably of human origin. It is envisaged that the co-therapy comprise, in addition to the IgG1 antibodies as defined herein, further biologically active agents, depending on the intended use of the composition. Such agents might be drugs acting on the gastro-intestinal system, drugs acting as antineoplastic agents, chemotherapeutics, cytostatica, drugs preventing hyperurikemia, drugs inhibiting immunoreactions (e.g. corticosteroids), drugs modulating the inflammatory response, drugs acting on the circulatory system and/or agents such as cytokines known in the art.

Preferably, the IgG1 antibody as defined herein is formulated in a buffer, a stabilizer and a surfactant. The buffer may be a phosphate, citrate, succinate or acetate buffer. The stabilizer may be (an) amino acid(s) and/or a sugar. The surfactants may be detergents, PEGs, or the like. More preferably, the IgG1 antibody as defined herein is formulated in citrate, lysine, trehalose and Tween 80. As a diluent for the pharmaceutical composition of the invention, isotonic saline and Tween 80 is preferred.

As used herein, an "antibody" denotes immunoglobulin molecules, i.e., molecules that contain an antigen binding site that immunospecifically binds an antigen, preferably human CEA. All antibodies are constructed in the same way. They form paired heavy and light polypeptide chains, and the generic term immunoglobulin is used for all such proteins. Within this general category, however, five different classes of immunoglobulins—IgM, IgD, IgG, IgA, and IgE—can be distinguished by their C regions. IgG antibodies are large molecules, having a molecular weight of approximately 150 kDa, composed of two different kinds of polypeptide chain. One, of approximately 50 kDa, is termed the heavy or H chain, and the other, of 25 kDa, is termed the light or L chain. Each IgG molecule consists of two heavy chains and two light chains. The two heavy chains are linked to each other by disulfide bonds and each heavy chain is linked to a light chain by a disulfide bond. In any given immunoglobulin molecule, the two heavy chains and the two light chains are identical, giving an antibody molecule two identical antigen-binding sites, and thus the ability to bind simultaneously to two identical structures. Two types of light chain, termed lambda and kappa, are found in antibodies. A given immunoglobulin either has lambda chains or kappa chains, never one of each. No functional difference has been found between antibodies having lambda or kappa light chains, and either type of light chain may be found in antibodies of any of the five major classes. The ratio of the two types of light chain varies from species to species. In mice, the average kappa to lambda ratio is 20:1, whereas in humans it is 2:1 and in cattle it is 1:20. The reason for this variation is unknown. By contrast, the class, and thus the effector function of an antibody, is defined by the structure of its heavy chain. There are five main heavy-chain classes or isotypes, some of which have several subtypes, and these determine the functional activity of an antibody molecule. The five major classes of immunoglobulin are immunoglobulin M (IgM), immunoglobulin D (IgD), immunoglobulin G (IgG), immunoglobulin A (IgA), and immunoglobulin E (IgE). Their heavy chains are denoted by the corresponding lower-case Greek letter (mu, delta, gamma, alpha, and epsilon, respectively). IgG is by far the most abundant immunoglobulin and has several subclasses (IgG1, 2, 3, and 4 in humans). Their distinctive functional properties are conferred by the carboxy-terminal part of the heavy chain, where it is not associated with the light chain. The general structural features of all the isotypes are similar. The structure of an IgG antibody, the most abundant isotype in plasma, as a typical antibody molecule is exemplified in FIG. 1.

Preferably, the antibodies as defined herein are IgG antibodies. As is well known in the art, an IgG comprises not only the variable antibody regions responsible for the highly discriminative antigen recognition and binding, but also the constant regions of the heavy and light antibody polypeptide chains normally present in endogenously produced antibodies and, in some cases, even decoration at one or more sites with carbohydrates. Such glycosylation is generally a hallmark of the IgG format, and portions of these constant regions make up the so called Fc region of a full antibody which is known to elicit various effector functions in vivo, such as e.g. antibody-dependent cellular cytotoxicity (ADCC). In addition, the Fc region mediates binding of the IgG to an Fc receptor, hence prolonging half life in vivo as well as facilitating homing of the IgG to locations with increased Fc receptor presence. Advantageously, the IgG antibody is an IgG1 antibody specifically binding to the human CEA antigen, formats which are preferred since their mechanism of action in vivo is particularly well understood and characterized. This is especially the case for IgG1 antibodies.

The IgG1 antibodies referred to herein comprise the variable region(s) as defined above in combination with the entirety or a portion of the hinge region, CH1, CH2, and CH3 domains and CL domains; see e.g. FIG. 1. Generally, in a variable region, a VH domain is paired with a VL domain to provide an antibody antigen binding site. Preferably, the VH domain comprising (i) a CDR-H1 having the amino acid sequence "SYWMH" (SEQ ID NO. 29) and a CDR-H2 having the amino acid sequence "FIRNKANGGTTEYAASVKG" (SEQ ID NO. 28) and a CDR-H3 having the amino acid sequence "DRGLRFYFDY" (SEQ ID NO. 27) corresponding to Kabat positions 95-102 of the CDR-H3 of murine monoclonal antibody A5B7 or (ii) a CDR-H1 having the amino acid sequence "TYAMH" (SEQ ID NO. 31) and a CDR-H2 having the amino acid sequence "LISNDGSNKYYADSVKG" (SEQ ID NO. 30) and a CDR-H3 having the amino acid sequence "DRGLRFYFDY" (SEQ ID NO. 27) corresponding to Kabat positions 95-102 of the CDR-H3 of murine monoclonal antibody A5B7 is paired with the VL domain comprising a CDR-L1 having the amino acid sequence "TLRRGINVGAYSIY" (SEQ ID NO. 34) and a CDR-L2 having the amino acid sequence "YKSDSDKQQGS" (SEQ ID NO. 33) and a CDR-L3 having the amino acid sequence "MIWHSGASAV" (SEQ ID NO. 32), so that an antibody antigen binding site is formed comprising one of the mentioned VH domains and the said VL domain. The anti-CEA IgG1 antibodies defined herein may be rodent antibodies (i.e. from mice or rats). Preferably, said IgG1 antibodies are humanized antibodies as set forth in more detail below.

According to the present invention, the term "binding domain" or "variable region" used in the context with Ig-derived antigen-interaction comprises fragments and derivatives of polypeptides which at least comprise one CDR derived from an antibody, antibody fragment or derivative thereof. It is envisaged by the invention, that the binding domain specifically binding to human CEA of the IgG1 antibody defined herein comprises at least one CDR, preferably a CDR-H3, more preferably the CDR-H3 of murine monoclonal antibody A5B7 with the amino acid sequence "DRGLRFYFDY" (SEQ ID NO. 27) corresponding to Kabat positions 95-102 of the CDR-H3 of A5B7. As shown in the following Examples, the cytotoxic activity against tumor cells of the IgG1 antibodies defined herein comprising said mAb A5B7-derived CDR-H3 "DRGLRFYFDY" (SEQ ID NO. 27) amino acid sequence is resistant to soluble CEA antigen, thereby allowing the treatment of tumor patients with high serum CEA concentrations in their plasma.

As used herein, "human" refers to the species *Homo sapiens*. A "human" molecule, e.g. human CEA, is therefore the variant of that molecule as it is naturally expressed in *Homo sapiens*.

The term "epithelial tumor" as used herein denotes a tumor of epithelial origin which is CEA positive (Cancer Medicine; 6th ed.; Kufe, Donald W.; Pollock, Raphael E.; Weichselbaum, Ralph R.; Bast, Robert C., Jr.; Gansler, Ted S.; Holland, James F.; Frei III, Emil, editors. Hamilton (Canada): BC Decker Inc. 2003; www.dkfz.de; www.krebsinformationsdienst.de/Krebsarten/index.html). The epithelial tumor to be treated may be a gastrointestinal adenocarcinoma, a breast adenocarcinoma or a lung adenocarcinoma. Said gastrointestinal adenocarcinoma is preferably a colorectal, pancreatic, an esophageal or a gastric adenocarcinoma. As set forth herein, the pharmaceutical composition of the invention is particularly advantageous for the treatment of patients with progressive tumors, metastasis, recurrent cancer, late stage epithelial tumors, high epithelial tumor load/tumor burden, or tumor patients with a CEA serum concentration higher than 100 ng/ml (as determined e.g. by ELISA), characterized by high levels of soluble CEA antigen in the serum/plasma of the tumor patients. It is also within the scope of the invention that said pharmaceutical composition be administered after surgical removal of the primary tumor. For example, disseminated residual tumor cells derived from a CEA producing epithelial tumor also shed CEA into their microenvironments, in the surrounding of which the level of soluble CEA is high. Accordingly, resistance to soluble CEA of cytotoxic activity of IgG1 antibodies as defined herein is advantageous also for the treatment of minimal residual disease. Thus, it is envisaged that the IgG 1 antibodies as defined herein may be administered in a period in which serum CEA levels decrease (due to the removal of the CEA source, i.e. the primary tumor) in order to kill remaining tumor cells. Or the IgG1 antibodies as defined herein may be useful after the removal of the primary tumor, in the case that serum CEA levels increase due to the formation of secondary tumors or metastasis. The CEA serum concentration can be determined e.g. by CEA ELISA assays (see e.g. IBL CEA EIA, IBL Hamburg, Germany). As set forth above, in many antibody-based therapeutic approaches, said serum CEA inhibits binding of the antibody to membrane-bound CEA on the tumor cells and blocks the activity of antibody, thereby worsening the success of the anti-tumor therapy.

As used herein, the term "specifically binds" or related expressions such as "specifically binding" or "specific reactivity with/to" etc. refer to the ability of the binding domains of the IgG1 antibody as defined herein to discriminate between a first and/or second molecule to such an extent that, from a pool of a plurality of different molecules as potential binding partners, only said respective first and/or second molecule is/are bound, or is/are significantly bound. Such binding measurements can be routinely performed e.g. on a Biacore™ apparatus, by ELISA, FACS analysis or the like. More specifically, the binding domain of the IgG1 antibody as defined herein binds to a epithelial tumor antigen, i.e. human CEA (carcinoembryonic antigen, carcinoembryonic antigen related cell adhesion molecule 5; CEACAM5; CD66e), as set forth below. The term "specifically binding" means in accordance with this invention that the IgG1 antibody molecule is capable of specifically interacting with and/or binding to at least two, three, four, five, six, seven, eight or even more amino acids of human CEA as defined herein. Said term relates to the specificity of the antibody molecule, i.e. to its ability to discriminate between the specific regions of the human CEA antigen as defined herein. The specific interaction of the antigen-interaction-site with its specific antigen may result in an initiation of a signal, e.g. due to the induction of a change of the conformation of the antigen, an oligomerization of the antigen, etc. Further, said binding may be exemplified by the specificity of a "key-lock-principle". Thus, specific motifs in the amino acid sequence of the antigen-interaction-site and the antigen bind to each other as a result of their primary, secondary or tertiary structure as well as the result of secondary modifications of said structure. The specific interaction of the antigen-interaction-site with its specific antigen may result as well in a binding of said site to the antigen.

The "specific binding" of an antibody is characterized primarily by two parameters: a qualitative parameter (the binding epitope, or where the antibody binds) and a quantitative parameter (the binding affinity, or how strongly it binds where it does). Which epitope is bound by an antibody can advantageously be determined by e.g. known FACS methodology, peptide-spot epitope mapping, mass spectroscopy or peptide ELISA. The strength of antibody binding to a particular epitope may be advantageously be determined by e.g. known Biacore™ and/or ELISA methodologies. A combination of such techniques allows the calculation of a signal:noise ratio as a representative measure of binding specificity. In such a signal:noise ratio, the signal represents the strength of antibody binding to the epitope of interest, whereas the noise represents the strength of antibody binding to other, nonrelated epitopes differing from the epitope of interest. Preferably, a signal:noise ratio for an epitope of interest which is about 50-fold higher than for other epitopes different from the epitope of interest may be taken as an indication that the antibody evaluated binds the epitope of interest in a specific manner, i.e. is a "specific binder"

The term "specific binding" or "specific interaction" as used in accordance with the present invention means that the IgG1 antibody construct does not or essentially does not cross-react with polypeptides of similar structures. Cross-reactivity of a panel of antibody constructs under investigation may be tested, for example, by assessing binding of said panel of antibody constructs under conventional conditions (see, e.g., Harlow and Lane, Antibodies: A Laboratory Manual, Cold Spring Harbor Laboratory Press, 1988 and Using Antibodies: A Laboratory Manual, Cold Spring Harbor Laboratory Press, 1999) to the polypeptide of interest as well as to a number of more or less (structurally and/or functionally) closely related polypeptides. For example, it is within the scope of the invention that the binding domain of the IgG1 antibody defined herein binds to human CEA (carcinoembryonic antigen; CEACAM5; CEA; CD66e), i.e. both to soluble CEA and to membrane-bound CEA, whereas IgG1 antibodies binding to other CEA family members, such as biliary glycoprotein (CEACAM1; BGP1; TM-CEA; CD66a), are excluded from said scope.

Examples for the specific interaction of an antigen-interaction-site with a specific antigen comprise the specificity of a ligand for its receptor. Said definition particularly comprises the interaction of ligands which induce a signal upon binding to its specific receptor. Examples for corresponding ligands comprise cytokines which interact/bind with/to its specific cytokine-receptors. Also particularly comprised by said definition is the binding of an antigen-interaction-site to antigens like antigens of the selectin family, integrins and of the family of growth factors like EGF. Another example for said interaction, which is also particularly comprised by said definition, is the interaction of an antigenic determinant (epitope) with the antigenic binding site of an antibody.

The term "binding to/interacting with" may also relate to a conformational epitope, a structural epitope or a discontinuous epitope consisting of two regions of the human target molecule, i.e. human CEA, or parts thereof. In context of this invention, a conformational epitope is defined by two or more discrete amino acid sequences separated in the primary sequence which come together on the surface of the molecule when the polypeptide folds to the native protein (Sela, (1969) Science 166, 1365 and Laver, (1990) Cell 61, 553-6).

The term "discontinuous epitope" means in context of the invention non-linear epitopes that are assembled from residues from distant portions of the polypeptide chain. These residues come together on the surface of the molecule when the polypeptide chain folds into a three-dimensional structure to constitute a conformational/structural epitope.

"CEA" denotes the carcinoembryonic antigen (carcinoembryonic antigen-related cell adhesion molecule 5; CEACAM5; CEA; CD66e), an antigen expressed in a large number of tumors of epithelial origin (Hammarstrom, Sem. Cancer Biol. 9 (1999), 67-81; Shively and Beatty CRC Crit. Rev. Oncol. Hematol. 2 (1985), 355-399). The amino acid sequence of human CEA is depicted in GenBank accession number NM_004363 and comprises SEQ ID NO. 37.

In the present invention, it has been surprisingly found that it is possible to generate antibody-based therapeutics with specificity for human CEA, wherein the cytotoxic activity (ADCC) directed against tumor cells is resistant to even high concentrations of soluble CEA antigen. This finding is entirely unexpected in view of the fact that the IgG1 antibodies defined herein bind to soluble CEA antigen. For example, when IgG1 antibody constructs derived from monoclonal antibody T84.66 have been generated, these antibodies were highly sensitive to soluble CEA antigen, ie. their cytotoxic activity (ADCC) has been blocked in the presence of soluble CEA antigen. These constructs have also been found to be capable of binding to soluble CEA. In view of this, it was concluded that soluble CEA antigen prevents the antibodies from exerting their cytotoxic activity. In contrast, the IgG1 antibodies as defined herein are resistant to the presence of even high levels of soluble CEA in their cytotoxic activity towards tumor cells. Even more surprising, it has been found that the amino acid sequence "DRGLRFYFDY" (SEQ ID NO. 27) corresponding to Kabat positions 95-102 of the CDR-H3 of murine monoclonal antibody A5B7 is sufficient to mediate resistance to soluble CEA antigen when used in a human CEA-binding domain (i.e. human binding domains specifically binding to human CEA) of human IgG1 antibodies. Due to their human origin (with exception of the "DRGLRFYFDY" amino acid sequence), said constructs are low or non-immunogenic when being administered to human tumor patients. In summary, the pharmaceutical compositions comprising the IgG1 antibodies as defined herein are particularly useful for the treatment of epithelial tumor patients with high soluble CEA concentrations in their plasma, as observed e.g. during tumor progression, for recurrent cancer, for metastasis, for patients with high tumor load/burden, or late-stage tumors. Such IgG1 antibodies as defined herein can be generated by methods described in the art, e.g. by phage-display based techniques; see also the following Examples.

It is preferred that the binding domain specifically binding to human CEA of the IgG1 antibody defined herein comprises at least one CDR, preferably a CDR-H3, more preferably a part of or the complete CDR-H3 of murine monoclonal antibody A5B7 with the amino acid sequence "DRGLRFYFDY" (SEQ ID NO. 27) corresponding to Kabat positions 95 ("D"; Aspartic acid), 96 ("R"; Arginine), 97 ("G"; Glycine), 98 ("L"; Leucine), 99 ("R"; Arginine), 100 ("F"; Phenylalanine), 100a ("Y"; Tyrosine), 100b ("F"; Phenylalanine), 101 ("D"; Aspartic acid), and 102 ("Y"; Tyrosine), respectively. Numbering according to the Kabat system is set forth e.g. in Kabat, E. A., T. T. Wu, H. M. Perry, K. S. Gottesman, and C. Foeller. 1991. Sequences of Proteins of Immunological Interest, 5th ed. Bethesda, Md.: National Center for Biotechnology Information, National Library of Medicine.

As shown in the following Examples, the cytotoxic activity (ADCC) against tumor cells of the IgG1 antibodies defined herein comprising said mAb A5B7-derived CDR-H3 "DRGLRFYFDY" (SEQ ID NO. 27) amino acid sequence in the binding domain interacting with CEA are resistant to soluble CEA antigen, thereby allowing the treatment of tumor patients with high serum CEA concentrations in their plasma.

It may be desirable to further modify this A5B7-derived "DRGLRFYFDY" CDR-H3 amino acid sequence e.g. in order to improve affinity for the CEA target antigen (on the epithelial tumor cells) and/or to optimize the "fine specificity" of the IgG1 antibodies as defined herein. To this end, for example, in the amino acid sequence "$DX_1X_2X_3X_4FYFDY$", various amino acid residues may be tested at positions "$X_1$", "$X_2$", "$X_3$" and/or "$X_4$" (corresponding to Kabat positions 96 ("$X_1$"), 97 ("$X_2$"), 98 ("$X_3$") and 99 ("$X_4$"), respectively, of CDR-H3 of murine monoclonal antibody A5B7) in order to identify a modified CDR-H3 with improved affinity and/or fine specificity. For instance, "$X_1$", "$X_2$", "$X_3$" or "$X_4$" may represent amino acid residue "R" (Arginine), "G" (Glycine), "L" (Leucine), "Y" (Tyrosine), "A" (Alanine), "D" (Aspartic acid), "S" (Serine), "W" (Tryptophan), "F" (Phenylalanine) or "T" (Threonine). Herein, one, two, three or all four of the indicated "X" positions may be exchanged in comparison to the original "RGLR" amino acid sequence at Kabat positions 96 to 99 in the CDR-H3 "DRGLRFYFDY" (SEQ ID NO. 27) amino acid sequence. However, it is excluded from the scope of the claims of the invention that "$X_1$", "$X_2$", "$X_3$" and "$X_4$" represent the same amino acid, e.g. that "$X_1$", "$X_2$", "$X_3$" and "$X_4$" are all "F" (Phenylalanine). The above-mentioned modification of the A5B7-derived "DRGLRFYFDY" CDR-H3 amino acid sequence can be achieved by methods known in the art, such as PCR using randomized primers, which allows the generation of IgG 1 antibodies with such modified CDR-H3 regions in the CEA-binding domain. Affinity or fine specificity of these modified IgG1 antibodies can be tested by methods described in the art, e.g. by ELISA, Biacore™ or FACS analysis. The resistance to soluble CEA antigen of an IgG1 antibody with such a modified CDR-H3 can be tested in cytotoxicity (antibody dependent cell-mediated cytotoxicity, ADCC) assays in the presence of increasing amounts of soluble CEA, as described in the following Examples.

Preferably, the variable region of the IgG1 antibodies defined herein comprises at least the amino acid sequences selected from the group consisting of:

(a) a CDR-H1 having the amino acid sequence "SYWMH" (SEQ ID NO. 29) and a CDR-H2 having the amino acid sequence "FIRNKANGGTTEYAASVKG" (SEQ ID NO. 28) and a CDR-H3 having the amino acid sequence "DRGLRFYFDY" (SEQ ID NO. 27) corresponding to Kabat positions 95-102 of the CDR-H3 of murine monoclonal antibody A5B7; and (b) a CDR-H1 having the amino acid sequence "TYAMH" (SEQ ID NO. 31) and a CDR-H2 having the amino acid sequence "LISNDGSNKYYADSVKG" (SEQ ID NO. 30) and a CDR-H3 having the amino acid sequence "DRGLRFYFDY" (SEQ ID NO. 27) corresponding to Kabat positions 95-102 of the CDR-H3 of murine monoclonal antibody A5B7.

More preferably, said variable region comprises a CDR-L1 having the amino acid sequence "TLRRGINVGAYSIY" (SEQ ID NO. 34) and/or a CDR-L2 having the amino acid sequence "YKSDSDKQQGS" (SEQ ID NO. 33) and/or a CDR-L3 having the amino acid sequence "MIWHSGASAV" (SEQ ID NO. 32).

The amino acid sequence of the VH region of the binding domain specific for human CEA of the IgG1 antibodies defined herein is preferably SEQ ID NO. 20, 22 or 24.

The amino acid sequence of the VL region of the binding domain specific for human CEA of the IgG1 antibodies defined herein is preferably SEQ ID NO. 26.

Even more preferred, the variable (V) regions of the binding domain specific for CEA of the IgG1 antibodies defined herein are selected from the group consisting of:

(a) the VH region consists of the amino acid sequence shown in SEQ ID NO. 22 and the VL region consists of the amino acid sequence shown in SEQ ID NO. 26;

(b) the VH region consists of the amino acid sequence shown in SEQ ID NO. 20 and the VL region consists of the amino acid sequence shown in SEQ ID NO. 26; and (c) the VH region consists of the amino acid sequence shown in SEQ ID NO. 24 and the VL region consists of the amino acid sequence shown in SEQ ID NO. 26.

Most preferred, said IgG1 antibody as defined herein comprises an amino acid sequence selected from the group consisting of:

(a) an amino acid sequence of the heavy chain shown in SEQ ID NO. 77 and an amino acid sequence of the light chain shown in SEQ ID NO. 80;

(b) an amino acid sequence of the heavy chain shown in SEQ ID NO. 78 and an amino acid sequence of the light chain shown in SEQ ID NO. 80;

(c) an amino acid sequence of the heavy chain shown in SEQ ID NO. 79 and an amino acid sequence of the light chain shown in SEQ ID NO. 80; and (d) an amino acid sequence at least 85% identical, more preferred at least 90% identical, most preferred at least 95% identical to the amino acid sequence of (a), (b) or (c).

Most preferably and as documented in the appended examples, the "IgG1 antibody" to be employed in the pharmaceutical composition of the invention is a humanized IgG1 antibody with human constant regions and a humanized variable region comprising the amino acid sequence "DRGLR-FYFDY" corresponding to Kabat positions 95-102 (SEQ ID NO. 27) of the CDR-H3 of murine monoclonal antibody A5B7.

Preferably, the light chain constant region of said IgG1 antibody is a lambda light chain constant region, preferably a human lambda light chain constant region.

The IgG1 antibody as defined herein may be derivatized, for example with an organic polymer, e.g. with one or more molecules of polyethylene glycol ("PEG") and/or polyvinyl pyrrolidone ("PVP"). As is known in the art, such derivatization can be advantageous in modulating the pharmacodynamic properties of antibodies or fragments thereof. Especially preferred are PEG molecules derivatized as PEG-maleimide, enabling conjugation with the antibody or fragment thereof in a site-specific manner via the sulfhydryl group of a cysteine amino acid. Of these, especially preferred are 20 kD and/or 40 kD PEG-maleimide, in either branched or straight-chain form.

Moreover, the IgG1 antibody as defined herein may be fused to radionuclides (e.g. $^{131}$I) cell toxins (e.g. Pseudomonas toxin A) or cytokines, such as IL-2. The resulting fusion proteins are preferably used for therapeutic purposes in the treatment of epithelial tumors. Antibodies of the invention fused to radionuclides may also be useful e.g. for diagnostic purposes.

In another preferred embodiment of the pharmaceutical composition of the invention, said epithelial tumor to be treated is a gastrointestinal adenocarcinoma, a breast adenocarcinoma or a lung adenocarcinoma. Said gastrointestinal adenocarcinoma is preferably a colorectal, pancreatic, an oesophageal or a gastric adenocarcinoma.

More preferably, said pharmaceutical composition of the invention is for the treatment of progressive tumors, late stage tumors, tumor patients with high tumor load/burden, metastatic tumors, or tumor patients with a CEA serum concentration higher than 100 ng/ml. Said CEA serum concentration may be determined e.g. by ELISA.

In a further preferred embodiment of the pharmaceutical composition of the invention, the IgG1 antibodies defined herein are humanized and/or deimmunized.

As used herein, the term "CDR-grafted", "humanized" or "humanization" are used interchangeably to refer to a human IgG1 antibody comprising in its binding domains at least one complementarity determining region ("CDR") from a non-human antibody or fragment thereof. Humanization approaches are described for example in WO 91/09968 and U.S. Pat. No. 6,407,213. As non-limiting examples, the term encompasses the case in which a variable region of the binding domain comprises a single CDR region, for example the third CDR region (CDR-H3) of the VH, from another non-human animal, for example a rodent, as well as the case in which a or both variable region/s comprise at each of their respective first, second and third CDRs the CDRs from said non-human animal. In the event that all CDRs of a binding domain of the antibody have been replaced by their corresponding equivalents from, for example, a rodent, one typically speaks of "CDR-grafting", and this term is to be understood as being encompassed by the term "humanized" as used herein. The term "humanized" also encompasses cases in which, in addition to replacement of one or more CDR regions within a VH and/or VL of the binding domain further mutation/s (e.g. substitutions) of at least one single amino acid residue/s within the framework ("FR") regions between the CDRs has/have been effected such that the amino acids at that/those positions correspond/s to the amino acid/s at that/those position/s in the animal from which the CDR regions used for replacement is/are derived. As is known in the art, such individual mutations are often made in the framework regions following CDR-grafting in order to restore the original binding affinity of the non-human antibody used as a CDR-donor for its target molecule. The term "humanized" may further encompass (an) amino acid substitution(s) in the CDR regions from a non-human animal to the amino acid(s) of a corresponding CDR region from a human antibody, in addition to the amino acid substitutions in the framework regions as described above.

More specifically, as used herein, "humanized antibodies" or related terms encompass IgG1 antibodies having the amino acid sequence of a human immunoglobulin with a variable region comprising human CDR- and framework region-sequences, with exception of a CDR-H3 having the amino acid sequence "DRGLRFYFDY" (SEQ ID NO. 27) corresponding to Kabat positions 95-102 of the CDR-H3 of murine monoclonal antibody A5B7. Such antibodies can be generated as set forth in the following Examples. It is especially advantageous that the IgG1 antibody as described herein be a humanized antibody. In contemplating an antibody agent intended for therapeutic administration to humans, it is highly advantageous that the major part of this antibody is of human origin. Following administration to a human patient, a humanized antibody (or fragment) thereof will most probably not elicit a strong immunogenic response by the patient's immune system, i.e. will not be recognized as being a "foreign", that is non-human protein. This means that no host, i.e. patient antibodies will be generated against the therapeutic antibody which would otherwise block the therapeutic antibody's activity and/or accelerate the therapeutic antibody's elimination from the body of the patient, thus preventing it from exerting its desired therapeutic effect. The term "humanized" antibody as used herein is to be understood as meaning that the IgG1 antibody as defined herein comprises (an) amino acid sequence(s) contained in the human antibody repertoire, and a CDR-H3 having the amino acid sequence "DRGLRFYFDY" (SEQ ID NO. 27) corresponding to Kabat positions 95-102 of the CDR-H3 of murine monoclonal antibody A5B7. For the purposes of definition herein, an antibody, or its fragment, may therefore be considered humanized if it consists of such (a) human amino acid sequence(s), i.e. if the amino acid sequence(s) of the antibody in question or fragment thereof is (are) identical to (an) expressed human germline amino acid sequence(s), with exception of the murine CDR-H3 indicated above. An IgG1 antibody as defined herein may also be regarded as humanized if it consists of (a) sequence(s) that deviate(s) from its (their) closest human germline sequence(s) by no more than would be expected due to the imprint of somatic hypermutation. Preferably, the (humanized) IgG1 antibodies as defined herein have a human constant region and a human variable region comprising a CDR-H3 having the amino acid sequence "DRGLRFYFDY" (SEQ ID NO. 27) corresponding to Kabat positions 95-102 of the CDR-H3 of murine monoclonal antibody A5B7. As set forth above, said CDR-H3 mediates resistance to soluble CEA.

As used herein, the term "deimmunized" or "deimmunization" denotes modification of the binding domain vis-à-vis an original wild type construct by rendering said wild type construct non-immunogenic or less immunogenic in humans. Deimmunization approaches are shown e.g. in WO 00/34317, WO 98/52976, WO 02/079415 or WO 92/10755. The term "deimmunized" also relates to constructs, which show reduced propensity to generate T cell epitopes. In accordance with this invention, the term "reduced propensity to generate T cell epitopes" relates to the removal of T-cell epitopes leading to specific T-cell activation. Furthermore, "reduced propensity to generate T cell epitopes" means substitution of amino acids contributing to the formation of T cell epitopes, i.e. substitution of amino acids, which are essential for formation of a T cell epitope. In other words, "reduced propensity to generate T cell epitopes" relates to reduced immunogenicity or reduced capacity to induce antigen independent T cell proliferation. The term "T cell epitope" relates to short peptide sequences which can be released during the degradation of peptides, polypeptides or proteins within cells and subsequently be presented by molecules of the major histocompatibility complex (MHC) in order to trigger the activation of T cells; see inter alia WO 02/066514. For peptides presented by MHC class II such activation of T cells can then give rise to an antibody response by direct stimulation of T cells to produce said antibodies. "Reduced propensity to generate T-cell epitopes" and/or "deimmunization" may be measured by techniques known in the art. Preferably, de-immunization of proteins may be tested in vitro by T cell proliferation assay. In this assay PBMCs from donors representing >80% of HLA-DR alleles in the world are screened for proliferation in response to either wild type or de-immunized peptides. Ideally cell proliferation is only detected upon loading of the antigen-presenting cells with wild type peptides. Alternatively, one may test deimmunization by expressing HLA-DR tetramers representing all haplotypes. These tetramers may be tested for peptide binding or loaded with peptides substitute for antigen-presenting cells in proliferation assays. In order to test whether deimmunized peptides are presented on HLA-DR haplotypes, binding of e.g. fluorescence-labeled peptides on PBMCs can be measured. Furthermore, deimmunization can be proven by determining whether antibodies against the deimmunized molecules have been formed after administration in patients. Preferably, antibody derived molecules are deimmunized in the framework regions and most of the CDR regions are not modified in order to generate reduced propensity to induce T cell epitope so that the binding affinity of the CDR regions is not affected. Even elimination of one T cell epitope results in reduced immunogenicity. In summary, the above approaches help to reduce the immunogenicity of the therapeutic IgG1 antibodies as defined herein when being administered to epithelial tumor patients.

In another aspect, the invention relates to an IgG1 antibody comprising an amino acid sequence selected from the group consisting of:
 (a) an amino acid sequence of the heavy chain shown in SEQ ID NO. 77 and an amino acid sequence of the light chain shown in SEQ ID NO. 80;
 (b) an amino acid sequence of the heavy chain shown in SEQ ID NO. 78 and an amino acid sequence of the light chain shown in SEQ ID NO. 80;
 (c) an amino acid sequence of the heavy chain shown in SEQ ID NO. 79 and an amino acid sequence of the light chain shown in SEQ ID NO. 80; and
 (d) an amino acid sequence at least 85% identical, more preferred at least 90% identical, most preferred at least 95% identical to the amino acid sequence of (a), (b) or (c).

The invention also relates to nucleic acids encoding the IgG1 antibodies as defined above. Advantageously, said IgG1 antibodies as defined herein or nucleic acids encoding the same are used as pharmaceutical compositions for the treatment of (an) epithelial tumor(s) in human. Said epithelial tumor(s) is (are) CEA-positive. The cytotoxic activity against CEA-positive epithelial tumor cells of the IgG1 antibodies in these pharmaceutical compositions of the invention is resistant to even high concentrations of soluble CEA antigen in the plasma of tumor patients.

Whether any particular polypeptide is at least 80%, 85%, 90%, 95%, 96%, 97%, 98% or 99% identical to a nucleotide or amino acid sequence defined herein can be determined conventionally using known computer programs. A preferred method for determining the best overall match between a query sequence (a sequence defined herein) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are both DNA sequences. An RNA sequence can be compared by converting U's to T's.

The invention also provides for a pharmaceutical composition comprising a nucleic acid sequence encoding an IgG1 antibody as defined herein. Said nucleic acid can be utilized e.g. for gene therapy approaches in order to treat an epithelial tumor in a human, as set forth in more detail below.

The invention further relates to a pharmaceutical composition comprising a vector which comprises a nucleic acid sequence as defined above. Preferably, said vector further comprises a regulatory sequence which is operably linked to said nucleic acid sequence defined above. More preferably, said vector is an expression vector. It is also envisaged that e.g. one expression vector encodes the heavy chains of said antibody, whereas another expression vector codes for the light chains.

Furthermore, the vector of the present invention may also be a gene transfer or gene targeting vector. Gene therapy, which is based on introducing therapeutic genes or nucleic acids into cells by ex-vivo or in-vivo techniques is one of the most important applications of gene transfer. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94/29469; WO 97/00957; U.S. Pat. No. 5,580,859; U.S. Pat. No. 5,589,466; U.S. Pat. No. 4,394,448 or Schaper, Current Opinion in Biotechnology 7 (1996), 635-640, and references cited therein. The nucleic acid molecules and vectors as defined herein may be designed for direct introduction or for introduction via liposomes, viral vectors (e.g. adenoviral, retroviral), electroporation, or other delivery systems into the cell. Additionally, a baculoviral system can be used as eukaryotic expression system for the nucleic acid molecules as defined herein. The introduction and gene therapeutic approach should, preferably, lead to the expression of a functional IgG1 antibody construct as defined herein, whereby said IgG1 antibody construct is particularly useful in the treatment, amelioration and/or prevention of an epithelial tumor in a human.

In a further aspect, the invention relates to a pharmaceutical composition comprising a host transformed or transfected with a vector or a nucleic acid as defined above.

Preferably, the pharmaceutical composition further comprises suitable formulations of carriers, stabilizers and/or excipients.

In another aspect, the invention relates to a process for the production of a pharmaceutical composition as defined above, said process comprising culturing a host as defined above under conditions allowing the expression of the IgG1 antibody as defined hereinabove and recovering the produced IgG1 antibody from the culture.

A further aspect of the invention relates to a use of a IgG1 antibody as defined hereinabove or as produced by the process as defined hereinabove, a nucleic acid molecule as defined hereinabove, a vector as defined hereinabove or a host as defined hereinabove for the preparation of a pharmaceutical composition for the prevention, treatment or amelioration of an epithelial tumor in a human. Another aspect of the invention relates to a method for the prevention, treatment or amelioration of an epithelial tumor in a human, said method comprising the step of administration of an effective amount of a pharmaceutical composition of the invention or as produced according by the process set forth above. The person skilled in the art, in particular the attending physician can evaluate the successful treatment of the patient in need of administration of the bispecific molecule/bispecific single chain antibody of the invention. Accordingly, the administration scheme as well as the dosage and the administration time may be assessed by said person skilled in the art: A corresponding "amelioration" and/or "treatment" to be assessed is defined below.

The most preferred mode of administration is an intravenous administration over a given time/time period. While the IgG1 antibody as defined herein may be administered per alone, preferred is administration in a pharmaceutically acceptable carrier. Examples of suitable pharmaceutical carriers are well known in the art and include phosphate buffered saline solutions, water, liposomes, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Preparations for parenteral administration include sterile aqueous or non-aqueous solutions, and suspensions. Examples of non-aqueous solvents are propylene glycol, polyethylene glycol, and injectable organic esters such as ethyl oleate. Aqueous carriers include water, aqueous solutions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the composition might comprise proteinaceous carriers, like, e.g., serum albumine or immunoglobuline, preferably of human origin. It is envisaged that the co-therapy might comprise, in addition to the proteinaceous IgG1 antibody further biologically active agents, depending on the intended use of the pharmaceutical composition. Such agents might be agents acting on the gastro-intestinal system, agents acting as cytostatica, agents preventing hyperurikemia, agents inhibiting immune reactions (e.g. corticosteroids, FK506), drugs acting on the circulatory system and/or agents such as T-cell co-stimulatory molecules or cytokines known in the art. Preferably, the IgG1 antibody as defined herein is formulated in a buffer, a stabilizer and a surfactant. The buffer may be a phosphate, citrate, succinate or acetate buffer. The stabilizer may be (an) amino acid(s) and/or a sugar. The surfactants may be detergents, PEGs, or the like. More preferably, the IgG1 antibody as defined herein is formulated in citrate, lysine, trehalose and Tween 80. As a diluent for said pharmaceutical composition, isotonic saline and Tween 80 is preferred.

The term "amelioration" as used herein refers to an improvement or a moderation in the severity of a disease, i.e. an epithelial tumor. For example, such an amelioration may be the achievement of a stable disease—or even more preferred—a shrinkage of the epithelial tumor(s), i.e. a minimal, partial response or complete response, due to the administration of the pharmaceutical compositions of the invention. "Stable disease" refers to a disease state in which no or no significant tumor progression/growth can be observed or detected by clinical and/or histological diagnostic methods. For example, a shrinkage of the tumor greater than 50% shrinkage of the sum of cross-sectional areas of index lesions may be considered as a "partial response". A "complete response" denotes a state in which no lesion(s) can be detected any more after treatment. A response with a tumor shrinkage between stable disease and partial response may be considered as a minimal response. For instance, a 20%, 25% or 30% shrinkage of the sum of cross-sectional areas of index lesions may be referred to as a minimal response.

The term "amelioration" as used herein encompasses also a reduction of the number of epithelial tumors. It furthermore denotes the prevention/slowdown of tumor progression. Moreover, an improvement of the overall survival of treated tumor patients in comparison to non-treated tumor patients may be considered as an "amelioration" as used herein. This applies mutatis mutandis to an improvement of the progression-free survival or the relapse-free survival of treated tumor patients as compared to non-treated tumor patients. In addition, the term "amelioration" can also refer to a reduction of the intensity of the symptoms of an epithelial tumor, resulting e.g. in an improvement of the quality of life of the treated tumor patients.

The term "prevention of an epithelial tumor" as used herein is to be understood as follows: After surgical removal of the primary epithelial tumor(s) from a human patient and/or after chemotherapeutic or radiological treatment of the primary epithelial tumor(s), it may be the case that not all tumor cells could be eliminated from the body. However, these remaining tumor cells may give rise to recurrent cancer, i.e. local recurrence and/or metastases in the patient. Metastasis is a frequent complication of cancer, yet the process through which cancer cells disseminate from the primary tumor(s) to form distant colonies is poorly understood. Metastatic cancers are almost without exception uncurable raising the necessity for new therapeutic modalities. The pharmaceutical composition of the invention can be used to kill these disseminated tumor cells in order to prevent the formation of secondary tumors (originating from the tumor cells remaining in the body after primary therapy). In this way, the pharmaceutical composition helps to prevent the formation of local recurrence and/or metastases in tumor patients.

The success of the anti-tumor therapy may be monitored by established standard methods for the respective disease entities, e.g. by computer-aided tomography, X-ray, nuclear magnetic resonance tomography (e.g. for National Cancer Institute-criteria based response assessment (Cheson (1999), J. Clin. Oncol.; 17(4):1244]), positron-emission tomography scanning, endoscopy, Fluorescence Activated Cell Sorting, aspiration of bone marrow, pleural or peritoneal fluid, tissue/histologies, and various epithelial tumor specific clinical chemistry parameters (e.g. soluble CEA concentration in serum) and other established standard methods may be used. In addition, assays determining T cell activation may be used; see e.g. WO99/054440. Statistics for the determination of overall survival, progression-free survival or relapse-free survival of treated tumor patients in comparison to non-treated tumor patients may also be used.

Preferably, said epithelial tumor is a gastrointestinal adenocarcinoma, a breast adenocarcinoma or a lung adenocarcinoma. Said gastrointestinal adenocarcinoma is more preferably a colorectal, pancreatic, an oesophageal or a gastric adenocarcinoma.

Even more preferred, said pharmaceutical composition of the invention is for the treatment of progressive tumors, late stage tumors, tumor patients with high tumor load/burden, metastatic tumors, or tumor patients with a CEA serum concentration higher than 100 ng/ml. Said CEA serum concentration may be determined e.g. by ELISA.

In another preferred embodiment of the uses or methods of the invention, said pharmaceutical composition as defined hereinabove is suitable to be administered in combination with an additional drug, i.e. as part of a co-therapy. In said co-therapy, an active agent may be optionally included in the same pharmaceutical composition as the IgG1 antibody, or may be included in a separate pharmaceutical composition. In this latter case, said separate pharmaceutical composition is suitable for administration prior to, simultaneously as or following administration of said pharmaceutical composition comprising the IgG1 antibody. The additional drug or pharmaceutical composition may be a non-proteinaceous compound or a proteinaceous compound.

Preferably, said proteinaceous compound or non-proteinaceous compound may be administered simultaneously or non-simultaneously with a IgG1 antibody as defined hereinabove, a nucleic acid molecule as defined hereinabove, a vector as defined as defined hereinabove, or a host as defined as defined hereinabove. Preferably, said subject to be treated is a human.

In a further aspect, the invention relates to a kit comprising a IgG1 antibody as defined hereinabove, a nucleic acid molecule as defined hereinabove, a vector as defined hereinabove, or a host as defined hereinabove.

These and other embodiments are disclosed and encompassed by the description and Examples of the present invention. Recombinant techniques and methods in immunology are described e.g. in Sambrook et al. Molecular Cloning: A Laboratory Manual; Cold Spring Harbor Laboratory Press, 3.sup.rd edition 2001; Lefkovits; Immunology Methods Manual; The Comprehensive Sourcebook of Techniques; Academic Press, 1997; Golemis; Protein-Protein Interactions: A Molecular Cloning Manual; Cold Spring Laboratory Press, 2002. Further literature concerning any one of the antibodies, methods, uses and compounds to be employed in accordance with the present invention may be retrieved from public libraries and databases, using for example electronic devices. For example, the public database "Medline", available on the Internet, may be utilized, for example under www.ncbi.nlm. nih.gov/PubMed/medline.html. Further databases and addresses, such as www.ncbi.nim.nih.gov/, www.infobioaen.fr/, www.fmi.ch/bioloqv/research tools.html, www.tiqr.orQ/. are known to the person skilled in the art and can also be obtained using, e.g., www.lvcos.com. For tumor-related topics see e.g. www.nih.gov or www.dkfz.de.

The Figures show:

FIG. 1: Schematic representation of an IgG molecule comprising VH, $C_H1$, hinge, $C_H2$, $C_H3$, VL and $C_L$ regions. The CDRs of the VH and VL regions are indicated as black boxes.

Figure 2:
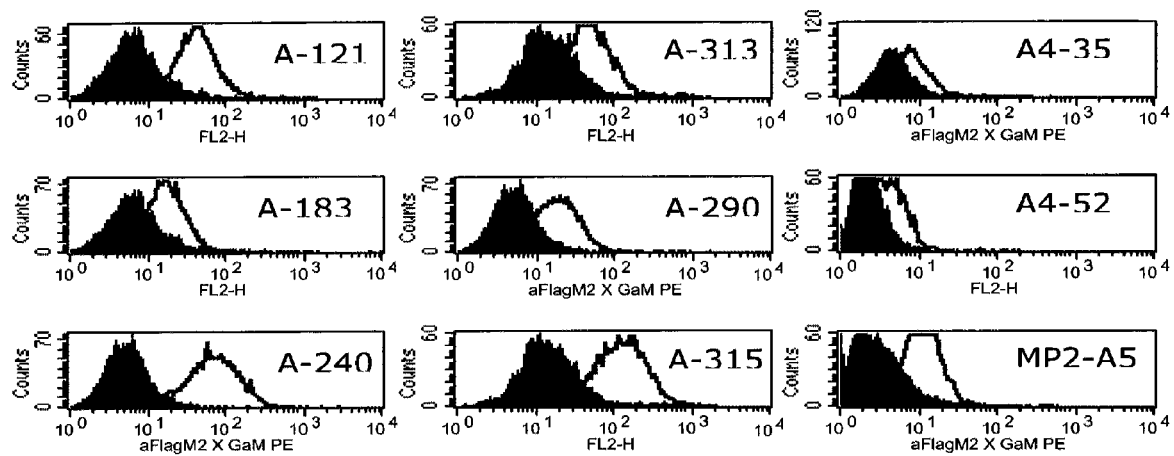

FIG. 2: Flow cytometric analysis of periplasmic preparations containing Flag-tagged scFv protein fragments specific for CEA from selected clones. Each of the scFv consists of the murine A5B7 VH region and a human VL region, as described in Example 3. Periplasmic preparations of soluble scFv protein fragments were added to 100,000 to 200,000 CEA-transfected CHO cells. For detection a monoclonal anti-Flag antibody was used followed by a PE-labeled polyclonal anti-mouse antibody. ScFvs binding to cells was measured by an increase in fluorescence intensity as compared to cells that were incubated with PBS alone. Fluorescence intensity is blotted on the X-axis, the number of events is blotted on the Y-axis. The negative control (PBS and detection reagents) is shown as filled curve, the respective scFvs are shown as grey lines. Shifting to the right indicates positive binding to the cells. All of the scFvs, i.e. A-121, A-183, A-240, A-313, A-290, A-315, A4-35, A4-52 and MP2-A5, bind to membrane-bound CEA on CHO cells.

Figure 3:
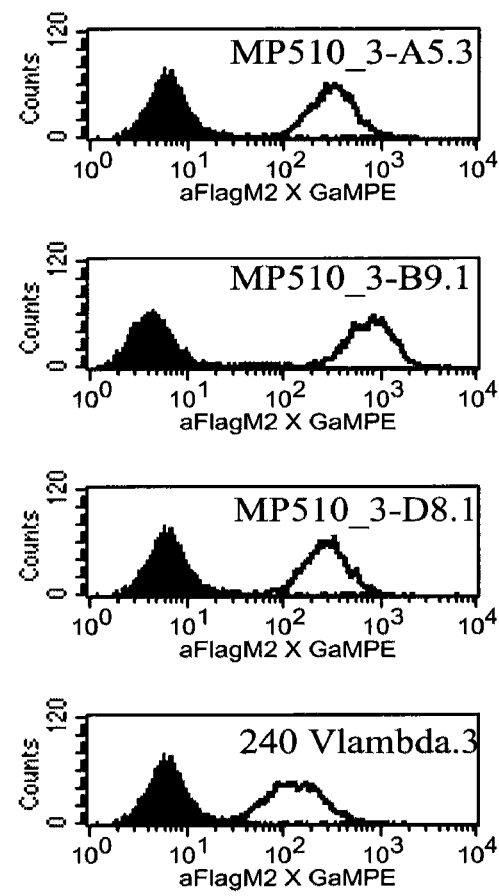

FIG. 3: Flow cytometric analysis of periplasmic preparations containing Flag-tagged scFv protein fragments specific for CEA from selected clones. Each of these scFvs consists of a humanized VH region and the human VL region A240, as described in Example 4. Periplasmic preparations of soluble scFv protein fragments were added to 100,000 to 200,000

CEA-transfected CHO cells. Detection was performed by a monoclonal anti-Flag antibody followed by a PE-labeled polyclonal anti-mouse antibody. ScFvs binding to cells was measured by an increase in fluorescence intensity as compared to cells that were incubated with PBS alone. Fluorescence intensity is blotted on the X-axis, the number of events is blotted on the Y-axis. The negative control (PBS and detection reagents) is shown as filled curve, the respective scFvs are shown as grey lines. Shifting to the right indicates positive binding to the cells. The humanized scFv constructs MP510_3-A5.3, MP510_3-B9.1, and MP510_3-D8.1 bind to membrane-bound CEA on CHO cells. 240 Vlambda.3 is a scFv consisting of the murine A5B7 VH region and the human VL A-240 region. This construct shows also CEA-binding activity.

Figure 4:
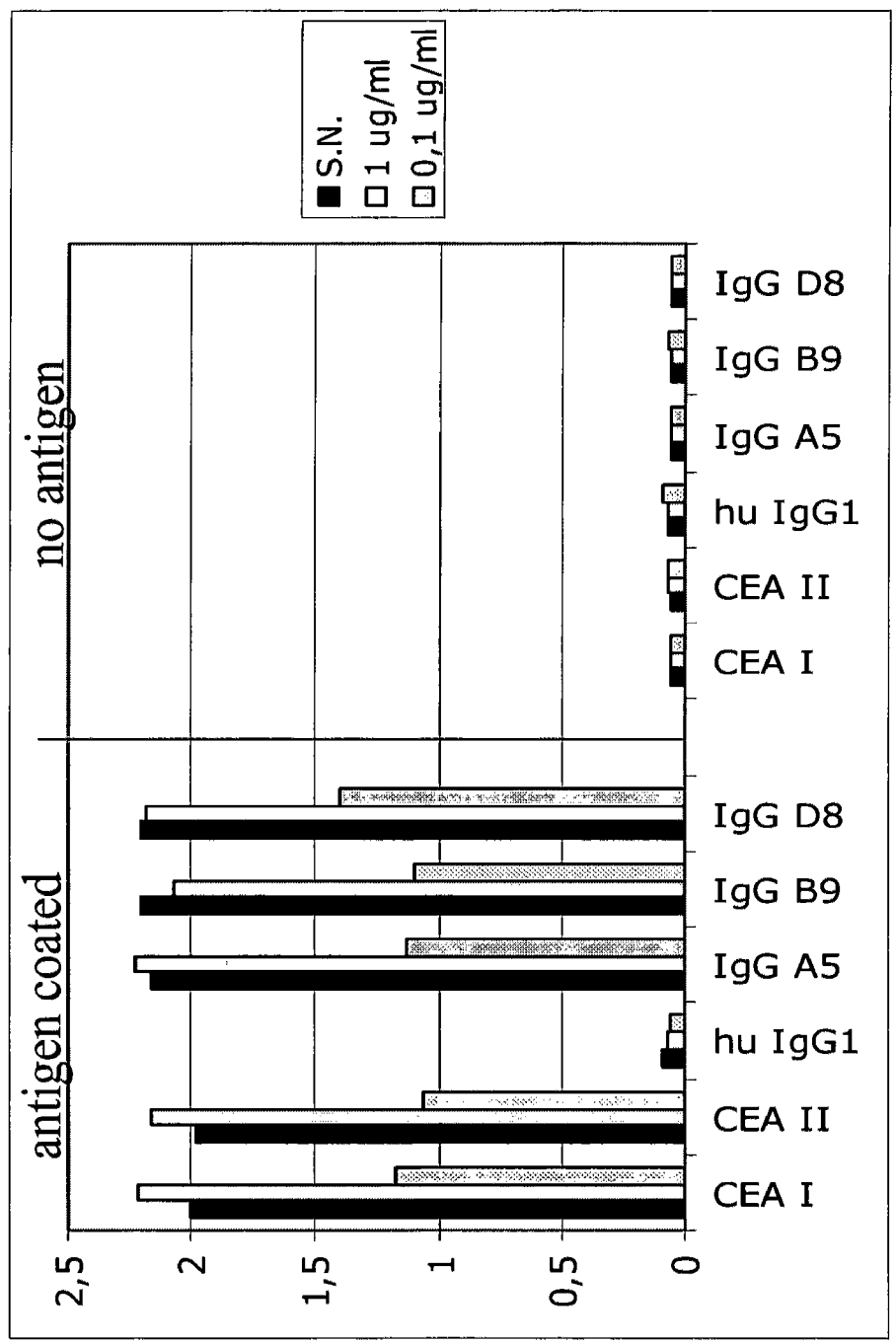

FIG. 4: ELISA analysis of purified human IgG1 versions of the humanized antibodies A5, B9, D8 and the human IgG1 versions of antibodies CEA I and CEA II as well as antibody-containing culture supernatants. An irrelevant human IgG1 antibody was included as a negative control. Antibody binding was tested on immobilized CEA antigen—and for demonstration of CEA specificity also in the absence of coated CEA antigen. Culture supernatant, 10 ug/ml and 1 ug/ml antibody solutions were added to the +/−antigen coated wells blocked with BSA. Detection was performed by peroxidase labeled polyclonal human IgG antibody (Jackson ImmunoResearch). The signals were measured after appropriate incubation with ABTS solution. Signal strength is plotted on the Y axis. Specific binding of the antibodies CEA I and CEA II as well as the humanized antibodies IgG1 A5, IgG1 B9 and IgG1 D8 to immobilized human CEA antigen could be demonstrated in this experiment.

Figure 5A:
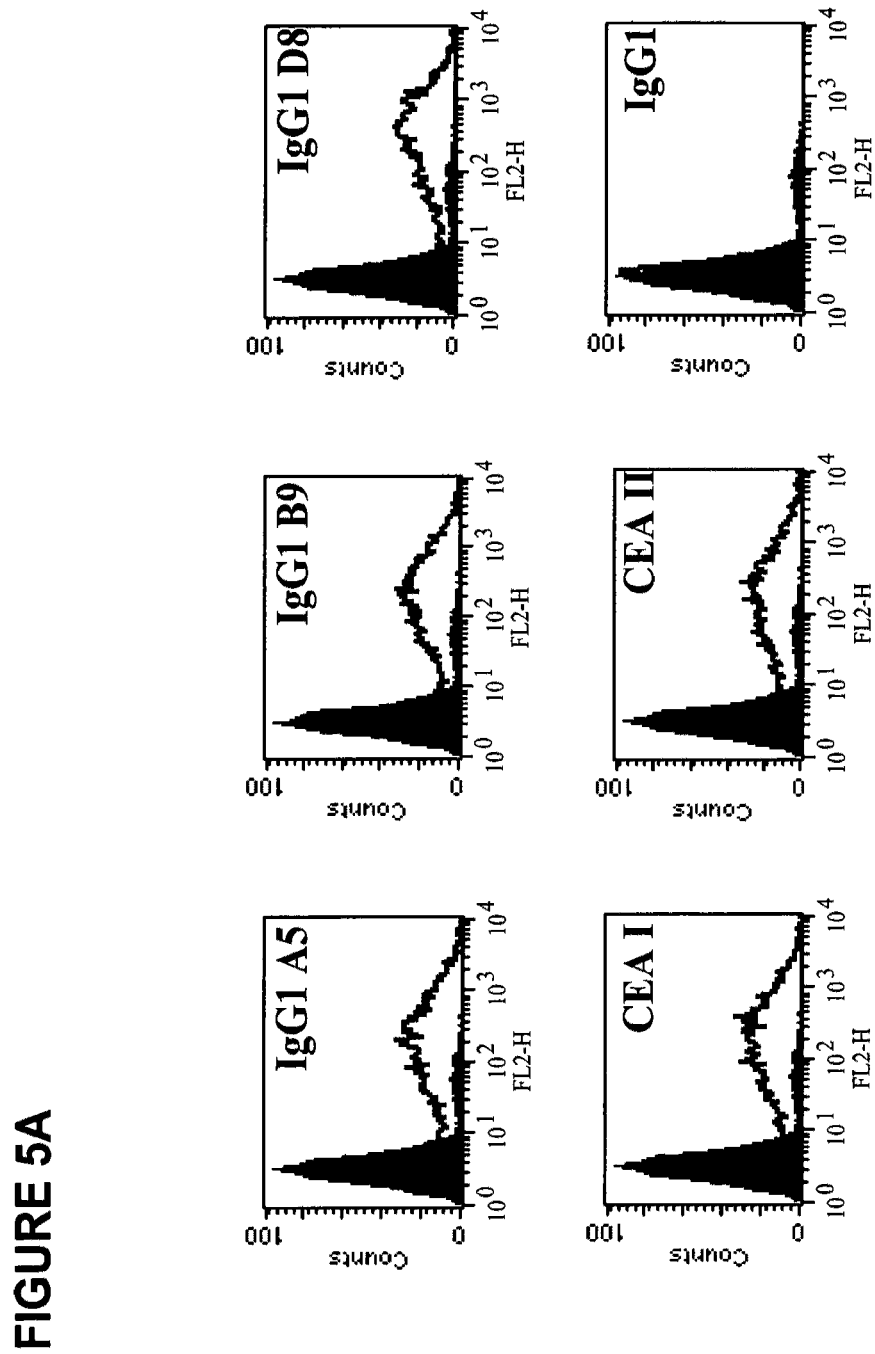
Figure 5B:
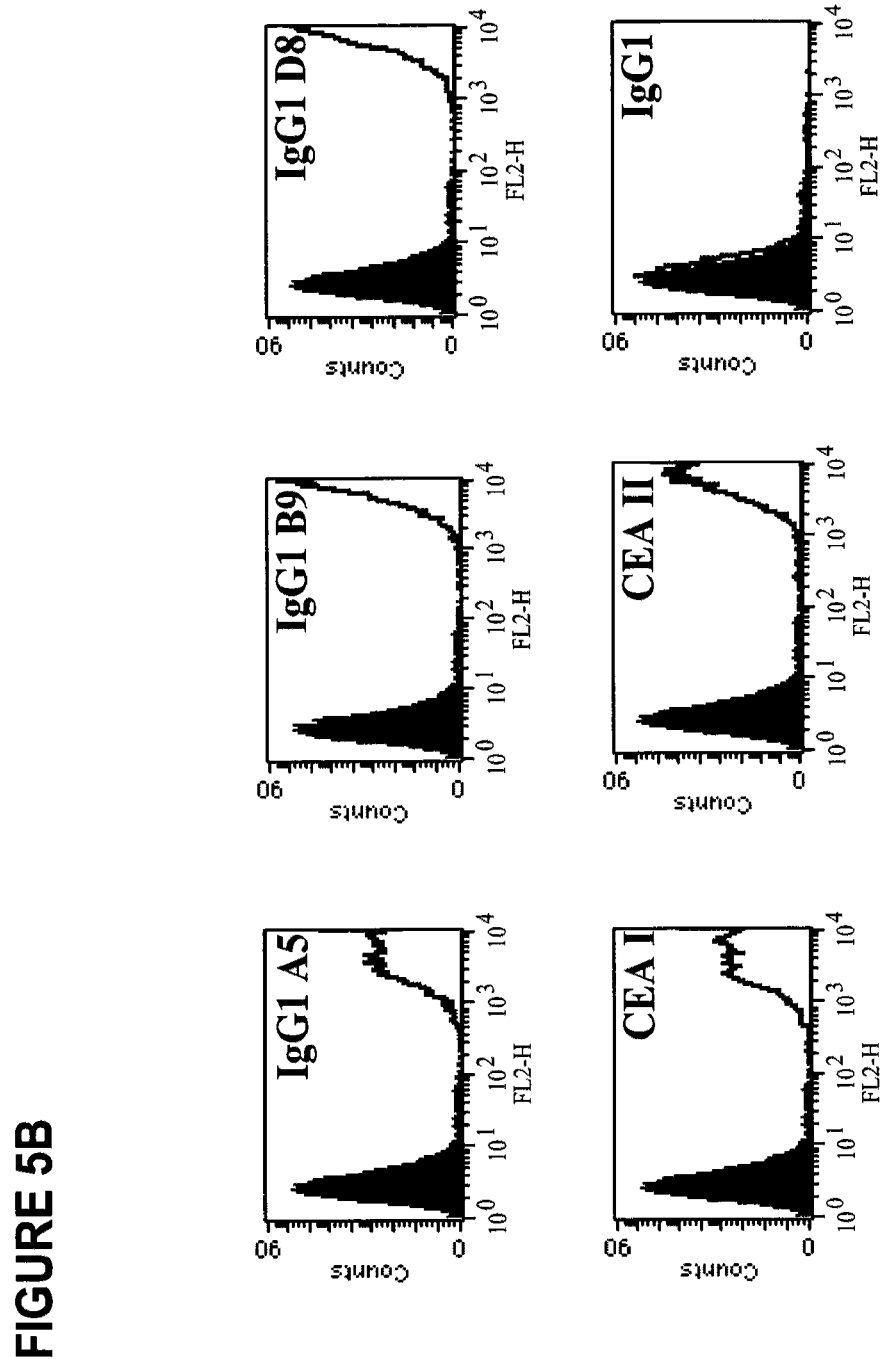
Figure 5C:
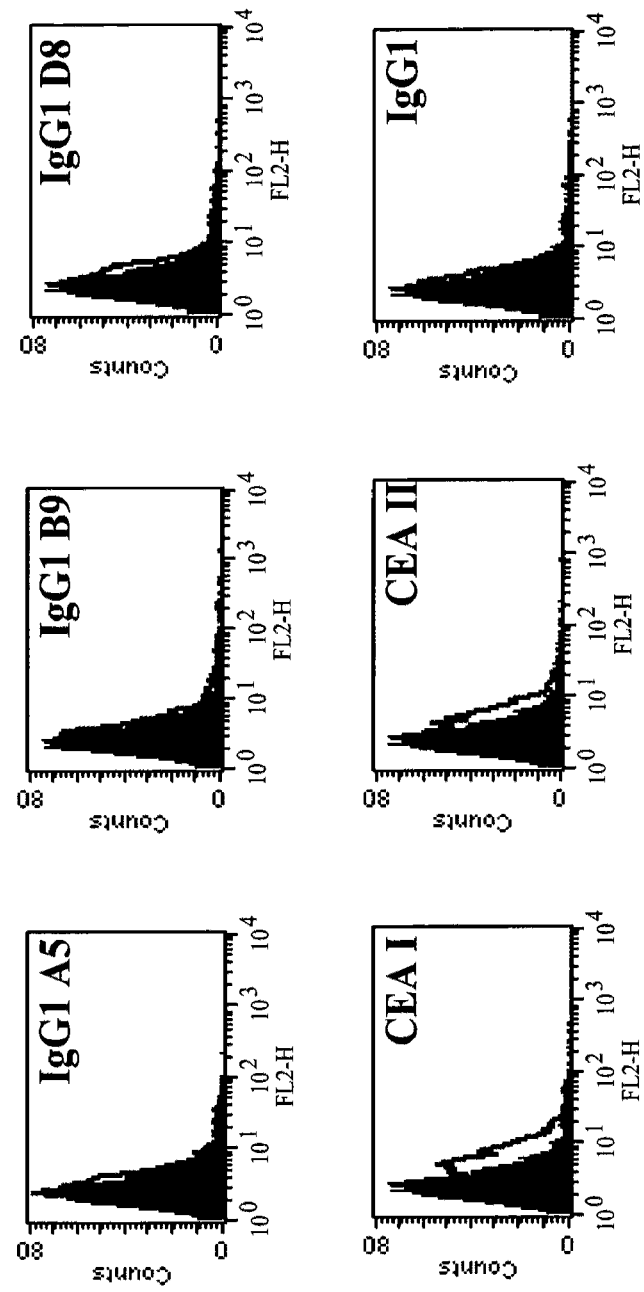

FIG. 5: Flow cytometric analysis of purified CEA antibodies and the respective negative control (see FIG. 4) using concentrations of 10 ug/ml of antibody. Antibody samples were added to 100,000 to 200,000 CEA positive Kato III cells (A), CEA-transfected CHO cells (B) and CEA-negative CHO cells (C). Detection was performed by a biotinylated polyclonal anti-human IgG antibody (DAKO) followed by PE-labeled Streptavidine (Jackson ImmunoResearch). Antibody binding to cells was measured by an increase in fluorescence intensity as compared to cells that were incubated with the respective isotype control. Fluorescence intensity is blotted on the X-axis, the number of events is blotted on the Y-axis. The negative control (PBS and detection reagents) is shown as filled curve, the respective antibodies are shown as grey lines. Shifting to the right indicates positive binding to the cells. Specific binding of the antibodies CEA I and CEA II as well as the humanized antibodies IgG1 A5, IgG1 B9 and IgG1 D8 to human CEA antigen on cells could be demonstrated in this experiment.

Figure 6A:
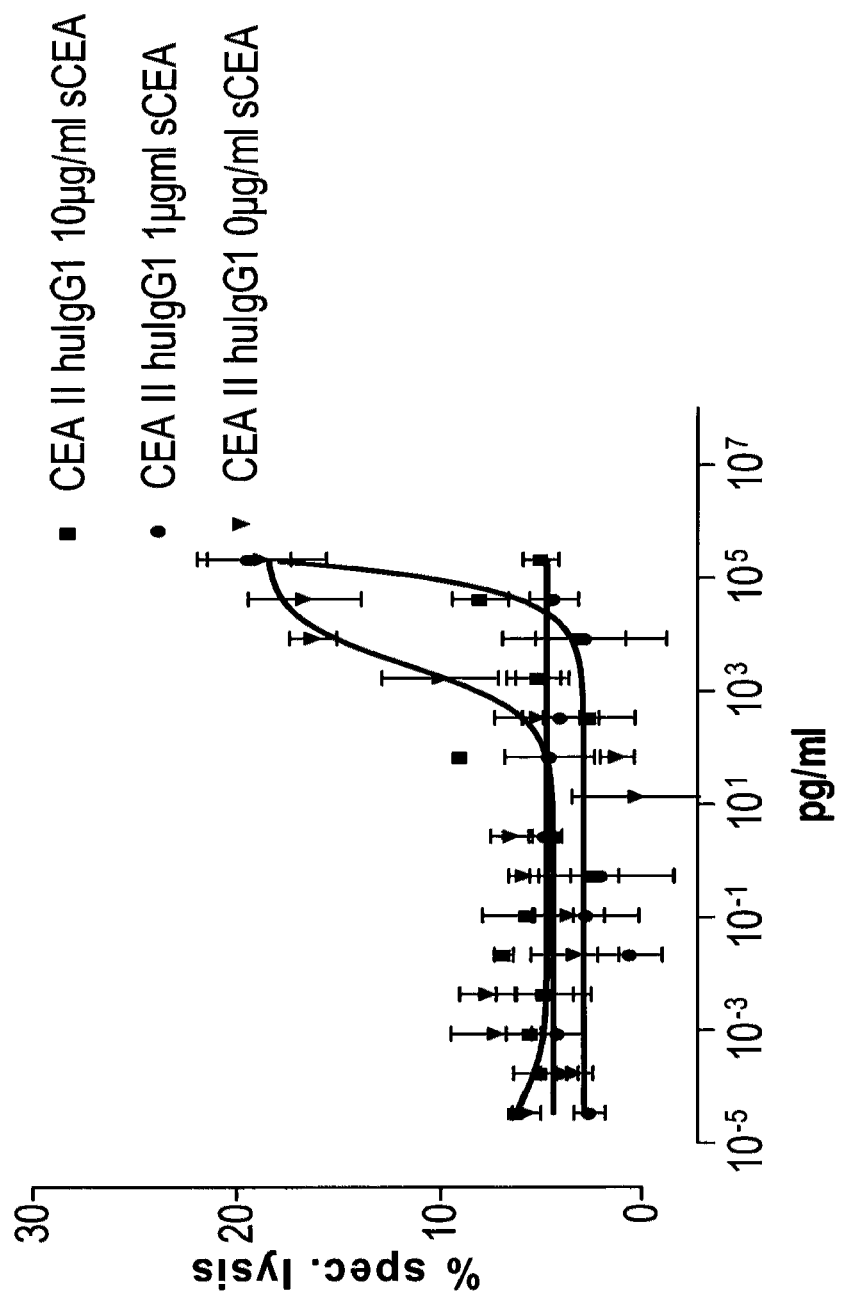
Figure 6B:
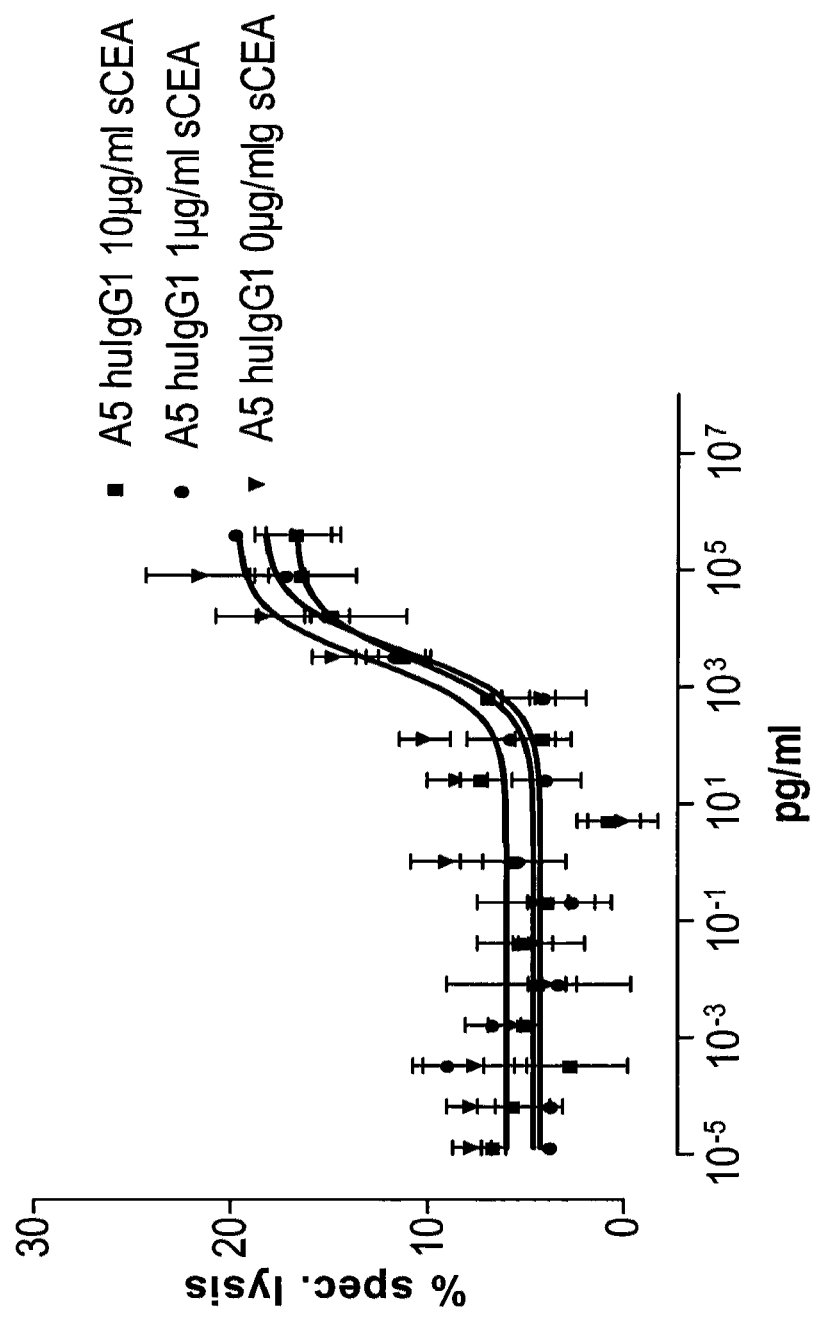

FIG. 6: Cytotoxicity analysis (ADCC assay) of purified human IgG1 versions of the humanized antibodies A5, B9, D8 and the human IgG1 version of antibody CEA II. Target cells (CEA transfected CHO cells) were labeled with chromium 51 and incubated with decreasing amounts of the respective antibodies in the presence of human PBMCs for 18 h and in the presence of two concentrations of soluble human CEA antigen (10 and 1 ug/ml, respectively). Two representative results are shown: CEA II antibody in FIG. 6A and IgG1 A5 antibody in FIG. 6B. These two examples clearly illustrate the absence of an inhibitory cytotoxic effect of soluble CEA for the humanized antibody IgG1 A5 (FIG. 6B), whereas the cytolytic activity of CEA II antibody is dramatically reduced in the presence of 1 ug/ml of soluble CEA and is further reduced below detection in the presence of 10 ug/ml soluble CEA (FIG. 6A).

Figure 7:
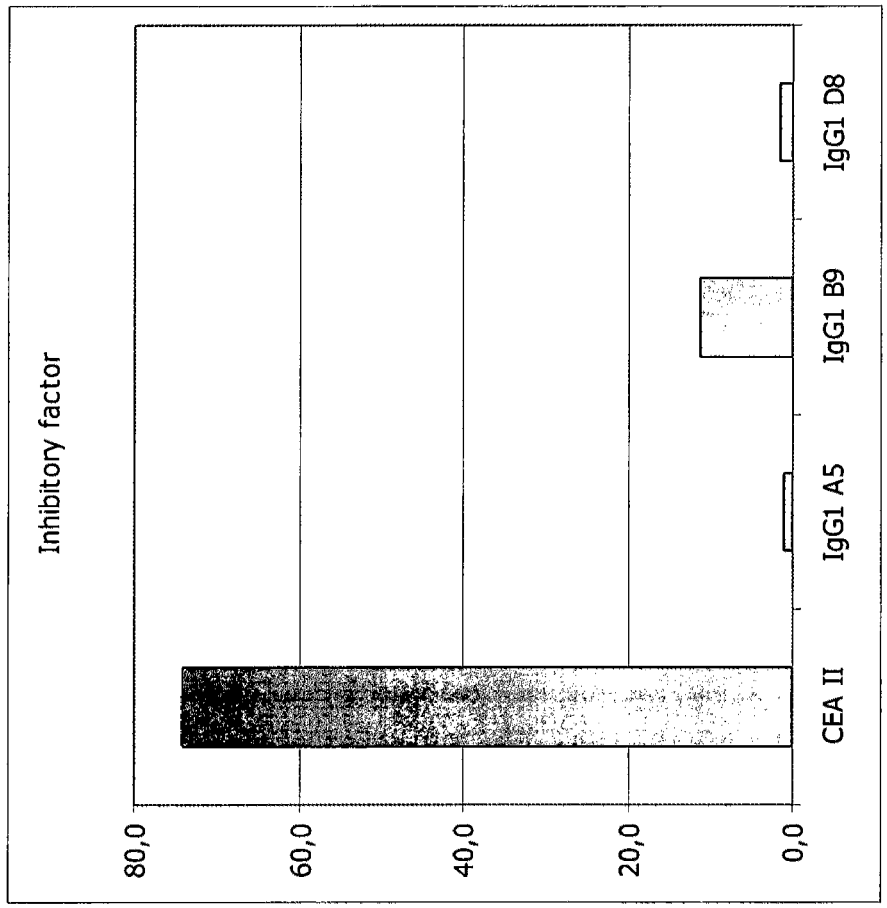

FIG. 7: Cytolytic inhibition in the presence of soluble CEA antigen was converted into an "inhibitory factor". This factor is defined as the EC50 in the presence of 10 and 1 ug/ml soluble CEA in the ADCC assay divided by the EC50 in the absence of soluble CEA. It can clearly be shown that CEA II has a dramatically decreased cytolytic activity in the presence of soluble CEA antigen, whereas IgG1 A5-, IgG1 B9- and IgG1 D8-mediated cytolytic activity towards tumor cells is resistant to soluble CEA.

The following Examples illustrate the invention:

EXAMPLE 1

Generation of CHO Cells Transfected with Human CEA (Carcinoembryonic Antigen-Related Cell Adhesion Molecule 5; CEACAM5)

Kato III cells (human gastric carcinoma cell line; ATCC HTB-103), which are CEA positive were used to obtain the total RNA that was isolated according to the instructions of the kit manual (Qiagen, RNeasy Mini Kit). The obtained RNA was used for cDNA synthesis by random-primed reverse transcription. For cloning of the full length sequence of the CEA antigen, the following oligonucleotides were used: 5' CEACAM5 EcoRI GAATTCGCCACCATG-GAGTCTCCCTCGGCCCC (SEQ ID NO. 35) and 3' CEACAM5 Sal I GTCGACCTATATCAGAGCAACCCC (SEQ ID NO. 36). A PCR (denaturation at 93.degree. C. for 5 min, annealing at 58.degree. C. for 1 min, elongation at 72.degree. C. for 1 min for the first cycle; denaturation at 93.degree. C. for 1 min, annealing at 58.degree. C. for 1 min, elongation at 72.degree. C. for 1 min for 30 cycles; terminal extension at 72.degree. C. for 5 min) was used to amplify the coding sequence. The PCR product was subsequently digested with EcoRI and SalI, ligated into the appropriately digested expression vector pEF-DHFR, and transformed into E. coli. The isolated plasmid DNA was sequenced and compared with the established nucleotide sequence of CEACAM5 (NM.sub.--004363 at the National Center for biotechnology information, www.ncbi.nlm.nih.gov/; SEQ ID NO. 37) The aforementioned procedures were carried out according to standard protocols (Sambrook, Molecular Cloning; A Laboratory Manual, Cold Spring Harbour Laboratory Press, Cold Spring Harbour, N.Y. (1989; 2001). The clone with the verified nucleotide sequence was transfected into DHFR deficient CHO cells for eukaryotic expression of the construct. Eukaryotic protein expression in DHFR deficient CHO cells was performed as described in Kaufmann (Kaufmann R. J., Methods Enzymol. 185 (1990), 537-566). Gene amplification of the construct was induced by increasing concentrations of MTX to a final concentration of up to 20 nM MTX. The transfected cells were then tested for expression of CEA antigen using an FACS assay. For that purpose, a number of 2.5.times.10.sup.5 transfected cells were incubated with the murine monoclonal antibody COL-1 (Neomakers; Fremont, Calif., USA) in a concentration of 5 μg/ml. The binding of the antibody was detected with a R-Phycoerythrin-conjugated affinity purified F(ab')2 fragment, goat anti-mouse IgG, Fc-gamma fragment specific antibody, diluted 1:100 in 50 μl PBS with 2% FCS (obtained from Dianova, Hamburg, Germany). Cells were analyzed by flow cytometry on a FACS-Calibur (Becton Dickinson, Heidelberg). FACS staining and measuring of the fluorescence intensity were performed as described in Current Protocols in Immunology (Coligan, Kruisbeek, Margulies, Shevach and Strober, Wiley- Interscience, 2002). As a result, the transfectants demonstrated a clearly positive staining for the human CEA antigen.

EXAMPLE 2

Generation and Characterization of IgG1 Antibodies Derived from Murine Monoclonal Antibodies (mAb) A5B7 and T84.66

In order to express full IgG antibody molecules, two vectors have been generated. One of these vectors encoded the heavy chain, whereas the other encoded the light chain. The full IgG molecules have been derived from murine monoclonal antibodies A5B7 (Chester, Int. J. Cancer 57 (1994), 67-72; Harwood, loc. cit.) and T84.66 (Neumaier, Cancer Res. 50 (1990), 2128-34). The respective sequences were extracted from the literature and the corresponding V-regions were gene-synthesized at Entelechon, Germany. These synthesized DNA fragments were used as templates in the following PCR steps.

1. Cloning of Murine Light Chains Based on Antibody CEA I (A5B7) and CEA II (T84.66)

To generate suitable terminal restriction sites, the DNA fragment encoding the VL region of antibody CEA I (A5B7) was reamplified by PCR, resulting in Vkappa fragments with a Bsu36I-site at the 5'-end and a Xho I-site at the 3'-end. The primers 5'-VL CEA I Bsu36I (5'-TTCTCTCCTTAGGT-GTCCACTCCGACATTGAGCTCACC CAGTCTCC-3') (SEQ ID NO. 81) and 3'-VL CEA I Xho I (5'-CATGCACTC-GAG CTTGGTCCCTCCACCGAACGTC-3') (SEQ ID NO. 82) were used for this purpose. This fragment was then subcloned into a pBS-derived plasmid containing a human leader sequence and a murine Ckappa (Hieter et al. 1980 Cell 22: 197-207) region by Bsu36I and XhoI, thereby adding a mammalian leader sequence and a murine Ckappa constant region. Utilizing EcoRI and SalI, CEA I VL-Ckappa DNA was excised from said vector and subcloned into the eukaryotic expression vector pEF-ADA derived from the expression vector pEF-DHFR (Mack et al. (1995) Proc. Natl. Acad. Sci. USA. 92, 7021-5) by replacing the cDNA encoding murine dihydrofolate reductase (DHFR) with that encoding murine adenosine deaminase (ADA).

The same procedure was performed with the VLs of antibody CEA-II (T84.66), accordingly, but using different specific primers:

For CEA II (T84.66):

(SEQ ID NO. 83)
5'-VL CEA II Bsu36I
(5'- TTCTCTCCTTAGGTGTCCACTCCGACATTGTGCTGACCCAAT
CTCC-3')
and (SEQ ID NO. 84)
3'-VL CEA II Xho I
(5'-CATGCACTCGAGCTTGGTCCCCCCACCGAACGTG-3').

As a result of this experiment, murine light chains based on antibodies CEA I (A5B7), and CEA II (T84.66) have been generated. The amino acid sequence of the VH region of mAb A5B7 is shown in SEQ ID NO. 8, whereas the VL region of CEA I (mAb A5B7) is shown in SEQ ID NO. 10. The amino acid sequence of the VH region of CEA II (mAb T84.66) is shown in SEQ ID NO. 12, whereas the VL region of mAb T84.66 is shown in SEQ ID NO. 14.

2. Cloning of Murine Heavy Chain Variable Domains

From the murine VH regions of CEA I (A5B7) and CEA II (T84.66), the variable region of the heavy chain was reamplified by PCR, generating Bsu36I restriction sites at both ends. For CEA I (A5B7) the combination of the following two primers was used: 5'-primer 5'-CEA I VH-Bsu36I (5'-TTCTCTCCTTAGGTGTCCACTCCCAG-GTCCAACTGCAGGAGTCAGG-3') (SEQ ID NO. 87) and 3'-primer 3'-CVH-Bsu36I (5'-GACTCACCTGAG-GAGACGGTGACCGT GGTCCCTTGG-3') (SEQ ID NO. 88), for CEA II (T84.66) the combination of the following two primers was used: 5'-primer 5'-CEA II VH-Bsu36I (5'-TTCTCTCCTTAGGTGTCCACTCCGAGGT-TCAGCTGCAGCAGTCTGG-3') (SEQ ID NO. 89) and 3'-primer 3'-CEA II VH-Bsu36I (5'-GACTCACCTGAG-GAGACGGTGAC TGAGGTTCCTTGACC-3') (SEQ ID NO. 90).

The resulting DNA-fragments were then subcloned using these restriction sites into the eukaryotic expression vector pEF-DHFR already containing a eukaryotic leader sequence and a DNA-fragment encoding the human IgG1 heavy chain constant region (see Raum, Cancer Immunol Immunother. 50 (2001):141-50). The heavy chain variable regions were thus inserted between the leader and the heavy chain constant region.

As a result of this experiment, vectors encoding murine heavy chain variable domains linked to said human IgG1 constant region have been generated. The amino acid sequence of the VH region of mAb A5B7 is shown in SEQ ID NO. 8, whereas the VL region of CEA I (mAb A5B7) is shown in SEQ ID NO. 10. The amino acid sequence of the VH region of CEA II (mAb T84.66) is shown in SEQ ID NO. 12, whereas the VL region of mAb T84.66 is shown in SEQ ID NO. 14.

3. Expression of the Full IgG Proteins

In order to express full IgG1 antibodies, a plasmid encoding for one (murine) light chain and a plasmid encoding for one heavy chain (murine VH/human IgG1 constant region) generated as set forth above were co-transfected into HEK cells according to standard protocols for transient protein expression and the cells were cultured to allow the expression and production of the immunoglobulins into the culture medium. In this manner, huIgG1 CEA I derived from antibody CEA I (A5B7) and huIgG1 CEA II derived from antibody CEA II (T84.66) were produced. Said huIgG1 antibody constructs consist of a murine variable (V) region derived from CEA I (A5B7) or CEA II (T84.66), a murine constant (C) light chain (Ckappa) region and human constant heavy chain CH1, CH2, CH3 and hinge regions (the human IgG1 heavy chain constant region is described in Raum, Cancer Immunol Immunother. 50 (2001): 141-50). After the respective production period, the supernatants were harvested and the human immunoglobulins were isolated via Protein A chromatography according to standard protocols for the purification of immunoglobulins. Culture supernatants, as well as purified immunoglobulins were then used for further characterization experiments.

4. Characterization of the IgG1 Antibodies Generated Above 4.1 Binding to Immobilized Soluble CEA (sCEA) Antigen Culture supernatants of heavy+light chain double transfectants as well as the corresponding preparations of purified antibody were tested for binding on immobilized soluble CEA (sCEA; Abcam, Ltd, Cambridge UK) antigen by ELISA according to standard procedures. The antibodies huIgG1 CEA I derived from antibody CEA I (A5B7) and huIgG1 CEA II derived from antibody CEA II (T84.66) generated as set forth above showed distinct binding to the immobilized sCEA antigen as compared to the negative control and no binding in an equivalent setting with the difference that no sCEA antigen was coated (as shown in FIG. 4).

4.2 Binding to Membrane Bound CEA

Purified antibody preparations of huIgG1 CEA I derived from antibody CEA I (A5B7) and huIgG1 CEA II derived from antibody CEA II (T84.66) were tested by FACS analysis on the CEA-positive gastric cancer cell line Kato III, CEA-transfected CHO-cells and untransfected CHO-cells.

$2 \times 10^5$ cells were incubated with purified antibody preparations (typically 10-20 μg/ml). Detection of cell-bound antibodies was carried out with FITC labeled anti mouse IgG- or anti human IgG antibodies (typically 10-20 μg/ml). Incubation was carried out for 20-40 min. on ice.

huIgG1 CEA I derived from antibody CEA I (A5B7) and huIgG1 CEA II derived from antibody CEA II (T84.66) showed distinct binding to the CEA positive cells. None of the IgG1 antibodies showed binding to untransfected CHO cells. IgG-controls were negative on Kato III cells, CHO/CEA-cells and untransfected CHO cells (as shown in FIGS. 5A, B and C).

4.3 Antibody Dependent Cellular Cytotoxicity (ADCC) Assay ($^{51}$Cr Release Assay)

For the $^{51}$Cr release assay, human peripheral blood mononuclear cells (PBMCs) as effector cells were isolated from healthy donors. The PBMCs were separated by Ficoll density gradient centrifugation with a subsequent 100×g centrifugation step. Unstimulated PBMCs ($5 \times 10^5$ cells) were added in a volume of 100 μl of RPMI 1640 medium with 10% FCS to each well of a flat bottomed microtiter plate and incubated overnight at 37° C. As target cells, CEA-transfected CHO cells have been used. Target cells were labeled for 2 h with $^{51}$Cr. Labeled target cells (50.000 cells) and antibodies in different concentrations (10 μg/ml-10 μg/ml) were added to the PBMCs and incubated for 18 h at 37° C. This assay has been carried out in the absence of soluble CEA (sCEA) antigen. Corresponding non-binding isotypes were used as negative controls. Specific lysis was calculated as ((cpm, experimental release)–(cpm, spontaneous release))/((cpm, maximal release)–(cpm, spontaneous release)). huIgG1 CEA I derived from antibody CEA I (A5B7) and huIgG1 CEA II derived from antibody CEA II (T84.66) proved to mediate significant cytotoxicity for the CEA positive CHO cells in this $^{51}$Cr release assay as compared to the negative control.

In a second cytotoxicity experiment, the antibody samples were pre-incubated with soluble CEA (sCEA) antigen for 20 min under agitation and then mixed with the labeled target cells and the human PBMCs. Otherwise, the assay has been performed as described above. Soluble CEA (sCEA) antigen has been used in different concentrations, i.e. 1 μg/ml and 10 μg/ml.

In the presence of soluble CEA, especially at the higher concentrations, huIgG1 CEA II derived from antibody CEA II (T84.66) showed reduced cytotoxic (ADCC) activity. In contrast, huIgG1 CEA I derived from antibody CEA I (A5B7) showed no significant decrease of cytotoxic activity as compared to the activity in the absence of soluble CEA. Thus, cytotoxicity against CEA positive tumor cells mediated by huIgG1 CEA I derived from antibody CEA I (A5B7) is resistant to soluble CEA.

In summary, it has been found that the cytotoxic activity (ADCC) directed against tumor cells of huIgG1 CEA I derived from antibody CEA I (A5B7) is resistant to even high concentrations of soluble CEA antigen. This finding is entirely unexpected in view of the fact that this IgG1 antibody binds to soluble CEA antigen. For example, when an IgG1 antibody construct derived from monoclonal antibody T84.66 has been tested, this antibody was highly sensitive to soluble CEA antigen, ie. the cytotoxic activity (ADCC) has been blocked by soluble CEA antigen. This antibody has also been found to be capable of binding to soluble CEA. In view of this, it was concluded that soluble CEA antigen prevents huIgG1 CEA II derived from antibody CEA II (T84.66) from exerting its antibody-mediated cytotoxic activity. In contrast, the IgG1 CEA I antibodies derived from antibody CEA I (A5B7) as defined herein are resistant to the presence of even high levels of soluble CEA in their cytotoxic activity towards tumor cells.

EXAMPLE 3

Selection of Human VL Regions

In order to provide for IgG1 antibodies with reduced immunogenicity when being administered to cancer patients, humanized IgG1 antibodies with resistance to soluble CEA antigen have been generated. In a first step, human VL regions with resistance to soluble CEA have been isolated. Thus, the aim of this experiment is the selection of human VL regions which can pair with the maternal, murine VH of monoclonal antibody (mAb) A5B7.

1. Biotinylation of Soluble Human CEA Antigen

For phage library selection, soluble CEA antigen was biotinylated. Biotinylation was accomplished in PBS containing 5% DMSO (Sigma) with a fifteenfold molar excess of EZ-Link Sulfo NHS-LC-LC-Biotin (Pierce) for 1 hour at room temperature in a sample mixer (Dynal). For the separation of free Biotin and biotinylated CEA antigen, the assay was excessively dialized against PBS according to standard protocols.

The retained bioactivity of the biotin-labeled CEA was confirmed in ELISA binding experiments.

2. Isolation of RNA from Human B-Cells 100 mL blood were taken from five healthy human donors. Peripheral blood mononuclear cells (PBMCs) were isolated by a ficoll-gradient according to standard methods. Total RNA was isolated from the isolated cells using the RNeasy® Midi Kit (QIAGEN) following the manufacturer's instructions. cDNA was synthesized according to standard methods (Sambrook, Cold Spring Harbor Laboratory Press 1989, 2001).

3. PCR-Amplification of Variable Light Chain Regions (VL-Regions)

For the isolation of light chain V-region DNA, RT-PCR was carried out using V-kappa-(5'-huVK1-SacI-2001 (5'-GAGC-CGCACG AGCCCGAGCT CCAGATGACC CAGTCTCC-3') (SEQ ID NO. 38), 5'-huVK2/4-SacI-2001 (5'-GAGCCG-CACG AGCCCGAGCT CGTGATGACY CAGTCTCC-3') (SEQ ID NO. 39), 5'-huVK3-SacI-2001 (5'-GAGCCGCACG AGCCCGAGCT CGTGWTGACR CAGTCTCC-3') (SEQ ID NO. 40), 5'-huVK5-SacI-2001 (5'-GAGCCGCACG AGCCCGAGCT CACACTCACG CAGTCTCC-3') (SEQ ID NO. 41), 5'-huVK6-SacI-2001 (5'-GAGCCGCACG AGCCCGAGCT CGTGCTGACT CAGTCTCC-3') (SEQ ID NO. 42), 3'-hu-Vk-J1-SpeI-BsiWI (5'-GACGACACTA GTTGCAGCCA CCGTACGTTT GATTTCCACC TTG-GTCC-3') (SEQ ID NO. 43), 3'-hu-Vk-J2/4-SpeI-BsiWI (5'-GACGACACTA GTTGCAGCCA CCGTACGTTT GATCTCCASC TTGGTCC-3') (SEQ ID NO. 44), 3'-hu-Vk-J3-SpeI-BsiWI (5'-GACGACACTA GTTGCAGCCA CCG-TACGTTT GATATCCACT TTGGTCC-3') (SEQ ID NO. 45), 3'-hu-Vk-J5-SpeI-BsiWI (5'-GACGACACTA GTTG-CAGCCA CCGTACGTTT AATCTCCAGT CGTGTCC-3') (SEQ ID NO. 46)) and V lambda (5'-huVL1a-SacI-2001

(GAG CCG CAC GAG CCC GAG CTC GTG TTG ACG CAG CCG CCC TC) (SEQ ID NO. 47), 5'-huVL1b-SacI-2001 (GAG CCG CAC GAG CCC GAG CTC GTG CTG ACT CAG CCA CCC TC) (SEQ ID NO. 48), 5'-huVL2-SacI-2001 (GAG CCG CAG GAG CCC GAG CTC GCC CTG ACT CAG CCT SCC TCC GT) (SEQ ID NO. 49), 5'-huVL4-SacI-2001 (ACC TGC GAG CTC GTG CTG ACT CAR YCMYCC TCT GC) (SEQ ID NO. 50), 5'-huVL5-SacI-2001 (ACC TGC GAG CTC GTG CTG ACT CAG CCR SCT TCC) (SEQ ID NO. 51), 5'-huVL6-SacI-2001 (ACC TGC GAG CTC ATG CTG ACT CAG CCC CAC TC) (SEQ ID NO. 52), 5'-huVL3/9-SacI-2001 (GAG CCG CAC GAG CCC GAG CTC GWG CTG ACT CAG CCA CCY TC) (SEQ ID NO. 53), 5'-huVL7/8-SacI-2001 (GAG CCG CAC GAG CCC GAG CTC GTG GTG ACY CAG GAG CCM TC) (SEQ ID NO. 54), 3'-hu-Vlam-BlnI-SpeI-2001 (CGT GGG ACT AGT CTT GGG CTG ACC TAG GAC GGT) (SEQ ID NO. 55), 3'-hu-Vlam2-BlnI-SpeI-2002: CGT GGG ACT AGT CTT GGG CTG ACC GAG GAC GGT) (SEQ ID NO. 56) primer sets.

RNA from human B-cells was transcribed into cDNA (as described above) and used as template DNA in PCR reactions. Per PCR reaction, one 5'-primer was combined with one 3'-primer. The number of different PCR reactions was determined by the number of possible combinations of 5'- and 3'-primers. The following PCR-program was used for amplification: Denaturation at 94° C. for 15 seconds, primer annealing at 52° C. for 50 seconds and primer extension at 72° C. for 90 seconds were performed over 40 cycles, followed by final extension at 72° C. for 10 minutes. Light chain DNA V-fragments were then isolated according to standard protocols.

4. Library Construction—Cloning of the Human VL Pool

A phage display library was generally constructed based on standard procedures, as for example disclosed in "Phage Display: A Laboratory Manual"; Ed. Barbas, Burton, Scott & Silverman; Cold Spring Harbor Laboratory Press, 2001.

The primers chosen for PCR amplification gave rise to 5'-SacI and 3'-SpeI recognition sites for the light chain V-fragments. Four ligation reactions were set up, each consisting of 400 ng of light chain fragments (SacI-SpeI digested, 2×kappa and 2×lambda) and 1400 ng of the phagemid pComb3H5BHis (SacI-SpeI digested; large fragment; this vector is described in the thesis dissertation of Dr. Ralf Lutterbüse. The four resulting antibody V-light chain pools were then each transformed into 300 µL of electrocompetent *Escherichia coli* XL1 Blue by electroporation (2.5 kV, 0.2 cm gap cuvette, 25 mF, 200 Ohm, Biorad gene-pulser) resulting in library sizes of kappa1: $2\times10^8$
kappa2: $6\times10^7$
lambda1: $9\times10^7$
lambda2: $6\times10^7$
independent clones.

Kappa (light chain) DNA-fragments from the different PCR amplifications were weighted for each ligation as follows: Each 5'-primer defines a specific group. Within these groups the 3'-primers define the subgroups. The kappa subgroups were weighted 1:2:1:1 corresponding to the primers 3'-hu-Vk-J1-SpeI-BsiWI: 3'-hu-Vk-J2/4-SpeI-BsiWI: 3'-hu-Vk-J3-SpeI-BsiWI: 3'-hu-Vk-J5-SpeI-BsiWI. The groups were weighted according to their germline distribution 1:1:1:0.2:0.2 corresponding to the primers 5'-huVK1-Sac-2001: 5'-huVK3-Sac-2001:5'-huVK2/4-Sac-2001:5'-huVK5-Sac-2001:5'-huVK6-Sac-2001.

Lambda (light chain) DNA-fragments from the different PCR amplifications were weighted for each ligation as follows: Each 5'-primer defines a specific group. Within these groups the 3'-primers define the subgroups. The lambda subgroups were weighted 3:1 corresponding to the primers 3'-hu-Vlam-BlnI-SpeI-2001: 3'-hu-Vlam2-BlnI-SpeI-2002.

The groups were weighted according to their germline distribution 1:1:2:2:2:3 corresponding to the primers 5'-huVL1a-SacI-2001:5'-huVL1b-SacI-2001:5'-huVL2-SacI-2001:5'-huVL4-SacI-2001+5'-huVL5-SacI-2001:5'-huVL6-SacI-2001+5'-huVL7/8-SacI-2001:5'-huVL3/9-SacI-2001.

After electroporation each transformed *E. coli* culture was incubated in SOC broth (Fluka) for phenotype expression. The two kappa cultures were combined as well as the two lambda cultures. The resulting kappa culture and the resulting lambda culture were then each incubated in 500 mL of SB selection medium containing 50 µg/mL carbenicillin and 2% w/v glucose overnight. The next day, cells were harvested by centrifugation and plasmid preparation was carried out using a commercially available plasmid preparation kit (Qiagen).

5. Construction of the Antibody Library—Human VL—Maternal VH

PCR was performed to amplify the maternal VH of mAb A5B7 from a vector containing said maternal VH. For amplification a PCR protocol according to standard procedures was followed using the 5'-primer 5'-AVH-XhoI (5'-GTC ACA CTC GAG TCA GGA GGA GGC TTG GTA C-3') (SEQ ID NO. 57) and the 3'-primer 3'-AVH-BstEII (5'-GTC ACA GGT GAC CGT GGT CCC TTG GCC CCA G-3' (SEQ ID NO. 58). After purification of the approximately 350 bp amplification product from an analytical agarose gel, the DNA fragment was cut with the restriction enzymes BstEII and XhoI. The phagemid pComb3H5BHis (this vector is described in the thesis dissertation of Dr. Ralf Lutterbüse) was digested accordingly and the large fragment was ligated with the above mentioned fragment. After transformation into *E. coli* XL1 blue, a single clone was cultivated in 100 mL SB medium (containing 50 µg/mL carbeniciline) and the plasmid was prepared according to standard protocols. The successful cloning was confirmed by sequencing the insert (Sequiserve, Munich).

This vector pComb3H5BHis/maternalVH of mAb A5B7 was restricted with the restriction enzymes SacI and SpeI. The large vector fragment was isolated. Plasmid-DNA containing the Vkappa- and the Vlambda library was restricted with the restriction enzymes SacI and SpeI. The small Vkappa—and the respective Vlambda fragment (each approximately 350 bp) were isolated according to standard protocols. 1200 ng of the vector fragment were ligated with a mix of each 200 ng of both the Vkappa and the Vlambda fragments. The ligation reaction was transformed into 300 µL of electrocompetent *E. coli* XL1 Blue by electroporation (2.5 kV, 0.2 cm gap cuvette, 25 mF, 200 Ohm) resulting in a total scFv library size of $1.2\times10^8$ independent clones.

After phenotype expression and slow adaptation to carbenicillin, the antibody library was transferred into SB-Carbenicillin (50 µg/mL) selection medium. The antibody library was then infected with an infectious dose of $1\times10^{12}$ particles of helper phage VCSM13 resulting in the production and secretion of filamentous M13 phage, wherein each phage particle contained single stranded pComb3H5BHis-DNA encoding a half-human scFv-fragment and displayed the corresponding scFv-protein as a translational fusion to phage coat protein III.

6. Phage Display Selection of a Human VL

The phage particles carrying the scFv-repertoire were harvested from the culture supernatant by PEG8000/NaCl precipitation and centrifugation. Then approximately $1\times10^{11}$ to 1×10$^{12}$ scFv phage particles were resuspended in 0.5 mL of TBS/1% BSA and incubated with biotinylated soluble CEA, that was immobilized in Streptavidin coated wells of an ELISA plate (Nunc) for 1 h. A 10 μg antigen/ml PBS solution (50 μl) was incubated for over night at 4° C. in the Streptavidin coated wells, washed once with water, followed by blocking for 1 hour at 37° C. with 200 μl of 3% BSA in TBS, that was removed after incubation.

scFv phage that did not specifically bind to the target antigen were eliminated by washing steps with TBS/0.05% Tween. This washing procedure was repeated up to 10 times in further rounds.

After washing, binding entities were eluted by using HCl-glycine, pH 2.2. Following neutralization with 2 M Tris, pH 12, the eluate was used for infection of a fresh uninfected *E. coli* XL1 Blue culture.

To elute remaining high binding entities 50 μL of a fresh *E. coli* XL1 blue culture (OD600≥0.5) were added to the wells and incubated for 15 minutes. Both cultures were then mixed and cells successfully transduced with a phagemid copy, encoding a human scFv-fragment, were again selected for carbenicillin resistance and subsequently infected with VCMS13 helper phage to start the second round of antibody display and in vitro selection.

Plasmid DNA corresponding to 4 rounds of panning was isolated from *E. coli* cultures. For the production of soluble scFv-protein, VH-VL-DNA fragments were excised from the plasmids (XhoI-SpeI), and cloned via the same restriction sites in the plasmid pComb3H5BFlag/His, in which the expression construct (e.g. scFv) includes a Flag-tag (TGDYKDDDDK) (SEQ ID NO. 59) between the scFv and the His6-tag and the additional phage proteins are deleted.

After ligation each pool (different rounds of panning) of plasmid DNA was transformed into 100 μL heat shock competent *E. coli* TG1 and plated onto carbenicillin LB-agar. Single colonies were picked and inoculated into 120 μL of LB carb (50 μg/mL) 1% glucose in 96-well plates (Greiner). The wells were sealed with a semipermeable membrane (Greiner) and the plates were incubated overnight at 37° C. in a shaking incubator (master plate). Then 10 μL of the master plate cultures were transferred into a second 96 well plate (working plate) containing 90 μL LB carb (50 μg/mL) 0.1% glucose per well. After incubation for 4 h in a 37° C. shaking incubator, scFv production was induced by adding 20 μL LB carb 6 mM IPTG to each well. After another incubation step overnight at 30° C. with shaking, cells were lysed in a 1 h incubation at room temperature with 40 μL lysis buffer (400 mM boric acid, 320 mM NaCl, 4 mM EDTA pH 8, 2.5 mg/mL lysozyme). Residual cells and cell debris were separated by centrifugation for 12 minutes at 1,900×g (Hettich).

The supernatants containing scFv molecules were then tested for binding in flow cytometric binding assays. CHO cells transfected with human CEA were used as CEA-positive cell line. Cell binding assays were carried out by initially incubating between 100,000 and 200,000 cells with periplasmic preparation containing human scFv or relevant controls. After incubation the cells were washed in PBS/1% FCS (fetal calf serum) and further incubated with 5-10 μg/ml of anti-FLAG M2 antibody (Sigma). After the cells had again been washed, they were incubated with polyclonal, PE-labeled anti-mouse antibodies (Dianova) and subsequently analyzed by flow cytometry. Approximately 600 clones were tested for binding signals on CEA-positive CHO cells. 27 positive clones were obtained. After sequencing of the respective scFv DNA, a total of 9 different sequences were obtained.

FIG. 2 depicts binding of the nine different half-human scFv (i.e. murine A5B7 VH-human VL) constructs to the CEA-transformed CHO cell line as measured by flow cytometric analysis. Said Figure contains multiple diagrams, one for each construct tested. In any given diagram, the black distribution shows fluorescence intensity for cells incubated only with PBS alone in the absence of any construct but with all appropriate detection agents as used for detection of scFvs. In this way, any fluorescence shift observed can be definitely attributed to scFv construct rather than detection agents or buffer. Shifts in fluorescence which are indicative of construct binding to the respective cell line are depicted by a gray line in each diagram. Generally, a shift of higher magnitude away from, i.e. further to the (black) control indicates stronger binding, whereas a shift of lower magnitude away from, i.e. closer to the (black) control indicates weaker binding.

It can be seen from FIG. 2 that the constructs A-121, A-183, A-240, A-313, A-290, A-315, A4-35, A4-52, MP2-A5 show clearly discernable shifts in fluorescence intensity as compared to the respective control, indicative of binding of the scFvs to membrane-bound CEA on the CHO target cells. In the following, the human VL region of scFv A-240 has been selected and used for the isolation of a human VH region. Said human A-240 VL region is encompassed e.g. in SEQ ID NO. 2.

EXAMPLE 4

Construction of the Antibody Libraries and Phage Display Selection of Humanized VH Regions Resistant to Soluble CEA Antigen The aim of the following experiments is the selection of a set of humanized VH regions resistant to soluble CEA antigen that pair with the human VL region of scFv A-240, selected as described in Example 3. Said human A-240 VL region is encompassed e.g. in SEQ ID NO. 2.

1. Isolation of RNA from Peripheric Blood Mononuclear Cells (PBMCs)

100 mL blood were taken from five healthy human donors. Peripheral blood mononuclear cells (PBMCs) were isolated by a ficoll-gradient according to standard methods. Total RNA was isolated from PBMCs using the RNeasy® Midi Kit (QIAGEN) following the manufacturer's instructions. cDNA was synthesized according to standard methods (Sambrook, Cold Spring Harbor Laboratory Press 1989, 2001).

2. PCR-Amplification of Variable Heavy Chain Regions (VH-Regions)

The VH library was constructed and named Lib 134-VH. This VH-library consists of the human repertoire of FR1-CDR1-FR2-CDR2-FR3 from the PCR amplified VH-regions of the above described PBMC pool, linked operatively to the VH CDR3 of the maternal antibody followed by a human FR4 germline sequence.

For the isolation of human template VH-regions, RT-PCR was carried out using a 5'-VH-specific primer set (5'-huVH1, 3,5-XhoI-2001 (5'-AGG TGC AGC TGC TCG AGT CTG G-3') (SEQ ID NO. 60), 5'-huVH4-XhoI-2001 (5'-CAG GTG CAG CTG CTC GAG TCG GG-3') (SEQ ID NO. 61), 5'-huVH4B-XhoI-2001 (5'-CAG GTG CAG CTA CTC GAG TGG GG-3') (SEQ ID NO. 62)) and a set of two 3'-VH-specific primers (3'-hu-VH-BstEII-2001 (5'-CTG AGG AGA CGG TGA CC-3') (SEQ ID NO. 63), 3'-hu-VH-J3-BstEII-2001 (5'-CTG AAG AGA CGG TGA CC-3') (SEQ ID NO. 64)). Per PCR reaction, one 5'-primer was combined with one 3'-primer; the number of different PCR reactions was determined by the number of possible combinations of 5'- and 3'-primers. The PBMC cDNA of five donors was used as a source of VH-genes. The following PCR-program was used for amplification: Denaturation at 94° C. for 15 seconds, primer annealing at 52° C. for 50 seconds and primer extension at 72° C. for 60 seconds was performed over 40 cycles, followed by final extension at 72° C. for 10 minutes. The amplification products with a size of approximately 350 bp were isolated according to standard methods.

For the isolation of Lib 134-VH-regions, RT-PCR was carried out in two steps. First, the human heavy chain VH-segments (FR1-CDR1-FR2-CDR2-FR3) were PCR-amplified from the isolated template VH fragments using the same 5'-VH-specific primer set as described above (5'-huVH1,3,5-XhoI-2001, 5'-huVH4-XhoI-2001, 5'-huVH4B-XhoI-2001; SEQ ID NOs. 60 to 62) and a 3'-specific primer set ( 3'-A134-VH1A (5'-GTA GTC AAA GTA GAA CCG TAG CCC CCT ATC TCT YGC ACA GTA ATA CAC GGC-3') (SEQ ID NO. 65), 3'-A134-VH1B (5'-GTA GTC AAA GTA GAA CCG TAG CCC CCT ATC TCT YGC ACA GTA ATA CAY RGC-3') (SEQ ID NO. 66), 3'-A134-VH3A (5'-GTA GTC AAA GTA GAA CCG TAG CCC CCT ATC TCT NGY ACA GTA ATA CAC RGC-3') (SEQ ID NO. 67), 3'-A134-VH3B (5'-GTA GTC AAA GTA GAA CCG TAG CCC CCT ATC TCT NGC ACA GTA ATA CAA RGC-3') (SEQ ID NO. 68), 3'-A134-VH4 (5'-GTA GTC AAA GTA GAA CCG TAG CCC CCT ATC TCT SGC ACA GTA ATA CAC RGC-3') (SEQ ID NO. 69)) for the human VH subfamilies 1, 3 and 4 matching in the very terminal region of FR3.

The following primer combinations were used:
a) 5'-huVH1,3,5-XhoI-2001×3'-A134-VH1A
b) 5'-huVH1,3,5-XhoI-2001×3'-A134-VH1B
c) 5'-huVH1,3,5-XhoI-2001×3'-A134-VH3A
d) 5'-huVH1,3,5-XhoI-2001×3'-A134-VH3B
e) 5'-huVH4-XhoI-2001×3'-A134-VH4
f) 5'-huVH4B-XhoI-2001×3'-A134-VH4

Per PCR reaction, one 5'-primer was combined with the 3'-primer; the number of different PCR reactions was determined by the number of possible combinations of 5'- and the 3'-primer. The following PCR-program was used for amplification: Denaturation at 94° C. for 15 seconds, primer annealing at 52° C. for 50 seconds and primer extension at 72° C. for 90 seconds was performed over 40 cycles, followed by final extension at 72° C. for 10 minutes. Through this PCR step and the respective 3'-primer sequence, the human VH segments are prolonged for a part of the maternal VH CDR3, which then in turn is the priming site for the second step PCR 3'-primer. These VH-(FR1-CDR1-FR2-CDR2-FR3) DNA-fragments were then used as templates in a second PCR reaction using again the respective 5'VH-specific primer and a universal 3' primer matching to the universal 3'-terminus of the amplified DNA-fragments (3'A134-JH6-BstEII, 5'-CGA GAC GGT GAC CGT GGT CCC TTG GCC CCA GTA GTC AAA GTA GAA CCG TAG CC-3') (SEQ ID NO. 70).

The following PCR-program was used for amplification: Denaturation at 94° C. for 15 seconds, primer annealing at 52° C. for 50 seconds and primer extension at 72° C. for 60 seconds were performed over 40 cycles, followed by final extension at 72° C. for 10 minutes. The DNA V-fragments were isolated according to standard protocols.

3. Library Construction—Cloning of the Human VH Pool

In a second round of the foregoing method, the human VL of scFv A-240 identified in the first, previous selection (see Example 3) was chosen, and subsequently combined with the library of human VH fragments with the aim of generating a human scFv. A phage display library was generally constructed based on standard procedures, as for example disclosed in "Phage Display: A Laboratory Manual"; Ed. Barbas, Burton, Scott & Silverman; Cold Spring Harbor Laboratory Press, 2001.

Heavy chain DNA-fragments from the different PCR amplifications were weighted for each ligation as follows:
a:b:c:d:e:f=3:1:3:1:1:1, wherein a-f have the following meanings:
a) derived from initial primer combination 5'-huVH1,3,5-XhoI-2001×3'-A134-VH1A
b) derived from initial primer combination 5'-huVH1,3,5-XhoI-2001×3'-A134-VH1B
c) derived from initial primer combination 5'-huVH1,3,5-XhoI-2001×3'-A134-VH3A
d) derived from initial primer combination 5'-huVH1,3,5-XhoI-2001×3'-A134-VH3B
e) derived from initial primer combination 5'-huVH4-XhoI-2001×3'-A134-VH4
f) derived from initial primer combination 5'-huVH4B-XhoI-2001×3'-A134-VH4

One ligation reaction was set up consisting of 400 ng of human Lib 134-VH fragment pool (XhoI-BstEII digested) and 1200 ng of the plasmid pComb3H5BHis/A-240 VL (the DNA encoding the VL region of scFv A-240 was cloned via the restriction sites SacI and SpeI into pComb3H5BHis according to standard procedures). The resulting antibody human VH pool was then transformed into 300 µL of electrocompetent *Escherichia coli* XL1 Blue by electroporation (2.5 kV, 0.2 cm gap cuvette, 25 mF, 200 Ohm, Biorad gene-pulser) resulting in a library size of $0.8 \times 10^8$ independent clones in total.

After electroporation the assay was incubated in SOC broth (Fluka) for phenotype expression. The cultures were then each incubated in 500 mL of SB selection medium containing 50 µg/mL carbenicillin and 2% v/v glucose overnight. The next day, cells of the cultures were harvested by centrifugation and plasmid preparation was carried out using a commercially available plasmid preparation kit (Qiagen) to preserve the DNA library.

1.5 µg of this plasmid pool were then electroporated into *E. coli* XL1 blue (2.5 kV, 0.2 cm gap cuvette, 25 mF, 200 Ohm, Biorad gene-pulser) resulting in a library size of $2.4 \times 10^9$ independent clones in total. After phenotype expression and slow adaption to carbenicillin the antibody library was transferred into SB-Carbenicillin (50 µg/mL) selection medium. The antibody library was then infected with an infectious dose of $1 \times 10^{12}$ particles of helper phage VCSM13 resulting in the production and secretion of filamentous M13 phage, wherein each phage particle contained single stranded pComb3H5BHis-DNA encoding a human scFv-fragment and displayed the corresponding scFv-protein as a translational fusion to phage coat protein III.

4. Phage Display Selection of a Human VH

The phage particles carrying the human scFv-repertoire were harvested from the culture supernatant by PEG8000/NaCl precipitation and centrifugation. Then approximately $1 \times 10^{11}$ to $1 \times 10^{12}$ scFv phage particles were resuspended in 0.5 mL of TBS/1% BSA and incubated with biotinylated soluble CEA, that was immobilized in Streptavidin coated wells of an ELISA plate (Nunc) for 1 h. A 10 µg antigen/ml PBS solution (50 µl) was incubated for over night at 4° C. in the Streptavidin coated wells, washed once with water, followed by blocking for 1 hour at 37° C. with 200 µl of 3% BSA in TBS, that was removed after incubation.

scFv phage that did not specifically bind to the target antigen were eliminated by washing steps with TBS/0.05% Tween. This washing procedure was repeated up to 10 times in further rounds.

After washing, binding entities were eluted by using HCl-glycine, pH 2.2. Following neutralization with 2 M Tris, pH 12, the eluate was used for infection of a fresh uninfected *E. coli* XL1 Blue culture.

To elute remaining high binding entities 50 μL of a fresh *E. coli* XL1 blue culture (OD600≥0.5) were added to the wells and incubated for 15 minutes. Both cultures were then mixed and cells successfully transduced with a phagemid copy, encoding a human scFv-fragment, were again selected for carbenicillin resistance and subsequently infected with VCMS13 helper phage to start the second round of antibody display and in vitro selection.

Plasmid DNA corresponding to 4 rounds of panning was isolated from *E. coli* cultures. For the production of soluble scFv-protein, VH-VL-DNA fragments were excised from the plasmids (XhoI-SpeI), and cloned via the same restriction sites in the plasmid pComb3H5BFlag/His, in which the expression construct (e.g. scFv) includes a Flag-tag (TGDYKDDDDK; SEQ ID NO. 59) between the scFv and the His6-tag and the additional phage proteins are deleted.

After ligation each pool (different rounds of panning) of plasmid DNA was transformed into 100 μL heat shock competent *E. coli* TG1 and plated onto carbenicillin LB-agar. Single colonies were picked and inoculated into 120 μL of LB carb (50 μg/mL) 1% glucose in 96-well plates (Greiner). The wells were sealed with a semipermeable membrane (Greiner) and the plates were incubated overnight at 37° C. in a shaking incubator (master plate). Then 10 μL of the master plate cultures were transferred into a second 96 well plate (working plate) containing 90 μL LB carb (50 μg/mL) 0.1% glucose per well. After incubation for 4 h in a 37° C. shaking incubator, scFv production was induced by adding 20 μL LB carb 6 mM IPTG to each well. After another incubation step overnight at 30° C. with shaking, cells were lysed in a 1 h incubation at room temperature with 40 μL lysis buffer (400 mM boric acid, 320 mM NaCl, 4 mM EDTA pH 8, 2.5 mg/mL lysozyme). Residual cells and cell debris were separated by centrifugation for 12 minutes at 1,900×g (Hettich).

The supernatants containing scFv molecules were then tested for binding in flow cytometric binding assays.

CHO cells transfected with human CEA were used as CEA-positive cell line. Cell binding assays were carried out by initially incubating between 100,000 and 200,000 cells with periplasmic preparation containing human scFv or relevant controls. After incubation the cells were washed in PBS/1% FCS (fetal calf serum) and further incubated with 5-10 μg/ml of anti-FLAG M2 antibody. After the cells had again been washed, they were incubated with polyclonal, PE-labeled anti-mouse antibodies (Dianova) and subsequently analyzed by flow cytometry. 46 clones were tested for binding signals on CEA-positive CHO cells. All of them showed positive signals. After sequencing of the respective scFv DNA a total of 9 different sequences were obtained, eight of which displayed a high degree of homology. The humanized constructs MP510_3-A5.3 (MP510-A5; SEQ ID NO. 2), MP510_3-B9.1 (MP511-B9; SEQ ID NO. 4), MP510_3-D8.1 (MP511-D8; SEQ ID NO. 6) have been selected for further characterization. The humanized VH region in these constructs contain the amino acid sequence "DRGLRFYFDY" (SEQ ID NO. 27) corresponding to Kabat positions 95-102 of the CDR-H3 of murine monoclonal antibody A5B7. The corresponding amino acid sequences of the scFvs are shown in Table 1.

Periplasmic extracts of said humanized constructs MP510-A5, MP511-B9, MP511-D8 as well as the half human construct A-240 Vlambda.3 (murine VH A5B7/human VL A240) were further analyzed in flow cytometric experiments with CEA-positive and -negative cell lines. It can be seen from FIG. 3, that the humanized constructs MP510-A5 (SEQ ID NO. 2), MP511-B9 (SEQ ID NO. 4), MP511-D8 (SEQ ID NO. 6) show clearly discernable shifts in fluorescence intensity as compared to the respective half-human control A-240 Vlambda.3 (murine VH A5B7/human VL A240). Thus, the human scFv constructs show stronger binding activity to membrane-bound human CEA than the half human construct A-240 Vlambda.3. In addition, all of the human constructs showed distinct binding to CEA-positive human KATO III cells (human gastric cancer cell line), whereas none of them showed binding to CEA-negative, untransfected CHO cells as well as to CEA-negative human NALM 6 cells (human B cell line) (data not shown).

EXAMPLE 5

Generation and Characterization of Humanized IgG1 Antibodies with Resistance to Soluble CEA Antigen Although bacteria are known to express functional Fab fragments, they are usually not capable of producing complete functional immunoglobulins. For the production of complete functional IgG1 antibodies, mammalian cells must be used and therefore the VL region of scFv A-240 and different VH regions of scFv molecules selected in Example 4 (especially VH regions of scFv A5, scFv D8 and scFv B9) were subcloned into mammalian expression vectors.

1. Cloning of the Human Light Chain Based on scFv A-240

The human VL of clone A-240 contained a Bsu36I restriction site in its nucleotide sequence. Therefore a variant was generated (A-240delBsu) using standard protocols that had a nucleotide exchange in the restriction motif that did not result in an amino acid exchange.

For cloning of the VL A-240 into a suitable mammalian expression vector, suitable terminal restriction sites had to be inserted. Therefore the DNA fragment encoding the VL region of scFv A240 was reamplified by PCR using the primers 5'-A240-Bsu36I (TTCTCTCCTTAGGTGTCCACTCC CAG GCC GTG CTG ACT CAG CCG GC) (SEQ ID NO. 93) and 3'-A240-overlap (GCCTTGGGCTGACCTAGGACG-GTC AACTTGGTCC) (SEQ ID NO. 94).

In a second PCR a human lambda constant region was amplified from a human cDNA pool using the 5'-primer 5'-Clam-overlap (GTTGACCGTCCTAGGTCAGC-CCAAGGCTGCCCCCTCG) (SEQ ID NO. 95) and the 3'-primer 3'-Clam-NotI (GACGTA GCGGCCGC GTCGAC CTATGAACATTCTGTAGGGGC) (SEQ ID NO. 96) according to standard methods. The approximately 330 bp DNA products of both PCRs had an identical 3' (A-240) or 5' (C lambda) overlap in sequence.

The two fragments were used in a fusion PCR (according to standard protocols) in combination with the 5'-primer 5'-A240-Bsu36I and the 3'-primer 3'-Clam-NotI to generate a full length light chain product coding for the human VL A-240 fused to a human lambda constant region (corresponding amino acid sequence shown in SEQ ID NO: 80). This DNA-fragment contained a Bsu36I-site at the 5'-end and a SalI restriction site at the 3'-terminus followed by a NotI restriction site.

This fragment was then subcloned into the pBS-derived plasmid (as described above) by Bsu36I and NotI thus adding a human leader sequence. This construct was verified by sequencing. Utilizing EcoRI and SalI, A-240 VL-Clambda DNA was excised from said construct and subcloned into the eukaryotic expression vector pEF-ADA derived from the expression vector pEF-DHFR (Mack et al. (1995) Proc. Natl.

Acad. Sci. USA. 92, 7021-5) by replacing the cDNA encoding murine dihydrofolate reductase (DHFR) with that encoding murine adenosine deaminase (ADA). pEF-ADA is described in Raum, loc. cit. The amino acid sequence of A-240 VL-Clambda (corresponding to the A240 light chain) is shown in SEQ ID NO. 80.

2. Cloning of Humanized Heavy Chain Variable Domains

From different humanized VH regions selected in example 4 (especially VH regions of scFv A5, scFv D8 and scFv B9), the variable region was reamplified by PCR, generating Bsu36I restriction sites at both ends. For all constructs the combination of two primers was used: 5'-primer 5'-CVH-Bsu36I (5'-TTCTCTCCTTAGGTGTCCACTCC GAG GTG CAG CTG GTC GAG TC-3') (SEQ ID NO. 97) and 3'-primer 3'-CVH-Bsu36I (5'-GACTCACCTGAGGA GAC GGT GAC CGT GGT CCC TTG G-3') (SEQ ID NO. 98). The resulting DNA-fragments were then subcloned using these restriction sites into the eukaryotic expression vector pEF-DHFR already containing a eukaryotic leader sequence and a DNA-fragment encoding the human IgG1 heavy chain constant region. The heavy chain variable regions were thus inserted between the leader and the heavy chain constant region. The correct sequences of the variable regions were confirmed by sequencing. The amino acid sequence of the A5 heavy chain is shown in SEQ ID NO. 77, the amino acid sequence of the B9 heavy chain is shown in SEQ ID NO. 78 and the amino acid sequence of the D8 heavy chain is shown in SEQ ID NO. 79.

3. Expression of Humanized Full IgG Proteins

Plasmid encoding for one light chain and plasmid encoding for one heavy chain (VH/human IgG1 constant region) were cotransfected into HEK cells according to standard protocols for transient protein expression and the cells were cultured to allow the expression and production of the immunoglobulins into the culture medium. In this manner, IgG1 A5 derived from scFv A5, IgG1 D8 derived from scFv D8 and IgG1 B9 derived from scFv B9 were produced. After the respective production period, the supernatants were harvested and the humanized immunoglobulins were isolated via Protein A chromatography according to standard protocols for the purification of immunoglobulins. Culture supernatants, as well as purified immunoglobulins were then used for further characterization experiments.

The amino acid sequence of the A5 heavy chain is shown in SEQ ID NO. 77, the amino acid sequence of the B9 heavy chain is shown in SEQ ID NO. 78 and the amino acid sequence of the D8 heavy chain is shown in SEQ ID NO. 79. The amino acid sequence of the A240 light chain is shown in SEQ ID NO. 80. IgG1 A5, derived from scFv A5, comprises the A5 heavy chain shown in SEQ ID NO. 77 and the amino acid sequence of the A240 light chain shown in SEQ ID NO. 80. IgG1 B9, derived from scFv B9, comprises the amino acid sequence of the B9 heavy chain shown in SEQ ID NO. 78 and the amino acid sequence of the A240 light chain shown in SEQ ID NO. 80. IgG1 D8, derived from scFv D8, comprises the amino acid sequence of the D8 heavy chain shown in SEQ ID NO. 79 and the amino acid sequence of the A240 light chain shown in SEQ ID NO. 80. The (humanized) VH region in these IgG1 antibody constructs contains the amino acid sequence "DRGLRFYFDY" (SEQ ID NO. 27) corresponding to Kabat positions 95-102 of the CDR-H3 of murine monoclonal antibody A5B7. The corresponding amino acid sequences of the above mentioned heavy and light chains are shown in Table 1.

4. Characterization of Humanized IgG1 Antibodies with Resistance to Soluble CEA Antigen 4.1 Binding to Immobilized Soluble CEA (sCEA) Antigen Culture supernatants of heavy+light chain double transfectants as well as the corresponding preparations of purified antibody were tested for binding on immobilized sCEA antigen by ELISA according to standard procedures. An irrelevant human IgG1 antibody was included as a negative control.

In brief, antibody binding was tested on immobilized CEA antigen and for demonstration of CEA specificity also in the absence of coated CEA antigen using culture supernatant and purified antibody solutions of 10 ug/ml and 1 ug/ml, respectively. These antibody solutions were added to the +/−antigen coated (4° C. over night) and BSA blocked wells (1 hr, 37° C.). Detection was performed by peroxidase-labeled polyclonal human IgG antibody (Jackson ImmunoResearch). The signals were measured after appropriate incubation with ABTS solution.

As shown in FIG. 4, the humanized antibodies IgG1 A5, IgG1 D8 and IgG1 B9 as well as the hulgG1-CEA I and -CEA II constructs of Example 2 showed distinct binding to the immobilized soluble CEA (sCEA) antigen as compared to the negative control—and no binding in an equivalent setting with the difference that no sCEA antigen was coated.

4.2 Binding to Native CEA Antigen on Cells

Purified antibody preparations of humanized IgG1 A5, IgG1 D8 and IgG1 B9 constructs as well as the hulgG1-CEA I and -CEA II constructs of Example 2 were tested by FACS analysis on CEA expressing Kato III cells, CEA-transfected CHO-cells and CEA-untransfected CHO-cells.

$2 \times 10^5$ cells were incubated with purified antibody preparations (typically 10-20 μg/ml). Detection was performed by a biotinylated polyclonal anti-human IgG antibody (DAKO) followed by PE-labeled Streptavidine (Jackson ImmunoResearch) (typically 10-20 μg/ml). Incubation was carried out for 20-40 min. on ice.

The humanized IgG1 A5, IgG1 D8 and IgG1 B9 constructs as well as the hulgG-CEA I and -CEA II constructs of Example 2 showed distinct binding to the CEA positive cells (FIGS. 5A, B and C). None of the antibodies showed binding to untransfected CHO cells. IgG-controls were negative on Kato-cells, CHO/CEA-cells and untransfected CHO cells.

4.3 Antibody Dependent Cell-Mediated Cytotoxicity (ADCC; $^{51}$Cr Release Assay)

For the $^{51}$Cr release assay, human peripheral blood mononuclear cells (PBMCs) as effector cells were isolated from a healthy donors. The PBMCs were separated by Ficoll density gradient centrifugation with a subsequent 100×g centrifugation step. Unstimulated PBMCs ($5 \times 10^5$ cells) were added in a volume of 100 μl of RPMI 1640 medium with 10% FCS to each well of a flat bottomed microtiter plate and incubated overnight at 37° C. As target cells, the CEA-positive gastric cancer cell line KATO III has been used. Target cells (50.000 cells) were labelled for 2 h with $^{51}$Cr. Labeled target cells (100 μl) and antibodies in different concentrations (10 μg/ml-10 μg/ml) were added to the PBMCs and incubated for 18 h at 37° C. Corresponding non-binding isotypes were used as negative controls. Specific lysis was calculated as ((cpm, experimental release)−(cpm, spontaneous release))/((cpm, maximal release)−(cpm, spontaneous release)).

In the absence of sCEA, the humanized anti-CEA antibodies IgG1 A5, IgG1 D8 and IgG1 B9 proved to mediate cytotoxicity to the CEA positive gastric cancer cell line KATO III as compared to the negative control. The same result has been observed for the IgG versions of the antibodies CEA I and CEA II (hulgG1-CEA I and -CEA II constructs) as set forth in Example 2. In parallel, the antibody samples were preincubated with soluble CEA (sCEA) antigen for 20 min under agitation and then mixed with the labeled target cells and the human PBMCs. Otherwise, the assay has been performed as described above. Soluble CEA (sCEA) antigen has been used in different concentrations, i.e. 1 µg/ml and 10 µg/ml. The assay was measured and the respective cytotoxic values plotted.

Two representative results are shown in FIGS. 6A and B for antibody CEA II and antibody IgG1 A5, respectively. It was demonstrated in this assay that the cytolytic potential of antibody CEA II was dramatically reduced in the presence of soluble CEA antigen in a dose-dependent manner. The respective curve clearly shifts to the right in the presence of 1 ug/ml sCEA as compared to the curve without soluble CEA. In the presence of 10 ug/ml sCEA, no cytolytic curve was observed indicating the complete reduction of cytolytic activity of antibody CEA II below detection level. The respective EC 50 values (half maximal cytolytic antibody concentrations) were estimated as being higher in concentration than the last cytotoxic value at base level. This leads to an underestimation of the EC50 levels for antibody CEA II and a probably even much higher "inhibitory factor" as specified below.

In contrast, no significant inhibitory effect of soluble CEA antigen in the cytolytic assay was demonstrated for the antibodies IgG1 A5, IgG1 B9 and IgG1 D8. All antibodies showed comparable EC50 values in the absence of soluble CEA, indicating a comparable cytolytic activity in the absence of soluble CEA.

EC50 values were determined by the analysis software. The EC 50 values are depicted in Table 2.

TABLE 2

ADCC EC50 values of the respective antibodies in ng/ml in the presence of different concentrations of soluble CEA (sCEA)

| sCEA ug/ml | CEA II | IgG1 A5 | IgG1 B9 | IgG1 D8 |
|---|---|---|---|---|
| 0 | 2.7 | 2.7 | 4.8 | 4.4 |
| 1 | >100 | 4 | 45.3 | 14.7 |
| 10 | >200 | 2.8 | 53.4 | 6.3 |

Cytolytic inhibition in the presence of soluble CEA antigen was converted into an "inhibitory factor". This factor is defined as the EC50 in the presence of 10 and 1 ug/ml soluble CEA in the ADCC assay divided by the EC50 in absence of soluble CEA. The inhibitory factors are depicted in Table 3.

TABLE 3

Inhibitory factors of the respective antibodies in the presence of different concentrations of soluble CEA (sCEA)

| | CEA II | IgG1 A5 | IgG1 B9 | IgG1 D8 |
|---|---|---|---|---|
| 10 ug/ml sCEA | >74.1 | 1.0 | 11.1 | 1.4 |
| 1 ug/ml sCEA | >37.0 | 1.5 | 9.4 | 3.3 |

A graphic presentation of the inhibitory factors is illustrated in FIG. 7. This Figure shows clearly, that CEA II has a dramatically decreased cytolytic activity in the presence of soluble CEA antigen at 1 ug/ml, showing a more than 37 times reduced cytolytic activity in the presence of soluble CEA antigen, whereas IgG1 A5- and IgG1 D8-mediated cytolytic activity towards tumor cells is completely resistant to soluble CEA. IgG1 B9-mediated cytolytic activity towards tumor cells is only slightly affected by sCEA. Said antibody constructs show inhibitory factors below 10.

This effect is even more pronounced at the 10 ug/ml concentration of soluble CEA in the ADCC assay. The cytolytic curve of antibody CEA II is reduced to baseline (no cytolytic activity even at the highest concentrations could be detected). Therefore the inhibitory factor for antibody CEA II was estimated to be 74 at it's best, probably being far underestimated.

In summary, in the presence of soluble CEA, hulgG-CEA II (derived from mAb T84.66) showed drastically reduced cytotoxic activity against CEA positive target cells; see Examples 2 and 5. In contrast, the humanized CEA antibodies IgG1 A5, IgG1 D8 and IgG1 B9 showed no significant decrease of cytolytic activity as compared to the activity in the absence of soluble CEA. IgG1 A5-, IgG1 B9- and IgG1 D8-mediated cytolytic activity towards tumor cells is resistant to soluble CEA. Surprisingly, the amino acid sequence "DRGLRFYFDY" (SEQ ID NO. 27) corresponding to Kabat positions 95-102 of the CDR-H3 of murine monoclonal antibody A5B7 in the VH regions of the otherwise completely human IgG1 antibodies IgG1 A5, IgG1 D8 and IgG1 B9 is sufficient to mediate resistance to soluble CEA antigen.

TABLE 1

| SEQ ID NO. | | SOURCE | | SEQUENCE |
|---|---|---|---|---|
| 1 | A5 VH-A240VL | human | Nt | GAGGTGCAGCTGCTCGAGTCTGGGGGAGGCGTGGTCCAGCCTGGGAGGTCCCTGAGACTCTCC<br>TGTGCAGCCTCTGGATTCACCCTCAGTACCTATGCCATGCACTGGGTCCGCCAGGCTCCAGGCAA<br>GGGGCTGGAGTGGGTGGCACTTATATCAAATGATGGAAGCAATAAATACTATGCAGACTCCGTGA<br>AGGGCCGATTCACCATCTCCAGAGACAATTCCAAGAACACGCTGTATCTGCAAATGAACAGCCTG<br>AGAGCTGAGGACACGGCCGTGTATTACTGTGCGAGAGATAGGGGGCTACGGTTCTACTTTGACTA<br>CTGGGGCCAAGGGACCACGGTCACCGTCTCCTCAGGTGGTGGTGGTTCTGGCGGCGGCGGCTC<br>CGGTGGTGGTGGTTCTGAGCTCGTGCTGACTCAGCCGGCTTCCCTCTCTGCATCTCCTGGAGCAT<br>CAGCCAGTCTCACCTGCACCTTGCGCAGGGGCATCAATGTTGGTGCCTACAGTATATACTGGTAC<br>CAGCAGAAGCCAGGGAGTCCTCCCCAGTATCTCCTGAGGTACAAATCAGACTCAGATAAGCAGCA<br>GGGCTCTGGAGTCTCCAGCCGCTTCTCTGCATCCAAAGATGCTTCGGCCAATGCAGGGATTTTAC<br>TCATCTCTGGGCTCCAGTCTGAGGATGAGGCTGACTATTACTGTATGATTTGGCACAGCGGCGCT<br>TCTGCGGTGTTCGGCGGAGGGACCAAGTTGACCGTCCTATAG |
| 2 | A5 VH-A240VL | human | AA | EVQLLESGGGVVQPGRSLRLSCAASGFTLSTYAMHWVRQAPGKGLEWVALISNDGSNKYYADSVKG<br>RFTISRDNSKNTLYLQMNSLRAEDTAVYYCARDRGLRFYFDYWGQGTTVTVSSGGGGSGGGGSGGG<br>GSELVLTQPASLSASPGASASLTCTLRRGINVGAYSIYWYQQKPGSPPQYLLRYKSDSDKQQGSGVS<br>SRFSASKDASANAGILLISGLQSEDEADYYCMIWHSGASAVFGGGTKLTVL* |

TABLE 1-continued

| SEQ ID NO. | | SOURCE | | SEQUENCE |
|---|---|---|---|---|
| 3 | B9 VH-A240VL | human | Nt | GAGGTGCAGCTGCTCGAGTCTGGGGGAGGCTTGGTCCAGCCTGGAGGTCCCTGAGACTCTCCT<br>GTGCAGCGTCTGGATTCACCGTCAGTAGCTACTGGATGCACTGGGTCCGCCAAGCTCCAGGGAA<br>GGGGCTGGAATGGGTAGGTTTCATTAGAAACAAAGCTAATGGTGGGACAACAGAATACGCCGCGT<br>CTGTGAAAGGCAGATTCACCATCTCAAGAGATGATTCCAAGAACACGCTGTATCTTCAAATGAACA<br>GCCTGAGAGCCGAGGACACGGCCGTGTATTACTGTGCAAGAGATAGGGGCTACGGTTCTACTT<br>TGACTACTGGGGCCAAGGGACCACGGTCACCGTCTCCTCAGGTGGTGGTGGTTCTGGCGGCGG<br>CGGCTCCGGTGGTGGTGGTTCTGAGCTCGTGCTGACTCAGCCGGCTTCCCTCTCTGCATCTCCTG<br>GAGCATCAGCCAGTCTCACCTGCACCTTGCGCAGGGGCATCAATGTTGGTGCCTACAGTATATAC<br>TGGTACCAGCAGAAGCCAGGGAGTCCTCCCCAGTATCTCCTGAGGTACAAATCAGACTCAGATAA<br>GCAGCAGGGCTCTGGAGTCTCCAGCCGCTTCTCTGCATCCAAAGATGCTTCGGCCAATGCAGGG<br>ATTTTACTCATCTCTGGGCTCCAGTCTGAGGATGAGGCTGACTATTACTGTATGATTTGGCACAGC<br>GGCGCTTCTGCGGTGTTCGGCGGAGGGACCAAGTTGACCGTCCTATAG |
| 4 | B9 VH-A240VL | human | AA | EVQLLESGGGLVQPGRSLRLSCAASGFTVSSYWMHWVRQAPGKGLEWVGFIRNKANGGTTEYAASV<br>KGRFTISRDDSKNTLYLQMNSLRAEDTAVYYCARDRGLRFYFDYWGQGTTVTVSSGGGGSGGGGSG<br>GGGSELVLTQPASLSASPGASASLTCTLRRGINVGAYSIYWYQQKPGSPPQYLLRYKSDSDKQQSG<br>VSSRFSASKDASANAGILLISGLQSEDEADYYCMIWHSGASAVFGGGTKLTVL* |
| 5 | D8 VH-A240VL | human | Nt | GAGGTGCAGCTGCTCGAGTCTGGGGGAGGCGTGGTCCAGCCTGGGAGGTCCCTGAGACTCTCC<br>TGTGCAGCCTCTGGATTCACCCTCAGTACCTATGCCATGCACTGGGTCCGCCAGGCTCCAGGCAA<br>GGGGCTGGAGTGGGTGGCACTTATATCAAATGATGGAAGCAATAAATACTATGCAGACTCCGTGA<br>AGGGCCGATTCACCATCTCCAGAGACAATTCCAAGAACACGCTGTATCTGCAAATGAACAGCCTG<br>AGAGCTGAGGACACGGCTGTGTATTACTGTACTAGAGATAGGGGCTACGGTTCTACTTTGACTA<br>CTGGGGCCAAGGGACCACGGTCACCGTCTCCTCAGGTGGTGGTGGTTCTGGCGGCGGCGGCTC<br>CGGTGGTGGTGGTTCTGAGCTCGTGCTGACTCAGCCGGCTTCCCTCTCTGCATCTCCTGAGCAT<br>CAGCCAGTCTCACCTGCACCTTGCGCAGGGGCATCAATGTTGGTGCCTACAGTATATACTGGTAC<br>CAGCAGAAGCCAGGGAGTCCTCCCCAGTATCTCCTGAGGTACAAATCAGACTCAGATAAGCAGCA<br>GGGCTCTGGAGTCTCCAGCCGCTTCTCTGCATCCAAAGATGCTTCGGCCAATGCAGGGATTTTAC<br>TCATCTCTGGGCTCCAGTCTGAGGATGAGGCTGACTATTACTGTATGATTTGGCACAGCGGCGCT<br>TCTGCGGTGTTCGGCGGAGGGACCAAGTTGACCGTCCTATAG |
| 6 | D8 VH-A240VL | human | AA | EVQLLESGGGVVQPGRSLRLSCAASGFTLSTYAMHWVRQAPGKGLEWVALISNDGSNKYYADSVKG<br>RFTISRDNSKNTLYLQMNSLRAEDTAVYYCTRDRGLRFYFDYWGQGTTVTVSSGGGGSGGGGSGGG<br>GSELVLTQPASLSASPGASASLTCTLRRGINVGAYSIYWYQQKPGSPPQYLLRYKSDSDKQQSGVS<br>SRFSASKDASANAGILLISGLQSEDEADYYCMIWHSGASAVFGGGTKLTVL* |
| 7 | A5B7 VH | murine | Nt | GAGGTGCAGCTGGTCGAGTCAGGAGGAGGCTTGGTACAGCCTGGGGGTTCTCTGAGACTCTCCT<br>GTGCAACTTCTGGGTTCACCTTCACTGATTACTACATGAACTGGGTCCGCCAGCCTCCAGGAAAG<br>GCACTTGAGTGGTTGGGTTTTATTGGAAACAAAGCTAATGGTTACAACAAGAGTACAGTGCATCT<br>GTGAAGGGTCGGTTCACCATCTCCAGAGATAAATCCCAAAGCATCCTCTATCTTCAAATGAACACC<br>CTGAGAGCTGAGGACAGTGCCACTTATTACTGTACCAGAGATAGGGGCTACGGTTCTACTTTGA<br>CTACTGGGGCCAAGGGACCACGGTCACCGTCTCCTCA |
| 8 | A5B7 VH | murine | AA | EVQLVESGGGLVQPGGSLRLSCATSGFTFTDYYMNWVRQPPGKALEWLGFIGNKANGYTTEYSASV<br>KGRFTISRDKSQSILYLQMNTLRAEDSATYYCTRDRGLRFYFDYWGQGTTVTVSS |
| 9 | A5B7 VL | murine | Nt | GACATTGAGCTCACCCAGTCTCCAGCAATCCTGTCTGCATCTCCAGGGGAGAAGGTCACAATGAC<br>TTGCAGGGCCAGCTCAAGTGTAACTTACATTCACTGGTACCAGCAGAAGCCAGGATCCTCCCCCA<br>AATCCTGGATTTATGCCACATCCAACCTGGCTTCTGGAGTCCCTGCTCGCTTCAGTGGCAGTGGG<br>TCTGGGACCTCTTACTCTCTCACAATCAGCAGAGTGGAGGCTGAAGATGCTGCCACTTATTACTGC<br>CAACATTGGAGTAGTAAACCACCGACGTTCGGTGGAGGGACCAAGCTCGAGATCAAA |
| 10 | A5B7 VL | murine | AA | DIELTQSPAILSASPGEKVTMTCRASSSVTYIHWYQQKPGSSPKSWIYATSNLASGVPARFSGSGSGT<br>SYSLTISRVEAEDAATYYCQHWSSKPPTFGGGTKLEIK |
| 11 | T84.66 VH | murine | Nt | GAGGTTCAGCTGCAGCAGTCTGGGCAGAGCTTGTGGAGCCAGGGGCCTCAGTCAAGTTGTCCT<br>GCACAGCTTCTGGCTTCAACATTAAAGACACCTATATGCACTGGGTGAAGCAGAGGCCTGAACAG<br>GGCCTGGAATGGATTGGAAGGATTGATCCTGCGAATGGTAATAGTAAATATGTCCCGAAGTTCCA<br>GGGCAAGGCCACTATAACAGCAGACACATCCTCCAACACAGCCTACCTGCAGCTCACCAGCCTGA<br>CATCTGAGGACACTGCCGTCTATTATTGTGCTCCGTTTGGTTACTACGTGTCTGACTATGCTATGG<br>CCTACTGGGGTCAAGGAACCTCAGTCACCGTCTCCTCC |
| 12 | T84.66 VH | murine | AA | EVQLQQSGAELVEPGASVKLSCTASGFNIKDTYMHWVKQRPEQGLEWIGRIDPANGNSKYVPKFQGK<br>ATITADTSSNTAYLQLTSLTSEDTAVYYCAPFGYYVSDYAMAYWGQGTSVTVSS |
| 13 | T84.66 VL | murine | Nt | GACATTGTGCTGACCCAATCTCCAGCTTCTTTGGCTGTGTCTCTTGGGCAGAGGGCCACCATGTC<br>CTGCAGAGCCGGTGAAAGTGTTGATATTTTTGGCGTTGGGTTTTTGCACTGGTACCAGCAGAAAC<br>CAGGACAGCCACCCAAACTCCTCATCTATCGTGCATCCAACCTAGAATCTGGGATCCCTGTCAGG<br>TTCAGTGGCACTGGGTCTAGGACAGACTTCACCCTCATCATTGATCCTGTGGAGGCTGATGATGT<br>TGCCACCTATTACTGTCAGCAAACTAATGAGGATCCGTACACGTTCGGAGGGGGGACCAAGCTCG<br>AGATAAAA |
| 14 | T84.66 VL | murine | AA | DIVLTQSPASLAVSLGQRATMSCRAGESVDIFGVGFLHWYQQKPGQPPKLLIYRASNLESGIPVRF<br>SGTGSRTDFTLIIDPVEADDVATYYCQQTNEDPYTFGGGTKLEIK |

TABLE 1-continued

| SEQ ID NO. | | SOURCE | | SEQUENCE |
|---|---|---|---|---|
| 15 | MFE-23 VH | murine | Nt | CAGGTTAAGCTGCAGCAGTCTGGGGCAGAGCTTGTGAGATCAGGGACATCAGTCAAGTTGTCCTG CACAGCTTCTGGCTTCAACATTAAAGACTCCTATATGCACTGGCTGAGGCAGGGGCCTGAACAGG GCCTGGAGTGGATTGGATGGATTGATCCTGAGAATGGTGATACTGAATATGCCCCGAAGTTCCAG GGCAAGGCCACTTTCACTACTGACACATCCTCCAACACAGCCTACCTGCAGCTCAGCAGCCTGAC ATCTGAGGACACTGCCGTCTATTACTGTAACGAGGGCACACCTACAGGGCCTTACTACTTTGACTA CTGGGGCCAAGGCACCACTGTCACAGTCTCCTCC |
| 16 | MFE-23 VH | murine | AA | QVKLQQSGAELVRSGTSVKLSCTASGFNIKDSYMHWLRQGPEQGLEWIGWIDPENGDTEYAPKFQG KATFTTDTSSNTAYLQLSSLTSEDTAVYYCNEGTPTGPYYFDYWGQGTTVTVSS |
| 17 | MFE-23 VL | murine | Nt | GAGAACGTTCTCACCCAGTCTCCAGCAATCATGTCTGCATCTCCAGGGGAGAAGGTCACCATCAC CTGCAGTGCCAGCTCAAGCGTCAGCTACATGCACTGGTTCCAGCAGAAGCCAGGCACCTCCCCC AAACTCTGGATTTATTCTACATCCAACCTGGCTTCTGGAGTCCCTGCTCGCTTCTCTGGCAGTGGG TCTGGGACCTCTTACTCTCTCACAATCAGCAGAATGGAGGCTGAAGATGCTGCCACTTATTACTGC CAGCAGAGAAGTAGTTACCCACTCACGTTCGGTGCTGGGACCAAGCTCGAGCTGAAA |
| 18 | MFE-23 VL | murine | AA | ENVLTQSPAIMSASPGEKVTITCSASSSVSYMHWFQQKPGTSPKLWIYSTSNLASGVPARFSGSGSGT SYSLTISRMEAEDAATYYCQQRSSYPLTFGAGTKLELK |
| 19 | A5 VH | human | Nt | GAGGTGCAGCTGGTCGAGTCTGGGGGAGGCGTGGTCCAGCCTGGGAGGTCCCTGAGACTCTCC TGTGCAGCCTCTGGATTCACCCTCAGTACCTATGCCATGCACTGGGTCCGCCAGGCTCCAGGCAA GGGGCTGGAGTGGGTGGCACTTATATCAAATGATGGAAGCAATAAATACTATGCAGACTCCGTGA AGGGCCGATTCACCATCTCCAGAGACAATTCCAAGAACACGCTGTATCTGCAAATGAACAGCCTG AGAGCTGAGGACACGGCCGTGTATTACTGTGCGAGAGATAGGGGCTACGGTTCTACTTTGACTA CTGGGGCCAAGGGACCACGGTCACCGTCTCCTCA |
| 20 | A5 VH | human | AA | EVQLVESGGGVVQPGRSLRLSCAASGFTLSTYAMHWVRQAPGKGLEWVALISNDGSNKYYADSVKG RFTISRDNSKNTLYLQMNSLRAEDTAVYYCARDRGLRFYFDYWGQGTTVTVSS |
| 21 | B9 VH | human | Nt | GAGGTGCAGCTGGTCGAGTCTGGGGGAGGCTTGGTCCAGCCTGGGAGGTCCCTGAGACTCTCCT GTGCAGCGTCTGGATTCACCGTCAGTAGCTACTGGATGCACTGGGTCCGCCAAGCTCCAGGGAA GGGGCTGGAATGGGTAGGTTTCATTAGAAACAAAGCTAATGGTGGGACAACAGAATACGCCGCGT CTGTGAAAGGCAGATTCACCATCTCAAGAGATGATTCCAAGAACACGCTGTATCTTCAAATGAACA GCCTGAGAGCTGAGGACACGGCCGTGTATTACTGTGCAAGAGATAGGGGCTACGGTTCTACTT TGACTACTGGGGCCAAGGGACCACGGTCACCGTCTCCTCA |
| 22 | B9 VH | human | AA | EVQLVESGGGLVQPGRSLRLSCAASGFTVSSYWMHWVRQAPGKGLEWVGFIRNKANGGTTEYAASV KGRFTISRDDSKNTLYLQMNSLRAEDTAVYYCARDRGLRFYFDYWGQGTTVTVSS |
| 23 | D8 VH | human | Nt | GAGGTGCAGCTGGTCGAGTCTGGGGGAGGCGTGGTCCAGCCTGGGAGGTCCCTGAGACTCTCC TGTGCAGCCTCTGGATTCACCCTCAGTACCTATGCCATGCACTGGGTCCGCCAGGCTCCAGGCAA GGGGCTGGAGTGGGTGGCACTTATATCAAATGATGGAAGCAATAAATACTATGCAGACTCCGTGA AGGGCCGATTCACCATCTCCAGAGACAATTCCAAGAACACGCTGTATCTGCAAATGAACAGCCTG AGAGCTGAGGACACGGCTGTGTATTACTGTACTAGAGATAGGGGCTACGGTTCTACTTTGACTA CTGGGGCCAAGGGACCACGGTCACCGTCTCCTCA |
| 24 | D8 VH | human | AA | EVQLVESGGGVVQPGRSLRLSCAASGFTLSTYAMHWVRQAPGKGLEWVALISNDGSNKYYADSVKG RFTISRDNSKNTLYLQMNSLRAEDTAVYYCTRDRGLRFYFDYWGQGTTVTVSS |
| 25 | A240VL | human | Nt | CAGGCCGTGCTGACTCAGCCGGCTTCCCTCTCTGCATCTCCTGGAGCATCAGCCAGTCTCACCTG CACCTTGCGCAGGGGCATCAATGTTGGTGCCTACAGTATATACTGGTACCAGCAGAAGCCAGGGA GTCCTCCCCAGTATCTCCTGAGGTACAAATCAGACTCAGATAAGCAGCAGGGCTCTGGAGTCTCC AGCCGCTTCTCTGCATCCAAAGATGCTTCGGCCAATGCAGGGATTTTACTCATCTCTGGGCTCCA GTCTGAGGATGAGGCTGACTATTACTGTATGATTTGGCACAGCGGCGCTTCTGCGGTGTTCGGCG GAGGGACCAAGTTGACCGTCCTA |
| 26 | A240VL | human | AA | QAVLTQPASLSASPGASASLTCTLRRGINVGAYSIYWYQQKPGSPPQYLLRYKSDSDKQQGSGVSSR FSASKDASANAGILLISGLQSEDEADYYCMIWHSGASAVFGGGTKLTVL |
| 27 | CDR-H3 A5B7 Kabat positions 95, 96, 97, 98, 99, 100, 100a, 100b, 101, 102 | murine | AA | DRGLRFYFDY |
| 28 | CDR-H2 B9 | human | AA | FIRNKANGGTTEYAASVKG |
| 29 | CDR-H1 B9 | human | AA | SYWMH |
| 30 | CDR-H2 A5/D8 | human | AA | LISNDGSNKYYADSVKG |
| 31 | CDR-H1 A5/D8 | human | AA | TYAMH |
| 32 | CDR-L3 A240 | human | AA | MIWHSGASAV |

TABLE 1-continued

| SEQ ID NO. | | SOURCE | | SEQUENCE |
|---|---|---|---|---|
| 33 | CDR-L2 A240 | human | AA | YKSDSDKQQGS |
| 34 | CDR-L1 A240 | human | AA | TLRRGINVGAYSIY |
| 35 | 5' CEACAM5 EcoRI | artificial | Nt | GAATTCGCCACCATGGAGTCTCCCTCGGCCCC |
| 36 | 3' CEACAM5 Sal I | artificial | Nt | GTCGACCTATATCAGAGCAACCCC |
| 37 | CEACAM5 (NM_004363) | human | AA | MESPSAPPHRWCIPWQRLLLTASLLTFWNPPTTAKLTIESTPFN VAEGKEVLLLVHNLPQHLFGYSWYKGERVDGNRQIIGYVIGTQQATPGPAYSGREIIY PNASLLIQNIIQNDTGFYTLHVIKSDLVNEEATGQFRVYPELPKPSISSNNSKPVEDK DAVAFTCEPETQDATYLWWVNNQSLPVSPRLQLSNGNRTLTLFNVTRNDTASYKCETQ NPVSARRSDSVILNVLYGPDAPTISPLNTSYRSGENLNLSCHAASNPPAQYSWFVNGT FQQSTQELFIPNITVNNSGSYTCQAHNSDTGLNRTTVTTITVYAEPPKPFITSNNSNP VEDEDAVALTCEPEIQNTTYLWWVNNQSLPVSPRLQLSNDNRTLTLLSVTRNDVGPYE CGIQNELSVDHSDPVILNVLYGPDDPTISPSYTYYRPGVNLSLSCHAASNPPAQYSWL IDGNIQQHTQELFISNITEKNSGLYTCQANNSASGHSRTTVKTITVSAELPKPSISSN NSKPVEDKDAVAFTCEPEAQNTTYLWWVNGQSLPVSPRLQLSNGNRTLTLFNVTRNDA RAYVCGIQNSVSANRSDPVTLDVLYGPDTPIISPPDSSYLSGANLNLSCHSASNPSPQ YSWRINGIPQQHTQVLFIAKITPNNNGTYACFVSNLATGRNNSIVKSITVSASGTSPG LSAGATVGIMIGVLVGVALI |
| 38 | 5'-huVK1-SacI-2001 | artificial | Nt | GAGCCGCACG AGCCCGAGCT CCAGATGACC CAGTCTCC |
| 39 | 5'-huVK2/4-SacI-2001 | artificial | Nt | GAGCCGCACG AGCCCGAGCT CGTGATGACY CAGTCTCC |
| 40 | 5'-huVK3-SacI-2001 | artificial | Nt | GAGCCGCACG AGCCCGAGCT CGTGWTGACR CAGTCTCC |
| 41 | 5'-huVK5-SacI-2001 | artificial | Nt | GAGCCGCACG AGCCCGAGCT CACACTCACG CAGTCTCC |
| 42 | 5'-huVK6-SacI-2001 | artificial | Nt | GAGCCGCACG AGCCCGAGCT CGTGCTGACT CAGTCTCC |
| 43 | 3'-hu-Vk-J1-SpeI-BsiW I | artificial | Nt | GACGACACTA GTTGCAGCCA CCGTACGTTT GATTTCCACC TTGGTCC |
| 44 | 3'-hu-Vk-J2/4-SpeI-BsiW I | artificial | Nt | GACGACACTA GTTGCAGCCA CCGTACGTTT GATCTCCASC TTGGTCC |
| 45 | 3'-hu-Vk-J3-SpeI-BsiW I | artificial | Nt | GACGACACTA GTTGCAGCCA CCGTACGTTT GATATCCACT TTGGTCC |
| 46 | 3'-hu-Vk-J5-SpeI-BsiW I | artificial | Nt | GACGACACTA GTTGCAGCCA CCGTACGTTT AATCTCCAGT CGTGTCC |
| 47 | 5"-huVL1a-SacI-2001 | artificial | Nt | GAG CCG CAC GAG CCC GAG CTC GTG TTG ACG CAG CCG CCC TC |
| 48 | 5"-huVL1b-SacI-2001 | artificial | Nt | GAG CCG CAC GAG CCC GAG CTC GTG CTG ACT CAG CCA CCC TC |
| 49 | 5"-huVL2-SacI-2001 | artificial | Nt | GAG CCG CAG GAG CCC GAG CTC GCC CTG ACT CAG CCT SCC TCC GT |
| 50 | 5"-huVL4-SacI-2001 | artificial | Nt | ACC TGC GAG CTC GTG CTG ACT CAR YCM YCC TCT GC |
| 51 | 5"-huVL5-SacI-2001 | artificial | Nt | ACC TGC GAG CTC GTG CTG ACT CAG CCR SCT TCC |
| 52 | 5"-huVL6-SacI-2001 | artificial | Nt | ACC TGC GAG CTC ATG CTG ACT CAG CCC CAC TC |
| 53 | 5"-huVL3/9-SacI-2001 | artificial | Nt | GAG CCG CAC GAG CCC GAG CTC GWG CTG ACT CAG CCA CCY TC |
| 54 | 5"-huVL7/8-SacI-2001 | artificial | Nt | GAG CCG CAC GAG CCC GAG CTC GTG GTG ACY CAG GAG CCM TC |

TABLE 1-continued

| SEQ ID NO. | SOURCE | | SEQUENCE |
|---|---|---|---|
| 55 | 3"-hu-Vlam-BlnI-SpeI-2001 | artificial | Nt CGT GGG ACT AGT CTT GGG CTG ACC TAG GAC GGT |
| 56 | 3"-hu-Vlam2-BlnI-SpeI-2002 | artificial | Nt CGT GGG ACT AGT CTT GGG CTG ACC GAG GAC GGT |
| 57 | 5'-primer 5'-AVH-XhoI | artificial | Nt GTC ACA CTC GAG TCA GGA GGA GGC TTG GTA C |
| 58 | 3'-primer 3'-AVH-BstEll | artificial | Nt GTC ACA GGT GAC CGT GGT CCC TTG GCC CCA G |
| 59 | Flag tag | artificial | AA TGDYKDDDDK |
| 60 | 5'-huVH1,3,5-XhoI-2001 | artificial | Nt AGG TGC AGC TGC TCG AGT CTG G |
| 61 | 5'-huVH4-XhoI-2001 | artificial | Nt CAG GTG CAG CTG CTC GAG TCG GG |
| 62 | 5'-huVH4B-XhoI-2001 | artificial | Nt CAG GTG CAG CTA CTC GAG TGG GG |
| 63 | 3'-hu-VH-BstEll-2001 | artificial | Nt CTG AGG AGA CGG TGA CC |
| 64 | 3'-hu-VH-J3-BstEll-2001 | artificial | Nt CTG AAG AGA CGG TGA CC |
| 65 | 3'-A134-VH1A | artificial | Nt GTA GTC AAA GTA GAA CCG TAG CCC CCT ATC TCT YGC ACA GTA ATA CAC GGC |
| 66 | 3'-A134-VH1B | artificial | Nt GTA GTC AAA GTA GAA CCG TAG CCC CCT ATC TCT YGC ACA GTA ATA CAY RGC |
| 67 | 3'-A134-VH3A | artificial | Nt GTA GTC AAA GTA GAA CCG TAG CCC CCT ATC TCT NGY ACA GTA ATA CAC RGC |
| 68 | 3'-A134-VH3B | artificial | Nt GTA GTC AAA GTA GAA CCG TAG CCC CCT ATC TCT NGC ACA GTA ATA CAA RGC |
| 69 | 3'-A134-VH4 | artificial | Nt GTA GTC AAA GTA GAA CCG TAG CCC CCT ATC TCT SGC ACA GTA ATA CAC RGC |
| 70 | 3' A134-JH6-BstEll, | artificial | Nt CGA GAC GGT GAC CGT GGT CCC TTG GCC CCA GTA GTC AAA GTA GAA CCG TAG CC |
| 71 | A5B7 HC | murine | AA EVQLVESGGGLVQPGGSLRLSCATSGFTFTDYYMNWVRQPPGKALEWLGFIGNKANGYTTEYSASV KGRFTISRDKSQSILYLQMNTLRAEDSATYYCTRDRGLRFYFDYWGQGTTVTVSSASTKGPSVFPLAP SSKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 72 | A5B7 LC | murine | AA DIELTQSPAILSASPGEKVTMTCRASSSVTYIHWYQQKPGSSPKSWIYATSNLASGVPARFSGSGSGT SYSLTISRVEAEDAATYYCQHWSSKPPTFGGGTKLEIKRADAAPTVSIFPPSSEQLTSGGASVVCFL NNFYPKDINVKWKIDGSERQNGVLNSWTDQDSKDSTYSMSSTLTLTKDEYERHNSYTCEATHKTS TSPIVKSFNRNEC |
| 73 | T84.66 HC | murine | AA EVQLQQSGAELVEPGASVKLSCTASGFNIKDTYMHWVKQRPEQGLEWIGRIDPANGNSKYVPKFQGK ATITADTSSNTAYLQLTSLTSEDTAVYYCAPPGYYVSDYAMAYWGQGTSVTVSSASTKGPSVFPLAPS SKSTSGGTAALGCLVKDYFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESNGQPENNYKTTPPVLDSDG SFFLYSKLTVDKSRWQQGNVFSCSVMHEALHNHYTQKSLSLSPGK |
| 74 | T84.66 LC | murine | AA DIVLTQSPASLAVSLGQRATMSCRAGESVDIFGVGFLHWYQQKPGQPPKLLIYRASNLESGIPVRFS GTGSRTDFTLIIDPVEADDVATYYCQQTNEDPYTFGGGTKLEIKRADAAPTVSIFPPSSEQLTSGGA SVVCFLNNFYPKDINVKWKIDGSERQNGVLNSWTDQDSKDSTYSMSSTLTLTKDEYERHNSYTCEAT HKTSTSPIVKSFNRNEC |

TABLE 1-continued

| SEQ ID NO. | | SOURCE | | SEQUENCE |
|---|---|---|---|---|
| 75 | MFE-23 HC | murine | AA | QVKLQQSGAELVRSGTSVKLSCTASGFNIKDSYMHWLRQGPEQGLEWIGWIDPENGDTEYAPKFQG KATFTTDTSSNTAYLQLSSLTSEDTAVYYCNEGTPTGPYYFDYWGQGTTVTVSSASTKGPSVFPLAPS SKSTSGGTAALGCLVKDYFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESNGQPENNYKTTPPVLDSDG SFFLYSKLTVDKSRWQQGNVFSCSVMHEALHNHYTQKSLSLSPGK |
| 76 | MFE-23 LC | murine | AA | ENVLTQSPAIMSASPGEKVTITCSASSSVSYMHWFQQKPGTSPKLWIYSTSNLASGVPARFSGSGSGT SYSLTISRMEAEDAATYYCQQRSSYPLTFGAGTKLELKRADAAPTVSIFPPSSEQLTSGGASVVCFL NNFYPKDINVKWKIDGSERQNGVLNSWTDQDSKDSTYSMSSTLTLTKDEYERHNSYTCEATHKTS TSPIVKSFNRNEC |
| 77 | A5 HC | human | AA | EVQLVESGGGVVQPGRSLRLSCAASGFTLSTYAMHWVRQAPGKGLEWVALISNDGSNKYYADSVKG RFTISRDNSKNTLYLQMNSLRAEDTAVYYCARDRGLRFYFDYWGQGTTVTVSSASTKGPSVFPLAPSS KSTSGGTAALGCLVKDYFPEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 78 | B9 HC | human | AA | EVQLVESGGGLVQPGRSLRLSCAASGFTVSSYWMHWVRQAPGKGLEWVGFIRNKANGGTTEYAASV KGRFTISRDDSKNTLYLQMNSLRAEDTAVYYCARDRGLRFYFDYWGQGTTVTVSSASTKGPSVFPLA PSSKSTSGGTAALGCLVKDYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK |
| 79 | D8 HC | human | AA | EVQLVESGGGVVQPGRSLRLSCAASGFTLSTYAMHWVRQAPGKGLEWVALISNDGSNKYYADSVKG RFTISRDNSKNTLYLQMNSLRAEDTAVYYCTRDRGLRFYFDYWGQGTTVTVSSASTKGPSVFPLAPSS KSTSGGTAALGCLVKDYFPEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 80 | A240 LC | human | AA | QAVLTQPASLSASPGASASLTCTLRRGINVGAYSIYWYQQKPGSPPQYLLRYKSDSDKQQGSGVSSR FSASKDASANAGILLISGLQSEDEADYYCMIWHSGASAVFGGGTKLTVLGQPKAAPSVTLFPPSSEE LQANKATLVCLISDFYPGAVTVAWKADSSPVKAGVETTTPSKQSNNKYAASSYLSLTPEQWKSHKSY SCQVTHEGSTVEKTVAPTECS |
| 81 | 5'-VL CEA I Bsu36I | artificial | Nt | TTCTCTCCTTAGGTGTCCACTCCGACATTGAGCTCACCCAGTCTCC |
| 82 | 3'-VL CEA I Xho I | artificial | Nt | CATGCACTCGAGCTTGGTCCCTCCACCGAACGTC |
| 83 | 5'-VL CEA II Bsu36I | artificial | Nt | TTCTCTCCTTAGGTGTCCACTCCGACATTGTGCTGACCCAATCTCC |
| 84 | 3'-VL CEA II Xho I | artificial | Nt | CATGCACTCGAGCTTGGTCCCCCCACCGAACGTG |
| 85 | 5'-VL CEA III Bsu36I | artificial | Nt | TTCTCTCCTTAGGTGTCCACTCCGAGAACGTTCTCACCCAGTCTCC |
| 86 | 3'-VL CEA III Xho I | artificial | Nt | CATGCACTCGAGCTTGGTCCCAGCACCGAACGTG |
| 87 | 5'-primer 5'-CEA I VH-Bsu36I | artificial | Nt | TTCTCTCCTTAGGTGTCCACTCCCAGGTCCAACTGCAGGAGTCAGG |
| 88 | 3'-primer 3'-CVH-Bsu36I | artificial | Nt | GACTCACCTGAGGAGACGGTGACCGTGGTCCCTTGG |
| 89 | 5'-primer 5'-CEA II VH-Bsu36I | artificial | Nt | TTCTCTCCTTAGGTGTCCACTCCGAGGTTCAGCTGCAGCAGTCTGG |
| 90 | 3'-primer 3'-CEA II VH-Bsu36I | artificial | Nt | GACTCACCTGAGGAGACGGTGACTGAGGTTCCTTGACC |

TABLE 1-continued

| SEQ ID NO. | SOURCE | | SEQUENCE |
|---|---|---|---|
| 91 | 5'-primer 5'-CEA III VH-Bsu36I | artificial Nt | TTCTCTCCTTAGGTGTCCACTCCCAGGTTAAGCTGCAGCAGTCTCC |
| 92 | 3'-primer 3'-CEA III VH-Bsu36I | artificial Nt | GACTCACCTGAGGAGACTGTGACAGTGGTGCCTTGG |
| 93 | 5'-A240-Bsu36I | artificial Nt | TTCTCTCCTTAGGTGTCCACTCCCAGGCCGTGCTGACTCAGCCGGC |
| 94 | 3'-A240-overlap | artificial Nt | GCCTTGGGCTGACCTAGGACGGTCAACTTGGTCC |
| 95 | 5'-primer 5'-Clam-overlap | artificial Nt | GTTGACCGTCCTAGGTCAGCCCAAGGCTGCCCCCTCG |
| 96 | 3'-primer 3'-Clam-NotI | artificial Nt | GACGTAGCGGCCGCGTCGACCTATGAACATTCTGTAGGGGC |
| 97 | 5'-primer 5'-CVH-Bsu36I | artificial Nt | TTCTCTCCTTAGGTGTCCACTCCGAGGTGCAGCTGGTCGAGTC |
| 98 | 3'-primer 3'-CVH-Bsu36I | artificial Nt | GACTCACCTGAGGAGACGGTGACCGTGGTCCCTTGG |
| 99 | CDR-H3* A5B7 Kabat position 95 corresponds to D; Kabat positions 100, 100a, 100b, 101, 102 correspond to FYFDY, respectively | artificial AA | DX$_1$X$_2$X$_3$X$_4$FYFDY with "X$_1$", "X$_2$", "X$_3$" and "X$_4$" corresponding to Kabat positions 96 ("X$_1$"), 97 ("X$_2$"), 98 ("X$_3$") and 99 ("X$_4$"), respectively, of CDR-H3 of murine monoclonal antibody A5B7 and wherein "X" represents any amino acid residue. Preferably, X represents residue "R" (Arginine), "G" (Glycine), "L" (Leucine), "Y" (Tyrosine), "A" (Alanine), "D" (Aspartic acid), "S" (Serine), "W" (Tryptophan), "F" (Phenylalanine) or "T" (Threonine). More preferably, "X$_1$" is "R" (Arginine), "F" (Phenylalanine), "M" (Methionine), "E" (Glutamic acid), or "T" (Threonine); "X$_2$" represents preferably "G" (Glycine), "Y" (Tyrosine), "A" (Alanine), "D" (Aspartic acid), or "S" (Serine); "X$_3$" represents preferably "L" (Leucine), "F" (Phenylalanine), "M" (Methionine), "E" (Glutamic acid), or "T" (Threonine); and "X$_4$" represents preferably "R" (Arginine), "Y" (Tyrosine), "A" (Alanine), "D" (Aspartic acid), or "S" (Serine). |

Abbreviations as used in the sequence listing of Table 1:
AA = amino acid sequence
Nt = nucleotide sequence
HC = heavy chain
LC = light chain
Nucleotide sequence codes:
B = C or G or T
D = A or G or T
H = A or C or T
K = G or T
M = A or C
N = A or C or G or T
R = A or G
S = C or G
V = A or C or G
W = A or T
Y = C or T

The invention claimed is:

1. A pharmaceutical composition comprising an IgG1 antibody specifically binding to human CEA, wherein said IgG1 antibody comprises heavy chain variable ($V_H$) domain and a light chain variable ($V_L$) domain, wherein the heavy chain variable domain comprises:

(1) a CDR-H1 having the amino acid sequence "TYAMH" (SEQ ID NO. 31);

(2) a CDR-H2 having the amino acid sequence "LISNDGSNKYYADSVKG" (SEQ ID NO. 30); and (3) a CDR-H3 having the amino acid sequence "DX1X2X3X4FYFDY" (SEQ ID NO. 99), wherein said X1 is F, M, E or T; X2 is Y, A, D or S; X3 is F, M E or T; and; X4 is Y, A, D or S;

and further comprises light chain variable domain CDRs CDR-L1 having the amino acid sequence "TLRRGIN-VGAYSIY" (SEQ ID NO. 34) and a CDR-L2 having the amino acid sequence "YKSDSDKQQGS" (SEQ ID NO. 33) and a CDR-L3 having the amino acid sequence "MIWHSGASAV" (SEQ ID NO. 32).

2. The pharmaceutical composition of claim 1, which further comprises pharmaceutically suitable carriers, stabilizers and/or excipients.

\* \* \* \* \*

UNITED STATES PATENT AND TRADEMARK OFFICE
CERTIFICATE OF CORRECTION

| | | |
|---|---|---|
| PATENT NO. | : 8,901,278 B2 | Page 1 of 1 |
| APPLICATION NO. | : 13/324823 | |
| DATED | : December 2, 2014 | |
| INVENTOR(S) | : Doris Rau et al. | |

It is certified that error appears in the above-identified patent and that said Letters Patent is hereby corrected as shown below:

<u>In the Claims</u>:

At Column 118, line 60, "X is F, M E" should be -- X3 is F, M, E --.

Signed and Sealed this
Eighth Day of December, 2015

Michelle K. Lee
*Director of the United States Patent and Trademark Office*